United States Patent
Shinohata et al.

(10) Patent No.: US 8,008,518 B2
(45) Date of Patent: Aug. 30, 2011

(54) PROCESS FOR PRODUCING DIALKYL TIN DIALKOXIDES

(75) Inventors: Masaaki Shinohata, Tokyo (JP); Nobuhisa Miyake, Tokyo (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 335 days.

(21) Appl. No.: 12/442,848

(22) PCT Filed: Oct. 3, 2007

(86) PCT No.: PCT/JP2007/069369
§ 371 (c)(1),
(2), (4) Date: Mar. 25, 2009

(87) PCT Pub. No.: WO2008/044575
PCT Pub. Date: Apr. 17, 2008

(65) Prior Publication Data
US 2010/0041908 A1   Feb. 18, 2010

(30) Foreign Application Priority Data

| Oct. 11, 2006 | (JP) | 2006-278017 |
| Dec. 8, 2006 | (JP) | 2006-331451 |
| Mar. 29, 2007 | (JP) | 2007-089150 |
| Mar. 29, 2007 | (JP) | 2007-089752 |

(51) Int. Cl.
*C07F 7/22* (2006.01)
(52) U.S. Cl. .......................... 556/89; 556/88
(58) Field of Classification Search .............. 556/88, 556/89
See application file for complete search history.

(56) References Cited

U.S. PATENT DOCUMENTS

| 5,034,551 | A * | 7/1991 | Vernon et al. ............. 556/89 |
| 5,545,600 | A | 8/1996 | Knudsen et al. |
| 6,768,017 | B2 | 7/2004 | Thoonen |
| 7,435,842 | B2 | 10/2008 | Miyake et al. |
| 7,446,218 | B2 | 11/2008 | Miyake et al. |
| 2004/0077891 | A1 | 4/2004 | Thoonen |
| 2007/0055042 | A1 | 3/2007 | Miyake |
| 2008/0275262 | A1 | 11/2008 | Miyake et al. |
| 2010/0160662 | A1 * | 6/2010 | Bijanto et al. ............. 556/89 |

FOREIGN PATENT DOCUMENTS

EP    1760085    7/2007
(Continued)

OTHER PUBLICATIONS

English translated International Preliminary Patentability Report (IPPR), issued on Apr. 22, 2009.*
Alwyn G. Davies et al. "Organotin Chemistry. Part XI. 1,2, The Preparation of Organotin Alkoxides" Journal of Chemical Society, vol. 23, (1971), pp. 3972-3976.
(Continued)

*Primary Examiner* — Porfirio Nazario Gonzalez
(74) *Attorney, Agent, or Firm* — Morgan, Lewis & Bockius LLP

(57) ABSTRACT

An object of the present invention is to provide a process for producing a dialkyl tin compound from a composition of deactivated forms of a dialkyl tin catalyst, and to provide a process for producing the dialkyl tin catalyst from the dialkyl tin compound and using the dialkyl tin catalyst to produce a carbonic acid ester. According to the present invention, a process for producing a dialkyl tin compound is provided that subjects a composition of the deactivated forms of the dialkyl tin catalyst, formed when producing an ester compound, to an alkyl group redistribution reaction and/or dealkylation reaction.

39 Claims, 7 Drawing Sheets

FOREIGN PATENT DOCUMENTS

| | | |
|---|---|---|
| EP | 1987881 | 5/2008 |
| JP | 44-8489 B | 4/1969 |
| JP | 4-81999 A | 3/1992 |
| JP | 2005298433 A | 10/2005 |
| JP | 2006-28066 A | 2/2006 |
| JP | 2006-83065 A | 3/2006 |
| KR | 200627816 | 3/2006 |
| TW | 200613314 | 5/2006 |
| WO | 02057277 | 7/2002 |
| WO | WO-03/055840 A1 | 7/2003 |
| WO | WO-2004/014840 A1 | 2/2004 |
| WO | WO-2005/111049 A1 | 11/2005 |
| WO | WO-2007/097388 A1 | 8/2007 |

OTHER PUBLICATIONS

Fumio Mori et al., Journal of the Chemical Society of Japan—Industrial Chemistry, vol. 72, No. 7 (1969), 1543-1549.

Jun-Chul Choi et al., "Reaction of Dialkyltin Methoxide with Carbon Dioxide Relevant to the Mechanism of Catalytic Carbonate Synthisis" Journal of American Chemical Society, vol. 121, (1999), pp. 3793-3794.

Toshiyasu Sakakura et al., "Metal-Catalyzed Dimethyl Carbonate Synthesis from Carbon Dioxide and Acetals", The Journal of Organic Chemistry, vol. 64, (1999), pp. 4506-4508.

* cited by examiner

PROCESS FOR PRODUCING DIALKYL TIN DIALKOXIDES

TECHNICAL FIELD

The present invention relates to a process for producing dialkyl tin alkoxide compounds as a catalyst for use in the production of esters and carbonic acid esters, and to a process for producing esters and carbonic acid esters using the dialkyl tin dialkoxide compounds.

BACKGROUND ART

Dialkyl tin dialkoxides are extremely useful as catalysts such as ester synthesis catalysts, carbonic acid ester synthesis catalysts, ester exchange reaction catalysts and silicone polymer or urethane curing catalysts. In particular, in addition to carbonic acid esters being used as additives such as gasoline additives for improving octane value and diesel fuel additives for reducing particles levels in exhaust gas, these useful compounds are also used as alkylation agents, carbonylation agents or solvents and the like during synthesis of polycarbonates, urethanes, pharmaceuticals, agricultural chemicals and other organic compounds, or as lithium battery electrolytes, lubricating oil raw materials and raw materials of deoxygenating agents for rust prevention of boiler pipes, thus resulting in dialkyl tin dialkoxides attracting attention as synthesis catalysts in particular. For example, International Publication No. WO 2003/055840 discloses a process for producing a carbonic acid ester comprising reacting an organometallic compound containing dialkyl tin dialkoxide with carbon dioxide followed by thermal decomposition of the formed addition product.

A conventionally known process for producing dialkyl tin dialkoxides comprises carrying out a dehydration reaction of dialkyl tin oxides and alcohols and removing the resulting low boiling point component that contains water from the reaction liquid (refer to, for example, U.S. Pat. No. 5,545,600, International Publication No. WO 2005/111049, Japanese Patent Application Laid-open No. 2005-298433, Journal of Chemical Society, 23 (1971), 3972, and Journal of the Chemical Society of Japan—Industrial Chemistry, 72, 7 (1969), 1543-1549). Processes for producing the dialkyl tin dialkoxides by the dehydration reaction of the dialkyl tin oxides and the alcohols are presumed to be equilibrium reactions accompanying dehydration as shown in the following formula (1) below:

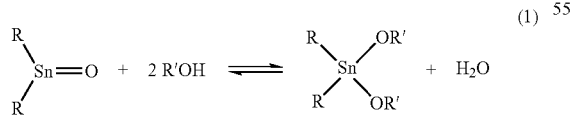

(1)

(wherein R and R' represent alkyl groups).

The above equilibrium is biased overwhelmingly toward the reactants, and is presumed to further contain successive dehydration reactions via tetraalkyl distannoxane as shown in the following formulas (2) and (3):

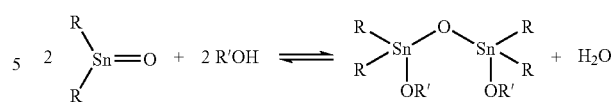

(2)

(wherein R and R' represent alkyl groups);

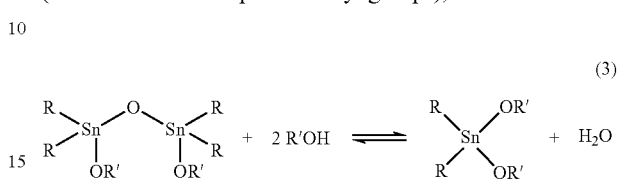

(3)

(wherein R and R' represent alkyl groups).

Although dialkyl tin dialkoxides are produced while removing water generated from each dehydration reaction outside the system in order to obtain the dialkyl tin dialkoxides at high yield, since this reaction is disadvantageous in terms of the reaction energy, the reaction is required to be carried out at a high temperature (for example, 180° C.) for a long period of time.

On the other hand, when dialkyl tin alkoxide compounds (such as dialkyl tin dialkoxides) are heated to, for example, about 180° C., variants are known to be formed such as trialkyl tin alkoxides having three alkyl groups on a single tin atom (see, for example, Journal of the Chemical Society of Japan—Industrial Chemistry, 72, 7 (1969), 1543-1549). Although it is not clear as to the type of reaction by which these trialkyl tin alkoxides are formed, it is presumed that alkyl groups are transferred, for example, and variants are formed by a disproportionation reaction as represented by the following formula (4) in the case said dialkyl tin alkoxide is a tetraalkyl dialkoxy distannoxane, or variants are formed by a disproportionation reaction as represented by the following formula (5) in the case said dialkyl tin alkoxide is a dialkyl tin dialkoxide:

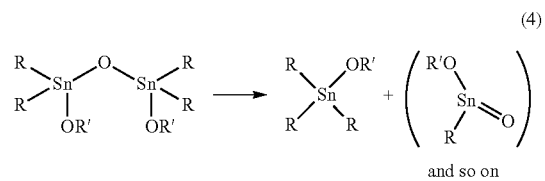

(4)

and so on

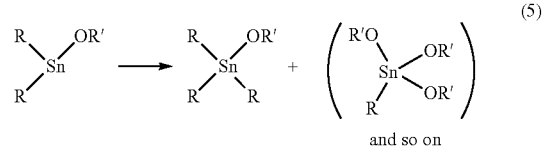

(5)

and so on (wherein R and R' represent alkyl groups).

According to formula (4) above, a trialkyl tin alkoxide and a monoalkyl compound having a single alkyl group on a single tin atom are presumed to be formed as variants of tetraalkyl dialkoxy distannoxane. In actuality, since the inventors of the present invention have confirmed that trialkyl tin alkoxides and high boiling point tin components are included in variants of the tetraalkyl dialkoxy distannoxanes, the high boiling point tin component is assumed to correspond to the monoalkyl compound.

However, the structure of the highly boiling point tin component assumed to correspond to the monoalkyl compound has yet to be identified. Similarly, although variants presumed to be trialkyl tin alkoxides and monoalkyl tin alkoxides are formed from dialkyl tin dialkoxides, the structure of these variants presumed to be said monoalkyl tin alkoxides has not been identified.

The formation of such variants is also confirmed in, for example, the process of producing dialkyl tin dialkoxides as described above, and in processes for producing carbonic acid esters by reacting an organometallic compound containing dialkyl tin dialkoxides with carbon dioxide followed by thermal decomposition of the formed addition product.

Trialkyl tin alkoxides are known to have an extremely poor ability to produce carbonic acid esters in the production of carbonic acid esters by reaction between carbon dioxide and tin compounds (see, for example, Journal of American Chemical Society, 121 (1999), 3793). In addition, high boiling point tin components, included in said variants for which the structure has been unable to be identified, also have an extremely poor ability to produce carbonic acid esters in the production of carbonic acid esters by reaction between carbon dioxide and tin compounds (see, for example, Japanese Patent Application Laid-open No. 2005-298433).

In this manner, since variants do not demonstrate reactivity in the production of carbonic acid esters by the reaction between carbon dioxide and tin compounds, if variants are formed in the production process of said carbonic acid esters, variants of dialkyl tin alkoxide compounds having low activity accumulate when repeatedly using alkyl tin alkoxide compounds, thereby resulting in a decrease in the active form in the form of dialkyl tin dialkoxide compounds, and in turn causing a decrease in the reaction rate or yield of the carbonic acid esters. In such cases, although a method is typically employed, which comprises adding a small amount of fresh dialkyl tin alkoxide compounds in order to make the reaction rate and yield constant, if variants are left as is while simply continuing to add fresh dialkyl tin alkoxide compounds, there may arise the problem of a large amount of degradation products of low activity accumulating in the reaction system. In addition, even in the case of removing a portion of a mixture of alkyl tin alkoxide compounds containing variants of dialkyl tin alkoxide compounds from the reaction system while adding fresh dialkyl tin alkoxide compounds to maintain a constant concentration of dialkyl tin alkoxide compound in the reaction system, in addition to the removed variants of the dialkyl tin alkoxide compound becoming waste, since the active form in the form of the dialkyl tin alkoxide compound is also removed and discarded, significant problems occur in terms of costs and waste processing.

Several solutions to the above problems have been previously proposed (see, for example, International Publication No. WO 2004/014840 and International Publication No. WO 2007/097388). More specifically, International Publication No. WO 2004/014840 proposes a method used in the production of carbonic acid esters using dialkyl tin alkoxide compounds containing thermal denaturation products of dialkyl tin alkoxide compounds for separating trialkyl tin compound components from dialkyl tin alkoxide compounds containing said thermal denaturation products to prevent their accumulation in the reaction system. However, since high boiling point tin compounds having an unidentifiable structure contained in variants of the dialkyl tin alkoxide compounds are unable to be removed, the accumulation of variants of dialkyl tin alkoxide compounds cannot be completely prevented with this method.

In addition, the inventors of the present invention disclosed a method for separating and recovering products formed via dialkyl tin alkoxide compounds in the form of dialkyl tin dialkoxides by preliminarily reacting a dialkyl tin alkoxide compound and variants of the dialkyl tin alkoxide compound extracted from the reaction system with an alcohol and/or carbonic acid ester (see International Publication No. WO 2007/097388). According to this method, the problem of the active form in the form of the dialkyl tin alkoxide compound being discarded with the variants is resolved, enabling only variants of dialkyl tin alkoxide compounds to be selectively discarded. However, since variants of the dialkyl tin alkoxide compounds cannot be reused, the problems of costs and waste processing remain.

On the basis of this background, there is a need for the development of a technology that allows variants of dialkyl tin alkoxide compounds to be regenerated into an active form in the form of dialkyl tin alkoxide compounds and be reused in the production of carbonic acid esters.

Proportionation reactions, which are the reverse reactions of the above-mentioned disproportionation reactions, are used as a method to obtain dialkyl tin compounds from mixtures of two types of compounds having different numbers of alkyl groups on the tin atom. For example, in the case of tin halide compounds, dialkylchloro tin is formed by a proportionation reaction between trialkylchloro tin and alkyltrichloro tin as represented by the following formula (6) (see, for example, Japanese Patent Application Laid-open No. H4-81999).

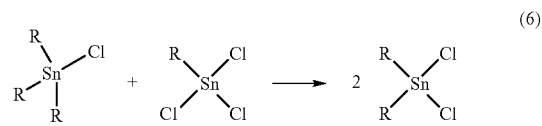

(6)

As previously described, disproportionation reactions that denature dialkyl tin alkoxide compounds into trialkyl tin alkoxides and monoalkyl tin compounds by a disproportionation reaction are advantageous in the case of tin alkoxide compounds, and it is difficult for the reverse reaction in the form of the proportionation reaction to occur. On the other hand, proportionation reactions are advantageous in the case of tin halide compounds, allowing the obtaining of dialkyldichloro tin from trialkylchloro tin and alkyltrichloro tin.

Several methods have been previously proposed for the production of alkyltrichloro tin (see, for example, Japanese Patent Application Laid-open No. H4-81999 and Japanese Patent Application Laid-open No. S44-8489). More specifically, Japanese Patent Application Laid-open No. H4-81999 discloses a method for producing alkyltrichloro tin using the proportionation reaction as described above using a mixture of tetraalkyl tin and tetrachloro tin at a specific ratio. Japanese Patent Application Laid-open No. S44-8489 discloses a method for producing alkyltrichloro tin by reacting alkane stannonate and hydrogen chloride. However, a technology is not yet known for producing alkyltrichloro tin compounds by using as raw materials variants of dialkyl tin alkoxide compounds.

On the other hand, reactions in which trialkyl tin acetoxides and alkyl tin acetoxide oxides are formed by reacting variants of dialkyl tin alkoxide compounds with acetic acid have been disclosed as reactions of variants of dialkyl tin alkoxide compounds (see, for example, Journal of American Chemical Society, 121 (1999), 3793). However, a method is not yet known for producing dialkyl tin alkoxide compounds by the proportionation reaction between trialkyl tin acetoxides and alkyl tin acetoxide oxide compounds.

On the basis of the above, since the development of technologies for regenerating variants of dialkyl tin alkoxide compounds into active forms in the form of dialkyl tin alkoxide compounds has yet to be achieved, the problems of costs and waste processing in the production process of carbonic acid esters remain unsolved.

DISCLOSURE OF INVENTION

Problems to be Solved by the Invention

An object of the present invention is to provide a process for producing dialkyl tin compounds that enables variants of dialkyl tin alkoxide compounds to be regenerated into dialkyl tin alkoxide compounds, and also to provide a process for using said dialkyl tin compounds in the production of carbonic acid esters.

Means for Solving the Problems

As a result of conducting extensive studies on the above-mentioned problems, the inventors of the present invention found that the above-mentioned problems can be solved by producing a dialkyl tin compound by reacting an acid and/or acid anhydride with a composition containing a variant of a dialkyl tin alkoxide compound followed by heat-treating said dialkyl tin compound, and then regenerating said dialkyl tin compound into a dialkyl tin alkoxide compound and using in the production of a carbonic acid ester, thereby leading to completion of the present invention. In other words, the present invention is as described below.

The present invention provides:

[1] a process for producing a dialkyl tin compound, comprising:

subjecting a composition of a deactivated form of a dialkyl tin catalyst, which is formed when producing an ester compound using the dialkyl tin catalyst, to an alkyl group redistribution reaction and/or dealkylation reaction,

[2] the process according to item [1], wherein the dialkyl tin catalyst is at least one type of compound selected from the group consisting of a dialkyl tin compound represented by formula (1) and a tetraalkyl distannoxane compound represented by formula (2):

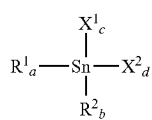
(1)

(wherein each of $R^1$ and $R^2$ independently represents a linear or branched alkyl group having 1 to 12 carbon atoms, each of $X^1$ and $X^2$ independently represents at least one type of substituent selected from the group consisting of an alkoxy group, an acyloxyl group and a halogen atom, a and b independently represent an integer of 0 to 2 and a+b=2, and c and d independently represent an integer of 0 to 2 and c+d=2;

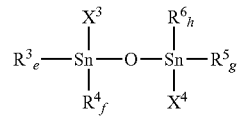
(2)

(wherein, each of $R^3$, $R^4$, $R^5$ and $R^6$ independently represents a linear or branched alkyl group having 1 to 12 carbon atoms, each of $X^3$ and $X^4$ independently represents at least one type of substituent selected from the group consisting of an alkoxy group, an acyloxyl group and a halogen atom, and e, f, g and h independently represent an integer of 0 to 2, e+f=2 and g+h=2).

[3] the process according to item [2], wherein in formulas (1) and (2), the number of carbon atoms constituting $X^1$, $X^2$, $X^3$ and $X^4$ is a number selected from an integer of 0 to 12,

[4] the process according to any one of items [1] to [3], wherein the ester compound is at least one type of compound selected from the group consisting of carboxylic acid ester, carbaminic acid ester and isocyanate,

[5] the process according to item [4], wherein the carboxylic acid ester is a carbonic acid ester,

[6] the process according to item [5], wherein the composition of the deactivated form of the dialkyl tin catalyst is a composition containing a deactivated form of the dialkyl tin catalyst generated during a step of producing a carbonic acid ester from carbon dioxide and the dialkyl tin catalyst,

[7] the process according to any one of items [1] to [6], wherein the deactivated form of the dialkyl tin catalyst is a heat-deactivated form of the dialkyl tin catalyst,

[8] the process according to any one of items [1] to [7], wherein the deactivated form of the dialkyl tin catalyst is a deactivated form of the dialkyl tin catalyst originating from the dialkyl tin catalyst in which the number of alkyl group bound to a single tin atom differs from the number of alkyl group bound to a single tin atom of the dialkyl tin catalyst,

[9] the process according to any one of items [1] to [8], wherein at least one type of the deactivated form of the dialkyl tin catalyst is a trialkyl tin compound,

[10] the process according to any one of items [1] to [9], wherein the deactivated form of the dialkyl tin catalyst is a trialkyl tin compound and an organic tin compound containing a tin atom demonstrating a chemical shift at from −220 to −610 ppm based on a tetramethyl tin when analyzed by $^{119}$Sn-NMR in a heavy chloroform solution,

[11] the process according to item [10], further comprising separating the composition of the deactivated form of the dialkyl tin catalyst into a composition containing the trialkyl tin compound and a composition containing the compound containing a tin atom demonstrating a chemical shift at from −220 to −610 ppm based on a tetramethyl tin when analyzed by $^{119}$Sn-NMR in a heavy chloroform solution,

[12] the process according to item [11], wherein the separation step is carried out by at least one method selected from the group consisting of distillation separation, extraction separation and membrane separation,

[13] the process according to any one of items [1] to [12], wherein in a case that pKa of a conjugated acid with respect to at least one substituent among groups bound to tin atoms of the deactivated form of the dialkyl tin catalyst other than alkyl groups originating from the dialkyl tin catalyst is 0 to 6.8, the alkyl group redistribution reaction is an alkyl group redistribution reaction in which an organic tin compound having an Sn—Y bond (wherein Y represents Y in which pKa of a conjugated acid of Y in a form of HY, in which a hydrogen atom has been added to Y, is 0 to 6.8) is heat-treated,

[14] the process according to any one of items [1] to [12], wherein in a case that pKa of a conjugated acid with respect to at least one substituent among groups bound to tin atoms of the deactivated form of the dialkyl tin catalyst other than alkyl groups originating from the dialkyl tin catalyst is 6.8 to 25, the alkyl group redistribution reaction comprises the steps of:

(A) obtaining an organic tin compound having an Sn—Y bond by substituting all or a portion of the ligands of the deactivated form (excluding an alkyl group originating from the dialkyl tin catalyst and bound to tin) with a substituent Y; and (B) heat-treating the organic compound having an Sn—Y bond and obtained in step (A) (wherein Y represents Y in which pKa of a conjugated acid of Y in a form of HY, in which a hydrogen atom has been added to Y, is 0 to 6.8),

[15] the process according to item [14], wherein the step (A) comprises producing an organic tin compound having an Sn—Y bond in which three alkyl groups and a single Y group originating from an acid and/or acid anhydride are bound to a single tin atom, and an organic tin compound having an Sn—Y bond in which a single alkyl group and a number of Y groups originating from an acid and/or acid anhydride, the number of Y groups being selected from an integer of 1 to 3, are bound to a single tin atom, by reacting the composition of deactivated form of the dialkyl tin catalyst with the acid represented by the following formula (3) and/or the acid anhydride represented by the following formula (4):

$$HY \quad (3)$$

(wherein Y represents Y in which pKa of a conjugated acid of Y in a form of HY, in which a hydrogen atom has been added to Y, is 0 to 6.8);

$$YOY \quad (4)$$

(wherein Y represents Y in which pKa of a conjugated acid of Y in a form of HY, in which a hydrogen atom has been added to Y, is 0 to 6.8, and O represents an oxygen atom),

[16] the process according to item [15], wherein the step (A) is carried out while removing water generated during a use of acid in the step (A) by at least one method selected from the group consisting of removal with a dehydrating agent, distillation separation and membrane separation,

[17] the process according to any one of items [1] to [12], wherein the dealkylation reaction comprises forming an Sn—Y bond by eliminating an alkyl group from the deactivated form of the dialkyl tin catalyst (wherein Y represents Y in which pKa of a conjugated acid of Y in a form of HY, in which a hydrogen atom has been added to Y, is 0 to 6.8),

[18] the process according to any one of items [9] to [12], wherein the dealkylation reaction forms a single Sn—Y bond by eliminating a single alkyl group from the trialkyl tin compound contained in the composition of the deactivated form of the dialkyl tin catalyst to obtain a dialkyl tin compound having an Sn—Y bond (wherein Y represents Y in which pKa of a conjugated acid of Y in a form of HY, in which a hydrogen atom has been added to Y, is 0 to 6.8),

[19] the process according to item [18], wherein the forming step of the Sn—Y bond comprises reacting the trialkyl tin compound contained in the composition of the deactivated form of the dialkyl tin catalyst with an acid represented by formula (5) and/or an acid anhydride represented by formula (6):

$$HY \quad (5)$$

(wherein Y represents Y in which pKa of a conjugated acid of Y in a form of HY, in which a hydrogen atom has been added to Y, is 0 to 6.8);

$$YOY \quad (6)$$

(wherein Y represents Y in which pKa of a conjugated acid of Y in a form of HY, in which a hydrogen atom has been added to Y, is 0 to 6.8, and O represents an oxygen atom),

[20] the process according to item [15] or [19], wherein the acid and/or the acid anhydride is a liquid or gas at 60° C.,

[21] the process according to item [20], wherein the acid is a hydrohalogenic acid,

[22] the process according to item [20], wherein the acid is a hydrogen halide,

[23] the process according to item [20], wherein the acid is an organic acid,

[24] the process according to item [23], wherein the organic acid is a carboxylic acid,

[25] the process according to item [20], wherein a standard boiling point of the acid anhydride is 300° C. or lower,

[26] the process according to item [25], wherein the acid anhydride is acetic anhydride or maleic anhydride,

[27] the process according to any one of items [1] to [26], wherein the dialkyl tin compound has two alkyl groups originating from a dialkyl tin catalyst and bound to a single tin atom while simultaneously having at least one Sn—Y bond (wherein Y represents Y in which pKa of a conjugated acid of Y in a form of HY, in which a hydrogen atom has been added to Y, is 0 to 6.8),

[28] the process according to item [27], wherein the dialkyl tin compound is at least one type of compound selected from the group consisting of a dialkyl tin compound represented by formula (7) and a tetraalkyl distannoxane compound represented by formula (8):

(7)

(wherein $R^7$ and $R^8$ represent a group originating from the dialkyl tin catalyst, and independently represent a linear or branched alkyl group having 1 to 12 carbon atoms, Y represents a group originating from the dialkyl tin catalyst or a group originating from the acid (HY) and/or acid anhydride (YOY), pKa of a conjugated acid of Y in a form of HY in which a hydrogen atom has been added to Y is 0 to 6.8, and i and j independently represent an integer of 0 to 2, and i+j=2);

(8)

(wherein $R^9$, $R^{10}$, $R^{11}$ and $R^{12}$ represents a group originating from the dialkyl tin catalyst, and independently represent a linear or branched alkyl group having 1 to 12 carbon atoms, Y represents a group originating from the dialkyl tin catalyst or a group originating from the acid (HY) and/or acid anhydride (YOY), pKa of a conjugated acid of Y in a form of HY in which a hydrogen atom has been added to Y is 0 to 6.8, and k, l, m and n respectively represent an integer of 0 to 2, k+l=2 and m+n=2),

[29] the process according to any one of items [14] to [26], further comprising, following the step (B), a step (I) of substituting substituent Y of the dialkyl tin compound having an Sn—Y bond with at least one type of substituent selected from the group consisting of an alkoxy group, and acyloxyl group and halogen atom,

[30] the process according to item [29], wherein the step (I) comprises:

a step (I-1) of obtaining a composition containing a dialkyl tin oxide by hydrolyzing the dialkyl tin compound having an Sn—Y bond by adding an aqueous alkaline solution; and a step (I-2) of reacting the composition containing the dialkyl tin oxide, obtained in the step (I-1) with at least one type of compound selected from the group consisting of alcohol, carboxylic acid and hydrogen halide, followed by removing a component containing a generated water from a reaction liquid,

[31] the process according to item [30], wherein the aqueous alkaline solution is at least one type of aqueous alkaline solution selected from the group consisting of an aqueous sodium hydroxide solution, an aqueous potassium hydroxide solution, an aqueous potassium carbonate solution and an aqueous sodium carbonate solution,

[32] the process according to item [30] or [31], wherein the step (I-2) is a step in which the compound reacted with the composition containing the dialkyl tin oxide is alcohol, and a dialkyl tin alkoxide compound is obtained,

[33] the process according to item [6], wherein the step for producing a carbonic acid ester comprises:

a step (1) of obtaining a reaction liquid containing the carbonic acid ester by reacting carbon dioxide and the dialkyl tin catalyst;

a step (2) of obtaining a residual liquid by separating the carbonic acid ester from the reaction liquid;

a step (3) of regenerating the dialkyl tin catalyst by reacting the residual liquid and alcohol, and removing a generated water outside the system; and a step (4) of recycling the dialkyl tin catalyst obtained in step (3) to step (1),

[34] the process according to item [33], wherein the step of regenerating the dialkyl tin catalyst from the composition of the deactivated form of the dialkyl tin catalyst generated during the step for producing the carbonic acid ester by the alkyl group redistribution reaction and/or the dealkylation reaction is carried out after the step (2) and/or the step (3), and the regenerated dialkyl tin catalyst is recycled and reused as the dialkyl tin catalyst of the step (4) and/or the step (1),

[35] the process according to item [34], wherein the step of regenerating the dialkyl tin catalyst is a step which uses the steps according to any one of Claims 29 to 32 and in which substituent Y represents an acyloxyl group,

[36] the process according to any one of items [1] and [33] to [35], wherein the dialkyl tin catalyst is a dialkyl tin alkoxide compound,

[37] the process according to any one of items [33] to [36], wherein the dialkyl tin catalyst is a dialkyl tin alkoxide compound, and $X^1$, $X^2$, $X^3$ and $X^4$ of a compound represented by formula (1) and/or formula (2) represent alkoxy groups:

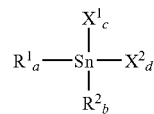
(1)

(wherein each of $R^1$ and $R^2$ independently represents a linear or branched alkyl group having 1 to 12 carbon atoms, each of $X^1$ and $X^2$ independently represents at least one type of substituent selected from the group consisting of an alkoxy group, an acyloxyl group and a halogen atom, a and b independently represent an integer of 0 to 2 and a+b=2, and c and d independently represent an integer of 0 to 2 and c+d=2);

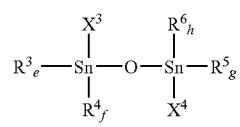
(2)

(wherein each of $R^3$, $R^4$, $R^5$ and $R^6$ independently represents a linear or branched alkyl group having 1 to 12 carbon atoms, each of $X^3$ and $X^4$ independently represents at least one type of substituent selected from the group consisting of an alkoxy group, an acyloxyl group and a halogen atom, e, f, g and h respectively represent an integer of 0 to 2, e+f=2 and g+h=2),

[38] the process according to item [37], wherein the dialkyl tin catalyst is a dialkyl tin alkoxide, and $R^1$, $R^2$, $R^3$, $R^4$, $R^5$ and $R^6$ of the compound represented by the formula (1) and/or the formula (2) simultaneously represents a n-butyl group or a n-octyl group,

[39] the process according to any one of items [33] to [38], wherein the alcohol is an alcohol represented by the following formula (9):

(9)

(wherein R represents a linear or branched alkyl group having 4 to 8 carbon atoms).

ADVANTAGEOUS EFFECTS OF THE INVENTION

According to the present invention, a useful component in the form of a dialkyl tin compound can be obtained from a composition containing variants of a dialkyl tin alkoxide compound, and the dialkyl tin compound can be reused to produce a carbonic acid ester after having converted to a dialkyl tin alkoxide compound, thereby making the present invention extremely useful in industrial fields.

DESCRIPTION OF REFERENCE NUMERICALS

Figure 1:
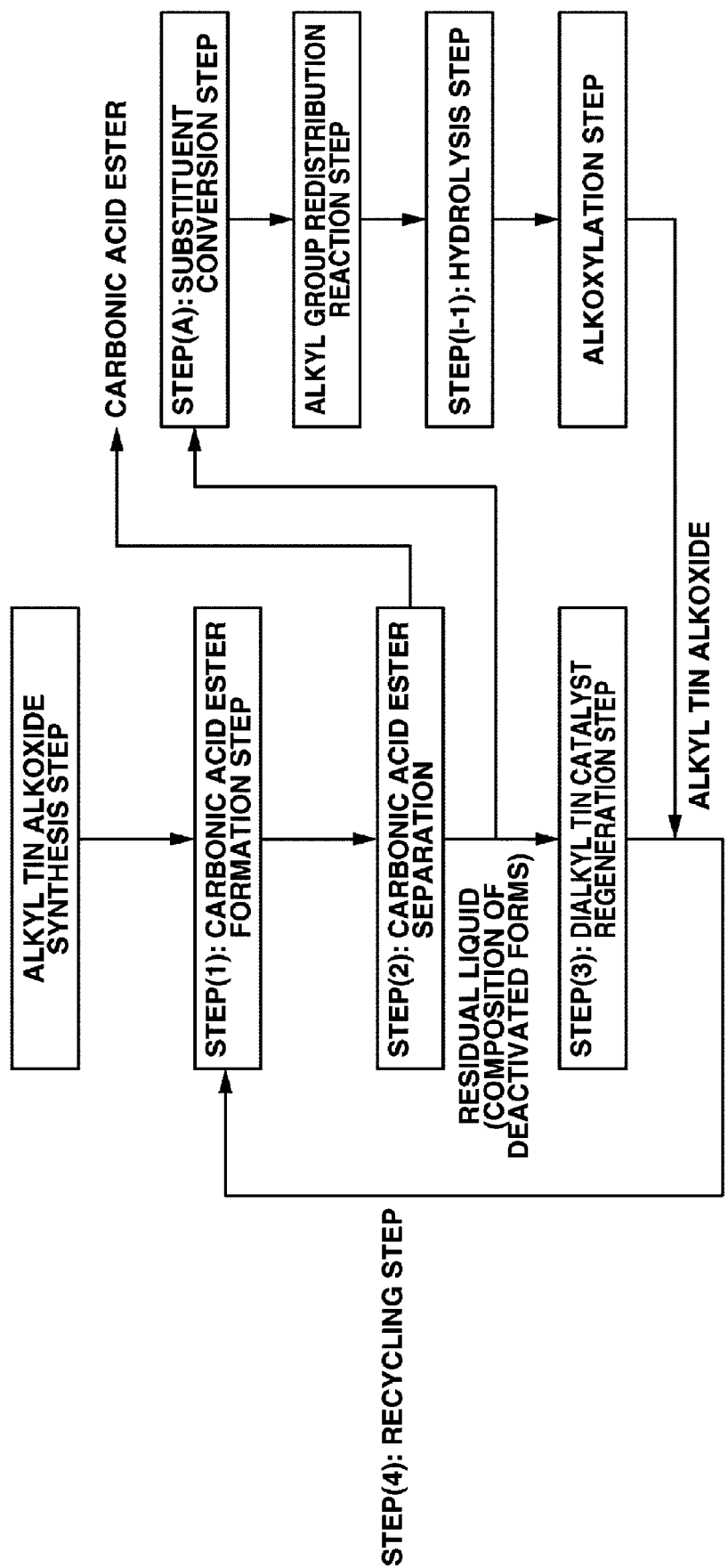
FIG. 1 illustrates a schematic drawing showing an improved process for producing carbonic acid esters by combining the production process according to the present embodiment of the present invention.

101, 107: distillation column, 102: column-type reaction vessel, 103, 106: thin film evaporator, 104: autoclave, 105: decarbonization tank, 111, 112, 117: reboiler, 121, 123, 126, 127: condenser, 1, 9: supply line, 2, 4, 5, 6, 7, 8, 10, 11, 12, 13, 14: transfer line, 3, 15: recovery line, 16: extraction line, 17: feed line.

BEST MODE FOR CARRYING OUT THE INVENTION

The following provides a detailed explanation of preferred embodiments of the present invention (to be referred to as "the present embodiments"). Furthermore, the present invention is not limited to the following embodiments, but rather can be carried out without departing from the spirit and scope thereof.

First, an explanation is provided of compounds used in the present embodiments.

<Dialkyl Tin Catalyst>

In the present embodiments, the terms "dialkyl tin compound", "dialkyl tin catalyst" and "dialkyl tin" which are used herein refer to organic tin compounds in which two alkyl groups are bound to a single tin atom.

A dialkyl tin catalyst in the present embodiments refers to an organic tin compound that demonstrates catalytic action in the production of ester compounds and in which two alkyl groups are bound to a single tin atom.

Examples of said dialkyl tin catalyst include compounds selected from at least one type of compound selected from the group consisting of the dialkyl tin compound represented by the following formula (18) and the tetraalkyl distannoxane compound represented by the following formula (19):

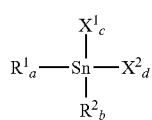

(18)

(wherein each of $R^1$ and $R^2$ independently represents a linear or branched alkyl group having 1 to 12 carbon atoms, each of $X^1$ and $X^2$ independently represents at least one type of substituent selected from the group consisting of an alkoxy group, an acyloxyl group and a halogen atom, a and b respectively represent an integer of 0 to 2 and a+b=2, and c and d respectively represent an integer of 0 to 2 and c+d=2);

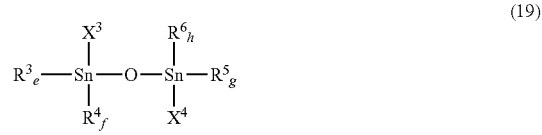

(19)

(wherein each of $R^3$, $R^4$, $R^5$ and $R^6$ independently represents a linear or branched alkyl group having 1 to 12 carbon atoms, each of $X^3$ and $X^4$ independently represents at least one type of substituent selected from the group consisting of an alkoxy group, an acyloxyl group and a halogen atom, and e, f, g and h respectively represent an integer of 0 to 2, e+f=2 and g+h=2).

Examples of $R^1$ and $R^2$ of the dialkyl tin catalyst represented by formula (18) in the present embodiments and $R^3$, $R^4$, $R^5$ and $R^6$ of the tetraalkyl distannoxane compound represented by formula (19) in the present embodiments include alkyl groups in the form of aliphatic hydrocarbon groups in which the number of carbon atoms constituting said groups is a number selected from an integer of 1 to 12, such as a methyl, ethyl, propyl (isomers), butyl (isomers), pentyl (isomers), hexyl (isomers), heptyl (isomers), octyl (isomers), nonyl (isomers), decyl (isomers), dodecyl (isomers) group or the like. Preferable examples include linear or branched alkyl groups in which the number of carbon atoms constituting said groups is a number selected from an integer of 1 to 8, and although a dialkyl tin catalyst can be used in which the alkyl groups are alkyl groups in which the number of carbon atoms constituting said groups is outside the indicated range, fluidity may become poor and productivity may be impaired. More preferable examples of the alkyl groups include n-butyl groups or n-octyl groups in consideration of ease of acquisition during industrial production.

$X^1$ and $X^2$ of the dialkyl tin catalyst represented by formula (18) in the present embodiments and $X^3$ and $X^4$ of the tetraalkyl distannoxane compound represented by formula (19) in the present embodiments represent at least one type of substituent selected from the group consisting of alkoxy groups, acyloxyl groups and halogen atoms, and in the case said group is the alkoxy group and/or acyloxyl group, the number of carbon atoms constituting said group is preferably a number selected from an integer of 0 to 12. Examples of such groups include alkoxy groups composed of linear or branched saturated alkyl groups and oxygen atoms, such as a methoxy group, an ethoxy group, a propoxy group (isomers), a butoxy group (isomers), a pentyloxy group (isomers), a hexyloxy group (isomers), a heptyloxy group (isomers), an octyloxy group (isomers), a nonyloxy group (isomers), a decyloxy group (isomers) or the like; acyloxyl groups composed of linear or branched saturated alkyl groups, carbonyl groups and oxygen atoms, such as an acetoxy group, a propionyloxy group, a butyryloxy group, a valeryloxy group, a lauroyloxy group or the like; and halogen atoms such as a chloro group, a bromo group or the like. Preferable examples include alkoxy groups having 4 to 6 carbon atoms in consideration of fluidity and solubility as well as in consideration of use as a catalyst for production of carbonic acid esters.

Examples of dialkyl tin catalysts represented by formula (18) include dialkyl-dialkoxy tin such as dimethyl-dimethoxy tin, dimethyl-diethoxy tin, dimethyl-dipropoxy tin (isomers), dimethyl-dibutoxy tin (isomers), dimethyl-dipentyloxy tin (isomers), dimethyl-dihexyloxy tin (isomers), dimethyl-diheptyloxy tin (isomers), dimethyl-dioctyloxy tin (isomers), dimethyl-dinonyloxy tin (isomers), dimethyl-didecyloxy tin (isomers), dibutyl-dimethoxy tin (isomers), dibutyl-diethoxy tin (isomers), dibutyl-dipropoxy tin (isomers), dibutyl-dibutyloxy tin (isomers), dibutyl-dipentyloxy tin (isomers), dibutyl-dihexyloxy tin (isomers), dibutyl-diheptyloxy tin (isomers), dibutyl-dioctyloxy tin (isomers), dibutyl-dinonyloxy tin (isomers), dibutyl-didecyloxy tin (isomers), dioctyl-dimethoxy tin (isomers), dioctyl-diethoxy tin (isomers), dioctyl-dipropoxy tin (isomers), dioctyl-dibutyloxy tin (isomers), dioctyl-dipentyloxy tin (isomers), dioctyl-dihexyloxy tin (isomers), dioctyl-diheptyloxy tin (isomers), dioctyl-dioctyloxy tin (isomers), dioctyl-dinonyloxy tin (isomers), dioctyl-didecyloxy tin (isomers) or the like; dialkyl-diacyloxy tin such as dimethyl-diacetoxy tin, dimethyl-dipropionyloxy tin (isomers), dimethyl-dibutyryloxy tin (isomers), dimethyl-valeryloxy tin (isomers), dimethyl-dilaurolyloxy tin (isomers), dibutyl-diacetoxy tin (isomers), dibutyl-dipropionyloxy tin (isomers), dibutyl-dibutyryloxy tin (isomers), dibutyl-divaleryloxy tin (isomers), dibutyl-dilaurolyloxy tin (isomers), dioctyl-diacetoxy tin (isomers), dioctyl-dipropionyloxy tin (isomers), dioctyl-dibutyryloxy tin (isomers), dioctyl-valeryloxy tin (isomers), dioctyl-dilaurolyloxy tin (isomers) or the like; and, dialkyl-dihalide tin such as dimethyl-dichloro tin, dimethyl-dibromo tin, dibutyl-dichloro tin (isomers), dibutyl-dibromo tin (isomers), dioctyl-dichloro tin (isomers), dioctyl-dibromo tin (isomers) or the like.

Among these, dialkyl tin dialkoxides such as dimethyl-dimethoxy tin, dimethyl-diethoxy tin, dimethyl-dipropoxy tin (isomers), dimethyl-dibutoxy tin (isomers), dimethyl-dipentyloxy tin (isomers), dimethyl-dihexyloxy tin (isomers), dimethyl-diheptyloxy tin (isomers), dimethyl-dioctyloxy tin (isomers), dimethyl-dinonyloxy tin (isomers), dimethyl-didecyloxy tin (isomers), dibutyl-dimethoxy tin (isomers), dibutyl-diethoxy tin (isomers), dibutyl-dipropoxy tin (isomers), dibutyl-dibutyloxy tin (isomers), dibutyl-dipentyloxy tin (isomers), dibutyl-dihexyloxy tin (isomers), dibutyl-diheptyloxy tin (isomers), dibutyl-dioctyloxy tin (isomers), dibutyl-dinonyloxy tin (isomers), dibutyl-didecyloxy tin (isomers), dioctyl-dimethoxy tin (isomers), dioctyl-diethoxy tin (isomers), dioctyl-dipropoxy tin (isomers), dioctyl-dibutyloxy tin (isomers), dioctyl-dipentyloxy tin (isomers), dioctyl-dihexyloxy tin (isomers), dioctyl-diheptyloxy tin (isomers), dioctyl-dioctyloxy tin (isomers), dioctyl-dinonyloxy tin (isomers) or dioctyl-didecyloxy tin (isomers) are preferable, dialkyl-dialkoxy tin such as dibutyl-dipropoxy tin (isomers), dibutyl-dibutyloxy tin (isomers), dibutyl-dipentyloxy tin (isomers), dibutyl-dihexyloxy tin (isomers), dibutyl-diheptyloxy tin (isomers), dioctyl-dipropoxy tin (isomers), dioctyl-dibutoxy tin (isomers), dioctyl-dipentyloxy tin (isomers), dioctyl-dihexyloxy tin (isomers) or dioctyl-diheptyloxy tin (isomers) are more preferable, and dibutyl-dibutyloxy tin (isomers), dibutyl-dipentyloxy tin (isomers), dibutyl-dihexyloxy tin (isomers), dibutyl-diheptyloxy tin (isomers), dibutyl-dioctyloxy tin (isomers), dioctyl-dibutyloxy tin (isomers), dioctyl-dipentyloxy tin (isomers), dioctyl-dihexyloxy tin (isomers), dioctyl-diheptyloxy tin (isomers) or dioctyl-dioctyloxy tin (isomers) is more preferable.

Although the monomer structure of the dialkyl tin catalyst is shown in formula (18), this may be a polymer structure or aggregate structure.

Examples of the tetraalkyl dialkoxy distannoxane represented by the formula (19) include 1,1,3,3-tetraalkyl-1,3-dialkoxy distannoxanes such as 1,1,3,3-tetramethyl-1,3-dimethoxy distannoxane, 1,1,3,3-tetramethyl-1,3-diethoxy distannoxane, 1,1,3,3-tetramethyl-1,3-dipropoxy distannoxane (isomers), 1,1,3,3-tetramethyl-1,3-dibutoxy distannoxane (isomers), 1,1,3,3-tetramethyl-1,3-dipentyloxy distannoxane (isomers), 1,1,3,3-tetramethyl-1,3-dihexyloxy distannoxane (isomers), 1,1,3,3-tetramethyl-1,3-diheptyloxy distannoxane (isomers), 1,1,3,3-tetramethyl-1,3-dioctyloxy distannoxane (isomers), 1,1,3,3-tetramethyl-1,3-dinonyloxy distannoxane (isomers), 1,1,3,3-tetramethyl-1,3-didecyloxy distannoxane (isomers), 1,1,3,3-tetrabutyl-1,3-dimethoxy distannoxane (isomers), 1,1,3,3-tetrabutyl-1,3-diethoxy distannoxane (isomers), 1,1,3,3-tetrabutyl-1,3-dipropoxy distannoxane (isomers), 1,1,3,3-tetrabutyl-1,3-dibutoxy distannoxane (isomers), 1,1,3,3-tetrabutyl-1,3-dipentyloxy distannoxane (isomers), 1,1,3,3-tetrabutyl-1,3-dihexyloxy distannoxane (isomers), 1,1,3,3-tetrabutyl-1,3-diheptyloxy distannoxane (isomers), 1,1,3,3-tetrabutyl-1,3-dioctyloxy distannoxane (isomers), 1,1,3,3-tetrabutyl-1,3-dinonyloxy distannoxane (isomers), 1,1,3,3-tetrabutyl-1,3-didecyloxy distannoxane (isomers), 1,1,3,3-tetraoctyl-1,3-dimethoxy distannoxane (isomers), 1,1,3,3-tetraoctyl-1,3-diethoxy distannoxane (isomers), 1,1,3,3-tetraoctyl-1,3-dipropoxy distannoxane (isomers), 1,1,3,3-tetraoctyl-1,3-dibutoxy distannoxane (isomers), 1,1,3,3-tetraoctyl-1,3-dipentyloxy distannoxane (isomers), 1,1,3,3-tetraoctyl-1,3-dihexyloxy distannoxane (isomers), 1,1,3,3-tetraoctyl-1,3-diheptyloxy distannoxane (isomers), 1,1,3,3-tetraoctyl-1,3-dioctyloxy distannoxane (isomers), 1,1,3,3-tetraoctyl-1,3-dinonyloxy distannoxane (isomers), 1,1,3,3-tetraoctyl-1,3-didecyloxy distannoxane (isomers) or the like; 1,1,3,3-tetraalkyl-1,3-diacyloxy distannoxanes such as 1,1,3,3-tetramethyl-1,3-diacetoxy distannoxane, 1,1,3,3-tetramethyl-1,3-dipropionyloxy distannoxane (isomers), 1,1,3,3-tetramethyl-1,3-dibutyryloxy distannoxane (isomers), 1,1,3,3-tetramethyl-1,3-divaleryloxy distannoxane (isomers), 1,1,3,3-tetramethyl-1,3-dilauroyloxy distannoxane (isomers), 1,1,3,3-tetrabutyl-1,3-diacetoxy distannoxane (isomers), 1,1,3,3-tetrabutyl-1,3-dipropionyloxy distannoxane (isomers), 1,1,3,3-tetrabutyl-1,3-dibutyryloxy distannoxane (isomers), 1,1,3,3-tetrabutyl-1,3-divaleryloxy distannoxane (isomers), 1,1,3,3-tetrabutyl-1,3-dilauroyloxy distannoxane (isomers), 1,1,3,3-tetraoctyl-1,3-diacetoxy distannoxane (isomers), 1,1,3,3-tetraoctyl-1,3-dipropionyloxy distannoxane (isomers), 1,1,3,3-tetraoctyl-1,3-dibutyryloxy distannoxane (isomers), 1,1,3,3-tetraoctyl-1,3-divaleryloxy distannoxane (isomers), 1,1,3,3-tetraoctyl-1,3-dilauroyloxy distannoxane (including isomers) or the like; and, 1,1,3,3-tetraalkyl-1,3-dihalide distannoxanes such as 1,1,3,3-tetramethyl-1,3-dichloro distannoxane, 1,1,3,3-tetramethyl-1,3-dibromo distannoxane, 1,1,3,3-tetrabutyl-1,3-dichloro distannoxane (isomers), 1,1,3,3-tetrabutyl-1,3-dibromo distannoxane (isomers), 1,1,3,3-tetraocyl-1,3-dichloro distannoxane (isomers), 1,1,3,3-tetraocyl-1,3-dibromo distannoxane (isomers) or the like.

Among these, 1,1,3,3-tetraalkyl-1,3-dialkoxy distannoxanes such as 1,1,3,3-tetramethyl-1,3-dimethoxy distannoxane, 1,1,3,3-tetramethyl-1,3-diethoxy distannoxane, 1,1,3,3-tetramethyl-1,3-dipropoxy distannoxane (isomers), 1,1,3,3-tetramethyl-1,3-dibutoxy distannoxane (isomers), 1,1,3,3-tetramethyl-1,3-dipentyloxy distannoxane (isomers), 1,1,3,3-tetramethyl-1,3-dihexyloxy distannoxane (isomers), 1,1,3,3-tetramethyl-1,3-diheptyloxy distannoxane (isomers), 1,1,3,3-tetramethyl-1,3-dioctyloxy distannoxane (isomers), 1,1,3,3-tetramethyl-1,3-dinonyloxy distannoxane (isomers), 1,1,3,3-tetramethyl-1,3-didecyloxy distannoxane (isomers), 1,1,3,3-tetrabutyl-1,3-dimethoxy distannoxane (isomers), 1,1,3,3-tetrabutyl-1,3-diethoxy distannoxane (isomers), 1,1,3,3-tetrabutyl-1,3-dipropoxy distannoxane (isomers), 1,1,3,3-tetrabutyl-1,3-dibutoxy distannoxane (isomers), 1,1,3,3- tetrabutyl-1,3-dipentyloxy distannoxane (isomers), 1,1,3,3-tetrabutyl-1,3-dihexyloxy distannoxane (isomers), 1,1,3,3-tetrabutyl-1,3-diheptyloxy distannoxane (isomers), 1,1,3,3-tetrabutyl-1,3-dioctyloxy distannoxane (isomers), 1,1,3,3-tetrabutyl-1,3-dinonyloxy distannoxane (isomers), 1,1,3,3-tetrabutyl-1,3-didecyloxy distannoxane (isomers), 1,1,3,3-tetraoctyl-1,3-dimethoxy distannoxane (isomers), 1,1,3,3-tetraocyl-1,3-diethoxy distannoxane (isomers), 1,1,3,3-tetraoctyl-1,3-dipropoxy distannoxane (isomers), 1,1,3,3-tetraoctyl-1,3-dibutoxy distannoxane (isomers), 1,1,3,3-tetraoctyl-1,3-dipentyloxy distannoxane (isomers), 1,1,3,3-tetraoctyl-1,3-dihexyloxy distannoxane (isomers), 1,1,3,3-tetraoctyl-1,3-diheptyloxy distannoxane (isomers), 1,1,3,3-tetraoctyl-1,3-dioctyloxy distannoxane (isomers), 1,1,3,3-tetraoctyl-1,3-dinonyloxy distannoxane (isomers), 1,1,3,3-tetraoctyl-1,3-didecyloxy distannoxane (isomers) or the like are preferable, and 1,1,3,3-tetrabutyl-1,3-dibutoxy distannoxane (isomers), 1,1,3,3-tetrabutyl-1,3-dipentyloxy distannoxane (isomers), 1,1,3,3-tetrabutyl-1,3-dihexyloxy distannoxane (isomers), 1,1,3,3-tetrabutyl-1,3-diheptyloxy distannoxane (isomers), 1,1,3,3-tetrabutyl-1,3-dioctyloxy distannoxane (isomers), 1,1,3,3-tetraoctyl-1,3-dibutoxy distannoxane (isomers), 1,1,3,3-tetraoctyl-1,3-dipentyloxy distannoxane (isomers), 1,1,3,3-tetraoctyl-1,3-dihexyloxy distannoxane (isomers), 1,1,3,3-tetraoctyl-1,3-diheptyloxy distannoxane (isomers), or the like 1,1,3,3-tetraoctyl-1,3-dioctyloxy distannoxane (including isomers) is more preferable.

Although the monomer structure of the tetraalkyl dialkoxy distannoxane is shown in formula (19), this may also be a polymer structure or aggregate structure.

In general, organic tin compounds easily adopt an aggregate structure, and although, for example, dialkyl tin dialkoxy tin is known to form a dimer structure, and tetraalkyl dialkoxy distannoxanes are known to be present by forming a ladder structure in which two or three molecules are aggregated, even in cases in which there are changes in this aggregated state, the representation of a compound in the form of a monomer structure is common and can be easily understood by a person with ordinary skill in the art.

In addition, the previously indicated dialkyl tin alkoxide compound may be used alone or two or more types may be used as a mixture.

A commercially available product may be used for the dialkyl tin catalyst, or can be produced according to a known method (for example, the method described in U.S. Pat. No. 5,545,600) by reacting an organic tin oxide with at least one compound selected from the group consisting of an alcohol, carboxylic acid, acid anhydride, carbonic acid ester and hydrogen halide followed by removing components containing any water generated from the reaction liquid in the case water is generated.

In the structural formula of this dialkyl tin catalyst, a dialkyl tin oxide represented by the following formula (20) is preferably used for the organic tin oxide:

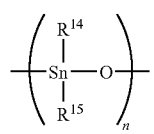

(20)

(wherein each of $R^{14}$ and $R^{15}$ independently represents a linear or branched alkyl group having 1 to 12 carbon atoms).

Examples of $R^{14}$ and $R^{15}$ include alkyl groups in the form of aliphatic hydrocarbon groups having 1 to 12 carbon atoms such as a methyl, ethyl, propyl (isomers), butyl (isomers), pentyl (isomers), hexyl (isomers), heptyl (isomers), octyl (isomers), nonyl (isomers), decyl (isomers), undecyl (isomers), dodecyl (isomers) group or the like, preferably linear or branched saturated alkyl groups having 1 to 8 carbon atoms, and more preferably an n-butyl group or n-octyl group.

Examples of compounds reacted with the organic tin oxide include alcohols in which the number of carbon atoms constituting the alcohol is a number selected from an integer of 1 to 12, such as methanol, ethanol, propanol (isomers), butanol (isomers), pentanol (isomers), hexanol (isomers), heptanol (isomers), octanol (isomers), nonanol (isomers) or decanol (isomers); carboxylic acids in which the number of carbon atoms constituting the carboxylic acid is a number selected from an integer of 1 to 12, such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (isomers), octanoic acid (isomers), nonanoic acid (isomers), decanoic acid (isomers), undecanoic acid (isomers) or dodecanoic acid (isomers); acid anhydrides in which the number of carbons constituting the acid anhydride is a number selected from an integer of 3 to 25, such as acetic anhydride, propionic anhydride, butyric anhydride, isobutyric anhydride, valeric anhydride, isovaleric anhydride, succinic anhydride, maleic anhydride or propionic anhydride; carbonic acid esters such as dimethyl carbonate, diethyl carbonate, dipropyl carbonate (isomers), dibutyl carbonate (isomers), dipentyl carbonate (isomers), dihexyl carbonate (isomers), diheptyl carbonate (isomers) or dioctyl carbonate (isomers); and, hydrogen halides such as hydrogen chloride, hydrogen bromide or the like.

Although varying according to the reacted compounds, in the case the reacted compound is an alcohol and/or a carboxylic acid, although the amount of alcohol is preferably in excess based on the organic tin oxide since the reaction is presumed to be an equilibrium reaction within the range of 2 to 1000 times as the stoichiometric ratio of the alcohol and/or carboxylic acid to the organic tin oxide, in consideration of the size of the reaction vessel, it is preferably within the range of 2 to 100 times and more preferably within the range of 5 to 50 times. As previously described, the reaction is an equilibrium reaction and is preferably carried out while removing any water generated. A known method can be used to remove the water. Examples of such methods for removing water include membrane separation, use of dehydrating agents and distillation. An example of membrane separation involves pervaporation with a hollow fiber, and an organic dehydrating agent or inorganic dehydrating agent can be used for the dehydrating agent. Examples of organic dehydrating agents include acetal compounds, ketal compounds and orthoester compounds, while examples of inorganic dehydrating agents that can be used include a molecular sieve. In the case of using distillation, an alcohol and/or carboxylic acid having a boiling point higher than water at a normal pressure is used for the reacted alcohol described above, and the reaction is preferably carried out while extracting water generated in the reaction outside the system in the form of a gas phase component. The reaction temperature is normally room temperature (20° C.) to 350° C. (for example, 80 to 180° C. in the case the reacted compound is an alcohol), and although a high reaction temperature is preferable for increasing the reaction rate, since there are cases in which undesirable reactions such as decomposition occur at high temperatures thereby decreasing yield, the reaction is preferably carried out within a range of 100 to 160° C. A known cooling apparatus or heating apparatus may be installed in the reaction vessel for the purpose of maintaining a constant reaction temperature. In addition, although varying according to the types of compounds used, reaction temperature and the like, the reaction pressure may be a reduced pressure, a normal pressure or an increased pressure, and the reaction is normally carried out within the range of 20 to $1 \times 10^6$ Pa. There are no particular limitations on the reaction time (residence time in the case of a continuous process), and is normally from 0.001 to 50 hours, preferably from 0.01 to 10 hours and more preferably from 0.1 to 2 hours. In the present embodiments, although it is not necessarily required to use a reaction solvent, a suitable inert solvent can be used for the reaction solvent for the purpose of facilitating the reaction procedure, examples of which include ethers, aliphatic hydrocarbons and aromatic hydrocarbons. A known tank-type reaction vessel, tower-type reaction vessel or distillation column can be used for the reaction vessel, and although known materials can be used for the materials of the reaction vessel and lines provided they do not have a detrimental effect on the starting substances or reacted compounds, materials such as SUS304, SUS316 and SUS316L are inexpensive and can be used preferably.

In the case the reacted compound is an acid anhydride or carbonic acid ester, although a dehydrating agent as mentioned above is not required since this reaction does not result in generation of water, other conditions are the same as in the case of using an alcohol and/or carboxylic acid as described above.

Since the reaction in the case the reacted compound is a hydrogen halide also results in the generation of water, it is preferably carried out while removing the generated water. The hydrogen halide may also be used in a gaseous state, and hydrogen halide in the form of an aqueous solution may also be used. Reaction conditions and reaction temperature are the same as in the case of using an alcohol and/or carboxylic acid as described above.

<Ester Compounds>

Although the dialkyl tin catalyst used in the present embodiments refers to an organic tin compound that demonstrates catalytic action in the production of ester compounds, the term "ester compound" as used in the present embodiments refers to carboxylic acid ester, carbaminic acid ester, isocyanate or carbonic acid ester.

Examples of carboxylic acid esters include aliphatic carboxylic acid esters such as ethyl acetate, propyl acetate (isomers), butyl acetate (isomers), pentyl acetate (isomers), hexyl acetate (isomers), cetyl acetate, vinyl acetate, 2-ethylbutyl acetate, 2-ethylhexyl acetate, 2-hydroxyethyl acetate, 2-methoxyethyl acetate, methylene diacetate, ethylene diacetate, diacetin, triacetin, methyl propionate, ethyl propionate, methyl butyrate, ethyl butyrate, butyl butyrate, isoamyl butyrate, vinyl butyrate, ethyl hexanoate, vinyl hexanoate, ethyl heptanoate, ethyl octanoate, ethyl nonanoate or the like; and aromatic carboxylic acid esters such as methyl benzoate, ethyl benzoate, diethyl benzoate, benzyl benzoate, ethylene dibenzoate, diethyl phthalate or the like.

Examples of carbaminic acid esters include ethyl N-methylcarbamate, diethyl N,N'-ethylidenedicarbamate, ethyl N-acetylcarbamate, N,N'-hexanediyl-bis-carbaminic acid dimethyl ester, N,N'-hexanediyl-bis-carbaminic acid diethyl ester, N,N'-hexanediyl-bis-carbaminic acid dibutyl ester (isomers), N,N'-hexanediyl-bis-carbaminic acid dipentyl ester (isomers), N,N'-hexanediyl-bis-carbaminic acid dihexyl ester (isomers), N,N'-hexanediyl-bis-carbaminic acid dioctyl ester (isomers), N,N'-hexanediyl-bis-carbaminic acid didecyl ester (isomers), N,N'-hexanediyl-bis-carbaminic acid diphenyl ester (isomers), N,N'-hexanediyl-bis-carbaminic acid di(methylphenyl) ester (isomers), N,N'-hexanediyl-bis-carbaminic acid di(ethylphenyl) ester, N,N'-hexanediyl-bis-carbaminic acid-bis-(dimethylphenyl) ester (isomers), N,N'-hexanediyl-bis-carbaminic acid-bis-(dibutylphenyl) ester (isomers), N,N'-hexanediyl-bis-carbaminic acid-bis-(dipentylphenyl) ester (isomers), N,N'-hexanediyl-bis-carbaminic acid-bis-(dioctylphenyl) ester or the like Examples of isocyanic acid esters include ethyl isocyanate, propyl isocyanate (including isomers), butyl isocyanate (isomers), pentyl isocyanate (isomers), hexyl isocyanate (isomers), heptyl isocyanate (isomers), octyl isocyanate (isomers), nonyl isocyanate (isomers), decyl isocyanate (isomers), phenyl isocyanate (isomers), methylphenyl isocyanate (isomers), ethylphenyl isocyanate (isomers), butylphenyl isocyanate (isomers), pentylphenyl isocyanate (isomers), hexylphenyl isocyanate (isomers), dimethylphenyl isocyanate (isomers), diethylphenyl isocyanate (isomers), dibutylphenyl isocyanate (isomers), naphthyl isocyanate (isomers), hexamethylene diisocyanate or the like.

Examples of carbonic acid esters include aliphatic carbonic acid esters such as dimethyl carbonate, diethyl carbonate, dipropyl carbonate (isomers), dibutyl carbonate (isomers), dipentyl carbonate (isomers), dihexyl carbonate (isomers), dipentyl carbonate (isomers), dioctyl carbonate (isomers), dinonyl carbonate (isomers) or the like; and, aromatic carbonic acid esters such as diphenyl carbonate, di(methylphenyl) carbonate (isomers), di(ethylphenyl) carbonate, di(butylphenyl) carbonate (isomers) or the like.

Among these ester compounds, carbonic acid esters are preferable.

In addition, the composition of deactivated forms of the dialkyl tin catalyst formed during the process for producing carbonic acid esters from carbon dioxide and the dialkyl tin catalyst is preferably used for the composition of deactivated forms of the dialkyl tin catalyst in the present embodiments.

<Deactivated Form>

In the present description, the term "deactivated form of dialkyl tin catalyst" is used in relation to the above-mentioned dialkyl tin catalyst, an explanation of this term is provided below.

Deactivated forms of the dialkyl tin catalyst in the present embodiments refer to organic tin compounds generated from the above-mentioned dialkyl tin catalyst that have a structure that differs from said dialkyl tin catalyst, and in which catalytic action in the production of said ester compounds is decreased as compared with the dialkyl tin catalyst.

Deactivated forms of said dialkyl tin catalyst are preferably heat-deactivated forms of the dialkyl tin catalyst. In many cases, the number of alkyl groups bound to the tin atom in such deactivated forms of the dialkyl tin catalyst changes to 0, 1, 3 or 4. Namely, as previously defined, although the dialkyl tin catalyst has two alkyl groups bound to the single tin atom, a deactivated form is an organic tin compound originating from the dialkyl tin catalyst in which the number of alkyl groups bound to the single tin atom has become different from that of the dialkyl tin catalyst. Deactivated forms of dialkyl tin catalysts are presumed to be formed according to a disproportionation reaction shown in the following formula (21) in the case the catalyst is tetraalkyl dialkoxy distannoxane, or according to the following formula (22) in the case the catalyst is a dialkyl tin dialkoxide:

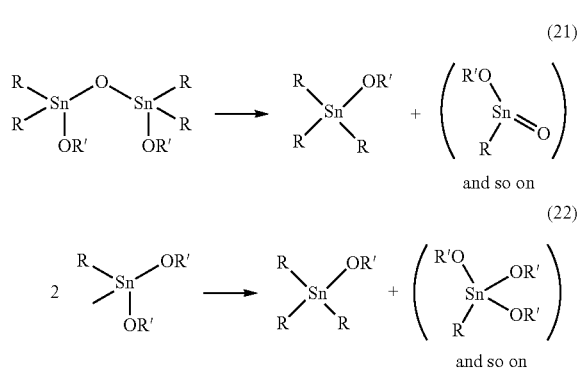

(wherein each of R and R' independently represents a linear or branched alkyl group having 1 to 12 carbon atoms).

Although it is difficult to identify the structures of all deactivated forms of the dialkyl tin catalyst, at least one type of said deactivated forms is a trialkyl tin compound indicated below. For example, there are many cases in which the trialkyl tin compound represented by the following formula (23) is contained in a deactivated dialkyl tin catalyst and is formed at roughly half the amount of said deactivated form in terms of the stoichiometric ratio. The trialkyl tin compound as referred to in the present embodiments refers to an organic tin compound in which three alkyl groups are bound to the tin atom, and said alkyl groups originate in a dialkyl tin catalyst:

(wherein each of $R^{16}$, $R^{17}$, $R^{18}$ and X represent groups originating from the dialkyl tin catalyst, $R^{16}$, $R^{17}$ and $R^{18}$ are selected from $R^1$, $R^2$, $R^3$, $R^4$, $R^5$ and $R^6$, and X is selected from $X^1$, $X^2$, $X^3$ and $X^4$).

Examples of such trialkyl tin compounds include trialkyl-alkoxy tin such as trimethyl-methoxy tin, trimethyl-ethoxy tin, trimethyl-propoxy tin (isomers), trimethyl-butoxy tin (isomers), trimethyl-pentyloxy tin (isomers), trimethyl-hexyloxy tin (isomers), trimethyl-heptyloxy tin (isomers), trimethyl-octyloxy tin (isomers), butyl-dimethyl-methoxy tin (isomers), butyl-dimethyl-ethoxy tin (isomers), butyl-dimethyl-propoxy tin (isomers), butyl-dimethyl-butoxy tin (isomers), butyl-dimethyl-pentyloxy tin (isomers), butyl-dimethyl-hexyloxy tin (isomers), butyl-dimethyl-heptyloxy tin (isomers), butyl-dimethyl-octyloxy tin (isomers), butyl-dimethyl-nonyloxy tin (isomers), butyl-dimethyl-decyloxy tin (isomers), dibutyl-methyl-methoxy tin (isomers), dibutyl-methyl-ethoxy tin (isomers), dibutyl-methyl-propoxy tin (isomers), dibutyl-methyl-butoxy tin (isomers), dibutyl-methyl-pentyloxy tin (isomers), dibutyl-methyl-hexyloxy tin (isomers), dibutyl-methyl-heptyloxy tin (isomers), dibutyl-methyl-octyloxy tin (isomers), butyl-diethyl-methoxy tin (isomers), butyl-diethyl-ethoxy tin (isomers), butyl-diethyl-propoxy tin (isomers), butyl-diethyl-butoxy tin (isomers), butyl-diethyl-pentyloxy tin (isomers), butyl-diethyl-hexyloxy tin (isomers), butyl-diethyl-heptyloxy tin (isomers), butyl-diethyl-octyloxy tin (isomers), dibutyl-ethyl-methoxy tin (isomers), dibutyl-ethyl-ethoxy tin (isomers), dibutyl-ethyl-propoxy tin (isomers), dibutyl-ethyl-butoxy tin (isomers), dibutyl-ethyl-pentyloxy tin (isomers), dibutyl-ethyl-hexyloxy tin (isomers), dibutyl-ethyl-heptyloxy tin (isomers), dibutyl-ethyl-octyloxy tin (isomers), butyl-dipropyl-methoxy tin (isomers), butyl-dipropyl-ethoxy tin (isomers), butyl-dipropyl-propoxy tin (isomers), butyl-dipropyl-butoxy tin (isomers), butyl-dipropyl-pentyloxy tin (isomers), butyl-dipropyl-hexyloxy tin (isomers), butyl-dipropyl-heptyloxy tin (isomers), butyl-dipropyl-octyloxy tin (isomers), dibutyl-propyl-methoxy tin (isomers), dibutyl-propyl-ethoxy tin (isomers), dibutyl-propyl-propoxy tin (isomers), dibutyl-propyl-butoxy tin (somers), dibutyl-propyl-pentyloxy tin (isomers), dibutyl-propyl-hexyloxy tin (isomers), dibutyl-propyl-heptyloxy tin (isomers), dibutyl-propyl-octyloxy tin (isomers), tributyl-methoxy tin (isomers), tributyl-ethoxy tin (isomers), tributyl-propoxy tin (isomers), tributyl-butoxy tin (isomers), tributyl-pentyloxy tin (isomers), tributyl-hexyloxy tin (isomers), tributyl-heptyloxy tin (isomers), tributyl-octyloxy tin (isomers), octyl-dimethyl-methoxy tin (isomers), octyl-dimethyl-ethoxy tin (isomers), octyl-dimethyl-propoxy tin (isomers), octyl-dimethyl-butoxy tin (isomers), octyl-dimethyl-pentyloxy tin (isomers), octyl-dimethyl-hexyloxy tin (isomers), octyl-dimethyl-heptyloxy tin (isomers) octyl-dimethyl-octyloxy tin (isomers), octyl-dimethyl-nonyloxy tin (isomers), octyl-dimethyl-decyloxy tin (isomers), dioctyl-methyl-methoxy tin (isomers), dioctyl-methyl-ethoxy tin (isomers), dioctyl-methyl-propoxy tin (isomers), dioctyl-methyl-butoxy tin (isomers), dioctyl-methyl-pentyloxy tin (isomers), dioctyl-methyl-hexyloxy tin (isomers), dioctyl-methyl-heptyloxy tin (isomers), dioctyl-methyl-octyloxy tin (isomers), octyl-diethyl-methoxy tin (isomers), octyl-diethyl-ethoxy tin (isomers), octyl-diethyl-propoxy tin (isomers), octyl-diethyl-butoxy tin (isomers), octyl-diethyl-pentyloxy tin (isomers), octyl-diethyl-hexyloxy tin (isomers), octyl-diethyl-heptyloxy tin (isomers), octyl-diethyl-octyloxy tin (isomers), dioctyl-ethyl-methoxy tin (isomers), dioctyl-ethyl-ethoxy tin (isomers), dioctyl-ethyl-propoxy tin (isomers), dioctyl-ethyl-butoxy tin (isomers), dioctyl-ethyl-pentyloxy tin (isomers), dioctyl-ethyl-hexyloxy tin (isomers), dioctyl-ethyl-heptyloxy tin (isomers), dioctyl-ethyl-octyloxy tin (isomers), octyl-dipropyl-methoxy tin (isomers), octyl-dipropyl-ethoxy tin (isomers), octyl-dipropyl-propoxy tin (isomers), octyl-dipropyl-butoxy tin (isomers), octyl-dipropyl-pentyloxy tin (isomers), octyl-dipropyl-hexyloxy tin (isomers), octyl-dipropyl-heptyloxy tin (isomers), octyl-dipropyl-octyloxy tin (isomers), dioctyl-propyl-methoxy tin (isomers), dioctyl-propyl-ethoxy tin (isomers), dioctyl-propyl-propoxy tin (isomers), dioctyl-propyl-butoxy tin (isomers), dioctyl-propyl-pentyloxy tin (isomers), dioctyl-propyl-hexyloxy tin (isomers), dioctyl-propyl-heptyloxy tin (isomers), dioctyl-propyl-octyloxy tin (isomers), octyl-dibutyl-methoxy tin (isomers), octyl-dibutyl-ethoxy tin (isomers), octyl-dibutyl-propoxy tin (isomers), octyl-dibutyl-butoxy tin (isomers), octyl-dibutyl-pentyloxy tin (isomers), octyl-dibutyl-hexyloxy tin (isomers), octyl-dibutyl-heptyloxy tin (isomers), octyl-dibutyl-octyloxy tin (isomers), dioctyl-butyl-methoxy tin (isomers), dioctyl-butyl-ethoxy tin (isomers), dioctyl-butyl-propoxy tin (isomers), dioctyl-butyl-butoxy tin (isomers), dioctyl-butyl-pentyloxy tin (isomers), dioctyl-butyl-hexyloxy tin (isomers), dioctyl-butyl-heptyloxy tin (isomers), dioctyl-butyl-octyloxy tin (isomers), trioctyl-methoxy tin (isomers), trioctyl-ethoxy tin (isomers), trioctyl-propoxy tin (isomers), trioctyl-butoxy tin (isomers), trioctyl-pentyloxy tin (isomers), trioctyl-hexyloxy tin (isomers), trioctyl-heptyloxy tin (isomers), rioctyl-octyloxy tin (isomers) or the like; trialkyl-acyloxy tin such as trimethyl-acetoxy tin, trimethyl-propionyloxy tin (isomers), trimethyl-butyryloxy tin (isomers), trimethyl-valeryloxy tin (isomers), trimethyl-lauroyloxy tin (isomers), butyl-dimethyl-acetoxy tin (isomers), butyl-dimethyl-propionyloxy tin (isomers), butyl-dimethyl-butyryloxy tin (isomers), butyl-dimethyl-valeryloxy tin (isomers), butyl-dimethyl-lauroyloxy tin (isomers), dibutyl-methyl-acetoxy tin (isomers), dibutyl-methyl-propionyloxy tin (isomers), dibutyl-methyl-butyryloxy tin (isomers), dibutyl-methyl-valeryloxy tin (isomers), dibutyl-methyl-lauroyloxy tin (isomers), butyl-diethyl-acetoxy tin (isomers), butyl-diethyl-propionyloxy tin (isomers), butyl-diethyl-butyryloxy tin (isomers), butyl-diethyl-valeryloxy tin (isomers), butyl-diethyl-lauroyloxy tin (isomers), dibutyl-ethyl-acetoxy tin (isomers), dibutyl-ethyl-propionyloxy tin (isomers), dibutyl-ethyl-butyryloxy tin (isomers), dibutyl-ethyl-valeryloxy tin (isomers), dibutyl-ethyl-lauroyloxy tin (isomers), butyl-dipropyl-acetoxy tin (isomers), butyl-dipropyl-propionyloxy tin (isomers), butyl-dipropyl-butyryloxy tin (isomers), butyl-dipropyl-valeryloxy tin (isomers), butyl-dipropyl-lauroyloxy tin (isomers), dibutyl-propyl-acetoxy tin (isomers), dibutyl-propyl-propionyloxy tin (isomers), dibutyl-propyl-butyryloxy tin (isomers), dibutyl-propyl-valeryloxy tin (isomers), dibutyl-propyl-lauroyloxy tin (isomers), tributyl-acetoxy tin (isomers), tributyl-propionyloxy tin (isomers), tributyl-butyryloxy tin (isomers), tributyl-valeryloxy tin (isomers), tributyl-lauroyloxy tin (isomers), octyl-dimethyl-acetoxy tin (isomers), octyl-dimethyl-propionyloxy tin (isomers), octyl-dimethyl-butyryloxy tin (isomers), octyl-dimethyl-valeryloxy tin (isomers), octyl-dimethyl-lauroyloxy tin (isomers), dioctyl-methyl-acetoxy tin (isomers), dioctyl-methyl-propionyloxy tin (isomers), dioctyl-methyl-butyryloxy tin (isomers), dioctyl-methyl-valeryloxy tin (isomers), dioctyl-methyl-lauroyloxy tin (isomers), octyl-diethyl-acetoxy tin (isomers), octyl-diethyl-propionyloxy tin (isomers), octyl-diethyl-butyryloxy tin (isomers), octyl-diethyl-valeryloxy tin (isomers), octyl-diethyl-lauroyloxy tin (isomers), dioctyl-ethyl-acetoxy tin (isomers), dioctyl-ethyl-propionyloxy tin (isomers), dioctyl-ethyl-butyryloxy tin (isomers), dioctyl-ethyl-valeryloxy tin (isomers), dioctyl-ethyl-lauroyloxy tin (isomers), octyl-dipropyl-acetoxy tin (isomers), octyl-dipropyl-propionyloxy tin (isomers), octyl-dipropyl-butyryloxy tin (isomers), octyl-dipropyl-valeryloxy tin (isomers), octyl-dipropyl-lauroyloxy tin (isomers), dioctyl-propyl-acetoxy tin (isomers), dioctyl-propyl-propionyloxy tin (isomers), dioctyl-propyl-butyryloxy tin (isomers), dioctyl-propyl-valeryloxy tin (isomers), dioctyl-propyl-lauroyloxy tin (isomers), trioctyl-acetoxy tin (isomers), trioctyl-propionyloxy tin (isomers), trioctyl-butyryloxy tin (isomers), trioctyl-valeryloxy tin (isomers), trioctyl-lauroyloxy tin (including isomers) or the like; and, trialkyl halide tin such as trimethylchloro tin, trimethylbromo tin, butyl-dimethylchloro tin, butyl-dimethylchloro tin (isomers), dibutyl-methylchloro tin (isomers), dibutyl-methylbromo tin (isomers), butyl-diethylchloro tin (isomers), butyl-diethylbromo tin (isomers), dibutyl-ethylchloro tin (isomers), dibutyl-ethylbromo tin (isomers), butyl-dipropylchloro tin (isomers), butyl-dipropylbromo tin (isomers), dibutyl-propylchloro tin (isomers), dibutyl-propylbromo tin (isomers), tributylchloro tin (isomers), tributylbromo tin (isomers), octyl-dimethylchloro tin (isomers), octyl-dimethylbromo tin (isomers), dioctyl-methylchloro tin (isomers), dioctyl-methylbromo tin (isomers), octyl-diethylchloro tin (isomers), octyl-diethylbromo tin (isomers), dioctyl-ethylchloro tin (isomers), dioctyl-ethylbromo tin (isomers), octyl-dipropylchloro tin (isomers), octyl-dipropylbromo tin (isomers), dioctyl-propylchloro tin (isomers), dioctyl-propylbromo tin (isomers), trioctylchloro tin (isomers), trioctylbromo tin (isomers) or the like.

In addition to the trialkyl tin compound represented by the above-mentioned formula (23), tin components having a high boiling point (for example, 250° C. or higher at 50 Pa) and unidentifiable structure are included in the deactivated forms of the dialkyl tin catalyst. Such tin components having the high boiling point and unidentifiable structure can be characterized by the chemical shift thereof in $^{119}$Sn-NMR spectrum. Namely, at least one deactivated form of the dialkyl tin catalyst is an organic tin compound having a tin atom that demonstrates a chemical shift at from −220 to −610 ppm based on tetramethyl tin when analyzed by $^{119}$Sn-NMR in a heavy chloroform solution. In other words, deactivated forms of the dialkyl tin catalyst are trialkyl tin compounds (the trialkyl tin compounds used herein refer to organic tin compounds in which three alkyl groups are bound to the tin atom and said alkyl groups are alkyl groups originating from the dialkyl tin catalyst) and organic tin compounds containing a tin atom that demonstrates a chemical shift at from −220 to −610 ppm based on tetramethyl tin when analyzed by $^{119}$Sn-NMR in a heavy chloroform solution.

The dialkyl tin catalyst represented by formula (7) and/or formula (8) has a tin atom that demonstrates a chemical shift at from 200 to −200 ppm based on tetramethyl tin when analyzed by $^{119}$Sn-NMR in a heavy chloroform solution, and as a result of the dialkyl tin catalyst being deactivated by denaturation, a tin component is detected that has the tin atom demonstrating a chemical shift within the above-mentioned range. Since the composition of deactivated forms has a plurality of signals within said range of from −220 to −610 ppm in nearly all cases, not only the monoalkylalkoxy tin oxide and monoalkyl-trialkoxy tin represented by formula (21) and/or formula (22), but also other structures are presumed to be contained in the composition of deactivated forms in the majority of cases. However, although the composition of deactivated forms is composed of compounds having an indeterminate structure in this manner, it was surprisingly found that the use of the process of the present embodiments enables the production of the dialkyl tin compound, thereby leading to completion of the present invention.

As described above, the detailed structures of the deactivated forms of the dialkyl tin catalyst containing the tin atom characterized by chemical shift in $^{119}$Sn-NMR are unclear. On the other hand, since trialkyl tin compounds are contained in the deactivated forms as previously described, monoalkyl tin compounds, for example, can be assumed to be contained as shown in formula (21) and/or formula (22) in consideration of alkyl group balance. Herein, monoalkyl tin compounds are organic tin compounds in which one alkyl group originating from the dialkyl tin catalyst is bound to a single tin atom. Examples of monoalkyl tin compounds include monoalkylalkoxy tin oxides such as methyl-methoxy tin oxide, methyl-ethoxy tin oxide, methyl-propoxy tin oxide (isomers), methyl-butoxy tin oxide (isomers), methyl-pentyloxy tin oxide (isomers), methyl-hexyloxy tin oxide (isomers), methyl-heptyloxy tin oxide (isomers), methyl-octyloxy tin oxide (isomers), butyl-methoxy tin oxide (isomers), butyl-ethoxy tin oxide (isomers), butyl-propoxy tin oxide (isomers), butyl-butoxy tin oxide (isomers), butyl-pentyloxy tin oxide (isomers), butyl-hexyloxy tin oxide (isomers), butyl-heptyloxy tin oxide (isomers), butyl-octyloxy tin oxide (isomers), octyl-methoxy tin oxide (isomers), octyl-ethoxy tin oxide (isomers), octyl-propoxy tin oxide (isomers), octyl-butoxy tin oxide (isomers), octyl-pentyloxy tin oxide (isomers), octyl-hexyloxy tin oxide (isomers), octyl-heptyloxy tin oxide (isomers), octyl-octyloxy tin oxide (isomers) or the like; monoalkyl-trialkoxy tin such as methyl-trimethoxy tin, methyl-triethoxy tin, methyl-tripropoxy tin (isomers), methyl-tributoxy tin (isomers), methyl-tripentyloxy tin (isomers), methyl-trihexyloxy tin (isomers), methyl-triheptyloxy tin (isomers), methyl-trioctyloxy tin (isomers), butyl-trimethoxy tin (isomers), butyl-triethoxy tin (isomers), butyl-tripropoxy tin (isomers), butyl-tributoxy tin (isomers), butyl-tripentyloxy tin (isomers), butyl-trihexyloxy tin (isomers), butyl-triheptyloxy tin (isomers), butyl-trioctyloxy tin (isomers), octyl-trimethoxy tin (isomers), octyl-triethoxy tin (isomers), octyl-tripropoxy tin (isomers), octyl-tributoxy tin (isomers), octyl-tripentyloxy tin (isomers), octyl-trihexyloxy tin (isomers), octyl-triheptyloxy tin (isomers), octyl-trioctyloxy tin (isomers) or the like; monoalkyl-acyloxy tin oxide such as methyl-acetoxy tin oxide, methyl-propionyloxy tin oxide (isomers), methyl-butyryloxy tin oxide (isomers), methyl-valeryl tin oxide (isomers), methyl-lauroyloxy tin oxide (isomers), butyl-acetoxy tin oxide, butyl-propionyloxy tin oxide (isomers), butyl-butyryloxy tin oxide (isomers), butyl-valeryloxy tin oxide (isomers), butyl-lauroyloxy tin oxide (isomers), octyl-acetoxy tin oxide (isomers), octyl-propionyloxy tin oxide (isomers), octyl-butyryloxy tin oxide (isomers), octyl-valeryloxy tin oxide (isomers), octyl-lauroyloxy tin oxide (isomers) or the like; monoalkyl-triacyloxy tin such as methyl-triacetoxy tin, methyl-tripropionyloxy tin (isomers), methyl-tributyryloxy tin (isomers), methyl-trivaleryloxy tin (isomers), methyl-trilauroyloxy tin (isomers), butyl-triacetoxy tin (isomers), butyl-tripropionyloxy tin (isomers), butyl-tributyryloxy tin (isomers), butyl-trivaleryloxy tin (isomers), butyl-trilauroyloxy tin (isomers), octyl-triacetoxy tin (isomers), octyl-tripropionyloxy tin (isomers), octyl-tributyryloxy tin (isomers), octyl-trivaleryloxy tin (isomers), octyl-trilauroyloxy tin (isomers) or the like; and, monoalkyl halide tin oxides such as methylchloro tin oxide, methylbromo tin oxide, butylchloro tin oxide, butylbromo tin oxide, octylchloro tin oxide, octylbromo tin oxide or the like.

The structures of the deactivated forms of the dialkyl tin catalyst can be easily presumed to adopt structures other than the examples listed above. Moreover, compounds may also be formed with a unit in which two alkyl groups are bound to tin and a unit in which an integral number of alkyl groups other than two are bound to tin (deactivated form component units) as a result of forming a stannoxane backbone. The structures of presumed deactivated forms and/or deactivated forms containing deactivated form component units are shown below together with the above-mentioned examples:

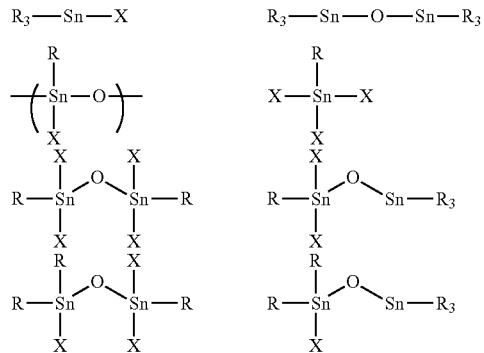

(wherein, R and X are groups originating from the dialkyl tin catalyst, R is selected from $R^1$, $R^2$, $R^3$, $R^4$, $R^5$ and $R^6$, and X is selected from $X^1$, $X^2$, $X^3$ and $X^4$).

The composition of deactivated forms of the dialkyl tin catalyst as referred to in the present embodiments refers to a composition containing the aforementioned deactivated forms. Namely, this may a mixture of the dialkyl tin catalyst and deactivated forms of said dialkyl tin catalyst, or a composition comprising only the deactivated forms. In addition, it may also be a component in which a deactivated form (namely an organic tin compound originating from the dialkyl tin catalyst in which the number of alkyl groups bound to a single tin atom differs from that of the dialkyl tin catalyst) and a component in which the number of alkyl groups bound to a single tin atom is two are covalently bonded as previously described. A composition of deactivated forms able to be preferably used in the present embodiments refers to a composition of deactivated forms having a content as mol % of deactivated forms in which the number of alkyl groups bound to the tin atom of an alkyl tin compound is a number other than two of 10 mol % or more, preferably 30 mol % or more and more preferably 50 mol % or more based on the total number of moles of tin atoms of alkyl tin compounds contained in a composition of deactivated forms of the dialkyl tin catalyst, and said deactivated forms are accumulated and/or concentrated.

Although the dialkyl tin catalyst, tetraalkyl tin, tin oxide ($SnO_2$) and the like may be contained in the composition of deactivated forms of the dialkyl tin catalyst depending on the case, these compounds may be contained to a degree that does not violate the purport of the present invention.

In addition, an alkyl redistribution reaction and/or dealkylation reaction to be described later can also be carried out using a composition containing the trialkyl tin compounds, and a compound containing compounds containing the tin atom that demonstrates a chemical shift at from –220 to –610 ppm based on tetramethyl tin when analyzed by $^{119}$Sn-NMR in a heavy chloroform solution, is separated from a composition of deactivated forms of a dialkyl tin catalyst.

At least one method selected from distillation separation, extraction separation and membrane separation can be used as a method for separating the composition containing the trialkyl tin compounds and the composition containing compounds containing the tin atom that demonstrates a chemical shift at from –220 to –610 ppm based on tetramethyl tin when analyzed by $^{119}$Sn-NMR in a heavy chloroform solution from the composition of deactivated forms of the dialkyl tin catalyst, and distillation separation is used particularly preferably.

<Composition of Deactivated Forms of Dialkyl Tin Catalyst>

A composition of deactivated forms of the dialkyl tin catalyst obtained during the process for producing carbonic acid ester using the dialkyl tin catalyst, and particularly a composition containing deactivated forms of the dialkyl tin alkoxide catalyst obtained in during the process for producing carbonic acid ester by the reaction between the dialkyl tin alkoxide catalyst and carbon dioxide, can be used for the composition of deactivated forms of a dialkyl tin catalyst used in the present embodiments. Herein, the dialkyl tin alkoxide catalyst refers to the previously described dialkyl-dialkoxy tin and/or tetraalkyl dialkoxy distannoxane, and preferably a compound is used selected from at least one type of compound selected from the group consisting of the dialkyl tin compound represented by the above-mentioned formula (7) and the tetraalkyl distannoxane compound represented by the above-mentioned formula (8) wherein $X^1$ and $X^2$ of formula (7) and $X^3$ and $X^4$ of formula (8) are alkoxy groups. The following indicates an example of the process for producing carbonic acid ester in this manner.

First, the dialkyl tin dialkoxide catalyst is contacted with carbon dioxide at a stoichiometric ratio of 1 to 50 based on the dialkyl tin dialkoxide catalyst within a pressure range of from normal pressure to 200 MPa to form a carbon dioxide addition form of the dialkyl tin dialkoxide catalyst. Next, the carbon dioxide addition form of the dialkyl tin dialkoxide catalyst is subjected to thermal decomposition within a temperature range of from 20 to 300° C. and time range of from 10 minutes to 500 hours to obtain a mixture containing carbonic acid ester, dialkyl tin alkoxide catalyst and deactivated forms of the dialkyl tin alkoxide catalyst. In the present embodiments, this mixture of carbonic acid ester, dialkyl tin alkoxide catalyst and deactivated forms of the dialkyl tin alkoxide catalyst may be used as a composition of deactivated forms of the dialkyl tin catalyst. In addition, a mixture containing carbonic acid ester, dialkyl tin alkoxide catalyst and deactivated forms of the dialkyl tin alkoxide catalyst, obtained by removing all or a portion of the carbonic acid ester from said mixture by a method such as filtration, solvent extraction, distillation or membrane separation, can also be used as the composition of deactivated forms of the dialkyl tin catalyst.

Moreover, the portion remaining following recovery of the dialkyl tin dialkoxide catalyst from the mixture containing dialkyl tin dialkoxide catalyst produced by reacting carbonic acid ester with the composition of deactivated forms of the dialkyl tin catalyst obtained during the process for producing carbonic acid ester by reacting the dialkyl tin alkoxide catalyst and carbon dioxide as previously disclosed by the inventors of the present invention (see International Publication No. WO 2007/097388) can also be used for the composition of deactivated forms of the dialkyl tin catalyst in the present embodiments.

<Alkyl Group Redistribution Reaction>

The following provides an explanation of the alkyl group redistribution reaction in the present embodiments.

The alkyl group redistribution reaction in the present embodiments is a reaction in which two or more types of different organic tin compounds, in which the number of alkyl groups bound to a single tin atom is two or more, are reacted to average the number of alkyl groups bound to a single tin atom, and said alkyl redistribution reaction is an equilibrium reaction. Although the details of the reaction mechanism are unclear, it is presumed as a result of an organic tin compound having three alkyl groups bound to a single tin atom reacting with an organic tin compound in which one alkyl group is bound to a single tin atom, organic tin compounds are formed in which the number of alkyl groups bound to a single tin atom is two as in the following formula (24):

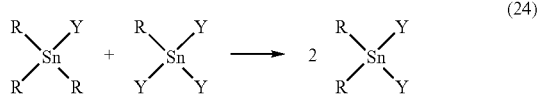

(wherein R represents a linear or branched alkyl group having 1 to 12 carbon atoms, and Y represents a group other than an alkyl group).

This alkyl group redistribution reaction proceeds as a result of heat treatment of a mixture of two or more types of organic compounds in which the difference of the numbers of alkyl groups which are bound to a single tin atom is two or more.

This heat treatment is preferably carried out at a temperature range of from 20 to 300° C., and in the case of desiring to accelerate the reaction or obtain a higher concentration of the dialkyl form, it is advantageous to raise the reaction temperature to more preferably from 50 to 280° C. to shift the equilibrium to the right. Although a high heat treatment temperature is preferable to increase the reaction rate, since undesirable reactions such as decomposition and the like also occur at high temperatures thereby causing a decrease in yield, the reaction is even more preferably carried out at a temperature range of from 80 to 260° C. The reaction time may become excessively long if the temperature is lower than 20° C., while the yield of dialkyl tin compound may decrease due to denaturation of the organic tin compounds caused by decomposition and the like at a temperature higher than 300° C. Although varying according to the compounds used and heat treatment time, the reaction time is from 0.001 to 50 hours and preferably from 0.01 to 10 hours, and in consideration of industrial productivity, the reaction time is set to from 0.1 to 2 hours. The reaction may be terminated when the desired dialkyl tin compound is obtained as determined by $^{119}$Sn-NMR and the like. As will be described later, since the alkyl group redistribution reaction of the present embodiments is presumed to be an equilibrium reaction, in order to obtain a higher concentration of tin compound in which the number of alkyl groups bound to a single tin atom is two, the reaction is carried out within a concentration range such that the concentration of products is higher than the reactants by measuring the equilibrium concentrations of the compounds used versus temperature, or so that the concentration of dialkyl tin compound of the products increases by converting substituents using a method to be described later. In addition, in the case of heat treating at a high temperature (for example, 150° C. or higher), there are cases in which the yield of dialkyl tin compound decreases if an excessive amount of time is required for cooling. This is because the reaction system attempts to approach the equilibrium concentration at a low temperature during the course of cooling, and it is therefore preferable to cool rapidly following heat treatment at a high temperature. A known method can be preferably used for the method for cooling the reaction liquid, and for example, a method by use of brine or a method comprising flushing into a low-pressure reaction vessel from the heat treatment tank can be used preferably.

This alkyl group redistribution reaction can also be carried out in the presence or absence of a metal halide catalyst. Examples of metal halide catalysts include tin (II) chloride, mercury (II) chloride, lead (II) chloride, mercury (II) fluoride, lead (II) fluoride, tin (II) fluoride, tin (II) iodide, lead (II) iodide, mercury (II) iodide, tin (II) bromide, mercury (II) bromide, lead (II) bromide or the like, and these metal halides can be used alone or two or more types can be used as a mixture. These metal halides can be preferably used within the range of from 0.1 to 10% by weight based on the solution used for heat treatment.

Although the use of a solvent is not required for said alkyl group redistribution reaction, a solvent can be used for the purpose of improving fluidity or facilitating the reaction procedure. Examples of such solvents include linear, branched or cyclic hydrocarbons having 5 to 16 carbon atoms, ethers composed of linear, branched or cyclic hydrocarbons having 4 to 16 carbon atoms and linear, branched or cyclic halogenated hydrocarbons having 1 to 16 carbon atoms. Specific examples include linear and cyclic hydrocarbons selected from pentane (isomers), hexane (isomers), heptane (isomers), octane (isomers), nonane (isomers), decane (isomers), hexadecane (isomers), cyclohexane, cycloheptane, cyclooctane, benzene, toluene, xylene (isomers), ethylbenzene or the like; ethers selected from diethyl ether, dipropyl ether (isomers), dibutyl ether (isomers), dihexyl ether (isomers), dioctyl ether (isomers), diphenyl ether or the like; and, halogenated hydrocarbons selected from methylene chloride, chloroform, carbon tetrachloride, chlorobenzene, tetrachloroethane, dichlorobenzene (isomers) or the like. These solvents can be used alone or two or more types can be used as a mixture. Solvents can be used for the purpose of improving fluidity, facilitating the reaction procedure, or efficiently removing water outside the system in the case said water is generated in the reaction. Examples of such solvents include linear, branched or cyclic hydrocarbons having 5 to 16 carbons, ethers composed of linear, branched or cyclic hydrocarbons having 4 to 16 carbon atoms and linear, branched or cyclic halogenated hydrocarbons having 1 to 16 carbon atoms. Specific examples include linear and cyclic hydrocarbons selected from pentane (isomers), hexane (isomers), heptane (isomers), octane (isomers), nonane (isomers), decane (isomers), hexadecane (isomers), cyclohexane, cycloheptane, cyclooctane, benzene, toluene, xylene (isomers), ethylbenzene or the like; ethers selected from diethyl ether, dipropyl ether (isomers), dibutyl ether (isomers), dihexyl ether (isomers), dioctyl ether (isomers), diphenyl ether or the like; and, halogenated hydrocarbons selected from methylene chloride, chloroform, carbon tetrachloride, chlorobenzene, tetrachloroethane, dichlorobenzene (isomers) or the like. These solvents can be used alone or two or more types can be used as a mixture.

In addition, a dialkyl tin compound may also be obtained by carrying out a dealkylation reaction to be described later simultaneous to said alkyl group redistribution reaction.

As previously described, said alkyl group redistribution reaction is presumed to be an equilibrium reaction. As a result of extensive studies conducted by the inventors of the present invention, it was surprisingly found that whether this equilibrium is biased towards the reactants or products is dependent upon substituents bound to the tin atom and/or the temperature at which said alkyl group redistribution reaction is carried out. In terms of substituents bound to the tin atom, with respect to, for example, an alkyl group other than alkyl groups originating from the dialkyl tin catalyst bound to the tin atom, in the case the pKa of the conjugated acid of said group is 0 to 6.8, equilibrium was determined to be biased toward the products in the majority of cases, while conversely in the case the pKa of the conjugated acid of said group is 6.8 to 25, the equilibrium was determined to be biased toward the reactants in the majority of cases. In addition, in the case the pKa of the conjugated acid is 0 to 6.8, the equilibrium was found to be biased toward the products side as temperature increases.

Namely, on the basis of the above finding, the inventors of the present invention conceived of a method for regenerating a dialkyl tin compound from deactivated forms of the dialkyl tin catalyst (or causing redistribution of alkyl groups), thereby leading to completion of the present invention. In the case deactivated forms of the dialkyl tin catalyst have Sn—Y bonds, a dialkyl tin compound can be produced by heat-treating the deactivated forms of the dialkyl tin catalyst. Here, Y represents a Y in which the pKa of HY, which is a conjugated acid of Y in which a hydrogen atom has been added to Y, is 0 to 6.8.

On the other hand, in the case the deactivated forms of the dialkyl tin catalyst do not have Sn—Y bonds, namely in the case the pKa of a conjugated acid of a group other than the alkyl group originating from the dialkyl tin catalyst bound to the tin atom of the deactivated forms of the dialkyl tin catalyst is 6.9 to 25, a dialkyl tin compound can be produced by carrying out step (A) described below prior to heat treatment.

Step (A): (Substituent conversion step) All of a portion of those substituents of said deactivated forms excluding alkyl groups originating from the dialkyl tin catalyst are converted to a substituent Y to obtain an organic tin compound having an Sn—Y bond.

Here, Y represents a Y in which the pKa of HY, which is a conjugated acid of Y in which a hydrogen atom has been added to Y, is 0 to 6.8.

The following provides an explanation of step (A).

Step (A) is a step in which a composition of deactivated forms of the dialkyl tin catalyst are reacted with an acid represented by the following formula (25) and/or an acid anhydride represented by the following formula (26) to produce an organic tin compound having an Sn—Y bond in which three alkyl groups and one Y group originating from the acid and/or acid anhydride are bound to a single tin atom, and an organic tin compound having an Sn—Y bond in which one alkyl group and a number of Y groups originating from the acid and/or acid anhydride, the number of Y groups being selected from an integer of 1 to 3, are bound to a single tin atom.

As previously described, an acid represented by the following formula (25) is preferably used for the acid:

$$HY \tag{25}$$

(wherein Y represents Y in which the pKa of a conjugated acid of Y in the form of HY, in which a hydrogen atom has been added to Y, is 0 to 6.8).

An organic acid or inorganic acid may be used for this acid. Examples of inorganic acids that can be used include hydrogen halides, hydrohalic acids, sulfuric acid, nitric acid, phosphoric acid, carbonic acid or the like, while hydrogen halides are used preferably and hydrogen chloride is used more preferably. Examples of organic acids that can be used include carboxylic acids, sulfonic acids, sulfinic acids, phenols, enols, thiophenols, imides, oxime, aromatic sulfonamides or the like, while carboxylic acids, sulfonic acids, sulfinic acids and phenols are used preferably, and carboxylic acids are used more preferably. Examples of carboxylic acids include saturated or unsaturated aliphatic monocarboxylic acid compounds such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (isomers), octanoic acid (isomers), nonaoic acid (isomers), decanoic acid (isomers), undecanoic acid (isomers), dodecanoic acid (isomers), tetradecanoic acid (isomers), hexadecanoic acid (isomers), acrylic acid, crotic acid, isocrotic acid, vinylacetic acid, methacrylic acid, angelic acid, tiglic acid, allylacetic acid, undecenoic acid (isomers) or the like; saturated or unsaturated aliphatic dicarboxylic acids such as oxalic acid, malonic acid, succinic acid, glutaric acid, adipic acid, heptanedioic acid (isomers), octanedioic acid (isomers), nonanedioic acid (isomers), decanedioic acid (isomers), maleic acid, fumaric acid, methylmaleic acid, methylfumaric acid, pentenedioic acid (isomers), itaconic acid, allylmalonic acid or the like; saturated or unsaturated aliphatic tricarboxylic acids such as 1,2,3-propanetricarboxylic acid, 1,2,3-propenetricarboxylic acid, 2,3-dimethylbutane-1, 2,3-tricarboxylic acid or the like; aromatic carboxylic acid compounds such as benzoic acid, methylbenzoic acid (isomers), ethylbenzoic acid (isomers), propylbenzoic acid (isomers), dimethylbenzoic acid (isomers), trimethylbenzoic acid (isomers) or the like; aromatic dicarboxylic acid compounds such as phthalic acid, isophthalic acid, terephthalic acid, methylisophthalic acid (isomers) or the like; and, aromatic tricarboxylic acid compounds such as hemimellitic acid, trimellitic acid, trimesic acid or the like. Among these carboxylic acids, saturated monocarboxylic acids are used preferably, while saturated monocarboxylic acids having a standard boiling point of 300° C. or lower are used more preferably, and saturated monocarboxylic acids having a standard boiling point of 250° C. or lower are used even more preferably. Standard boiling point refers to the boiling point at 1 atmosphere as described in Encyclopedia Chimica (published on Oct. 1, 2003 by Kyoritsu Publishing Co., Ltd.).

More specifically, acetic acid, propionic acid, n-butyric acid, isobutyric acid, valeric acid, isovaleric acid, 2-methylbutanoic acid, pivalic acid and hexanoic acid are used preferably.

An acid anhydride represented by the following formula (26) is preferably used for the acid anhydride in step (A):

$$YOY \qquad (26)$$

(wherein Y represents Y in which the pKa of a conjugated acid of Y in the form of HY, in which a hydrogen atom has been added to Y, is 0 to 6.8, and O represents an oxygen atom).

Examples of such acid anhydrides include aliphatic acid anhydrides such as acetic anhydride, propionic anhydride, butyric anhydride, isobutyric anhydride, valeric anhydride, isovaleric anhydride, succinic anhydride, maleic anhydride, propionic anhydride, glutaric anhydride or the like; and aromatic acid anhydrides such as benzoic anhydride, phthalic anhydride, pyromellitic anhydride or the like. Among these, acid anhydrides having a standard boiling point of 300° C. or lower are used preferably, and in order to facilitate removal of excess acid anhydride following the reaction, acid anhydrides having a standard boiling point of 200° C. or lower are used more preferably. Moreover, maleic anhydride and acetic anhydride are preferable from the viewpoints of facilitating the removal of by-products such as carboxylic acid esters and acyl halides outside the system and ease of industrial acquisition.

Although these acids and acid anhydrides can be used alone or by mixing a plurality of types, in the case of using acid, there are many cases in which water is formed in the case of reacting acid with deactivated forms of the dialkyl tin catalyst. Distillation separation or membrane separation may be carried out or a dehydrating agent may be used to remove said water. In addition, the combined use of an acid anhydride for the dehydrating agent is preferable. Moreover, in the case of using the acid anhydride only, since there are many cases in which water is not formed in the reaction between acid anhydride and deactivated forms of the dialkyl tin catalyst, methods using only acid anhydride are also preferable.

The amount of acid and/or acid anhydride used is preferably within a stoichiometric range of from 0.1 to 50 times based on the tin atom contained in the composition of deactivated forms of the dialkyl tin catalyst in consideration of the reaction rate and final dialkyl tin compound yield in step (A), and more preferably within the range of from 0.5 to 20 times in consideration of the size of the reaction vessel and the reaction rate. In the case of a stoichiometric ratio of less than 0.1, there are cases in which the reaction has difficulty in proceeding, while conversely even in the case of a stoichiometric ratio of 50 times or more, there are many cases in which there are no effects on the reaction rate or final dialkyl tin compound yield in said step.

The reaction of step (A) is preferably carried out at a reaction temperature of from −20 to 300° C., more preferably carried out at a reaction temperature of from −10 to 250° C., and although a high reaction temperature is preferable for increasing the reaction rate, since there are also cases in which undesirable reactions such as decomposition occur at high temperatures thereby resulting in a decrease in yield, the reaction is even more preferably carried out at a reaction temperature of from 0 to 230° C. In addition, the reaction of step (A) is preferably carried out in an inert gas atmosphere such as that containing argon, neon or nitrogen.

Although the use of a solvent is not required in step (A), a solvent can be used for the purpose of improving fluidity, facilitating the reaction procedure, or efficiently removing water outside the system in the case water is generated in the reaction. Examples of such solvents include linear, branched or cyclic hydrocarbons having 5 to 16 carbon atoms, ethers composed of linear, branched or cyclic hydrocarbons having 4 to 16 carbon atoms, and linear, branched or cyclic halogenated hydrocarbons having 1 to 16 carbon atoms. Specific examples of solvents that can be used include linear or cyclic hydrocarbons selected from pentane (isomers), hexane (isomers), heptane (isomers), octane (isomers), nonane (isomers), decane (isomers), hexadecane (isomers), cyclohexane, cycloheptane, cyclooctane, benzene, toluene, xylene (isomers), ethylbenzene or the like; ethers selected from diethyl ether, dipropyl ether (isomers), dibutyl ether (isomers), dihexyl ether (isomers), dioctyl ether (isomers), diphenyl ether or the like; and halogenated hydrocarbons selected from methylene chloride, chloroform, carbon tetrachloride, chlorobenzene, tetrachloroethane, dichlorobenzene (isomers) or the like. These solvents can be used alone or two or more types can be used as a mixture.

The optimum process for producing the dialkyl tin compound by the alkyl group redistribution reaction of the present embodiments as described above preferably comprises converting a substituent of a composition of deactivated forms of the dialkyl tin catalyst, in which the pKa of a conjugated acid of said substituent of the dialkyl tin catalyst is 6.8 to 25, to the above-mentioned Y followed by further heat-treating at a high temperature. Since the alkyl group redistribution reaction of the present embodiments is the equilibrium reaction and based on the typical properties of the equilibrium reaction, the alkyl group redistribution reaction of the present embodiments is preferably carried out according to the procedure described above using the composition of deactivated forms in which said deactivated forms have been accumulated and/or concentrated to a high concentration (for example, the composition of deactivated forms in which the content of deactivated forms, in which the number of alkyl groups bound to the tin atom of the alkyl tin compound is a number other than 2 with respect to the total number of moles of tin of the alkyl tin compound contained in the composition of deactivated forms of the dialkyl tin catalyst, when represented as mol %, is 10 mol % or more, preferably 30 mol % or more and more preferably 50 mol % or more).

<Case of Separating Trialkyl Tin Compounds from Composition of Deactivated Forms of Dialkyl Tin Catalyst>

The following provides an explanation of the case of separating a composition containing trialkyl tin compounds, and a composition containing compounds containing a tin atom demonstrating a chemical shift at from −220 to 610 ppm based on tetramethyl tin when analyzed by $^{119}$Sn-NMR in a heavy chloroform solution, from the composition of deactivated forms of dialkyl tin catalyst prior to carrying out step (A).

In the case of having separated compositions of deactivated forms of the dialkyl tin catalyst, each composition can be reacted with acid and/or acid anhydride under different temperature conditions.

The temperature when reacting the composition containing the trialkyl tin compounds separated from the composition of deactivated forms of dialkyl tin the catalyst with the acid and/or acid anhydride is preferably from −20 to 100° C., more preferably from −10 to 85° C., and although a high temperature is preferable for the reaction temperature for increasing the reaction rate, since there are cases in which undesirable reactions such as decomposition occur at high temperatures resulting in a decrease in yield, the reaction temperature is even more preferably from 0 to 70° C. On the other hand, the temperature when reacting the composition containing the organic tin compounds containing a tin atom demonstrating a chemical shift at from −220 to 610 ppm based on tetramethyl tin when analyzed by $^{119}$Sn-NMR in heavy chloroform, separated from the composition of deactivated forms of the dialkyl tin catalyst, with the acid and/or acid anhydride is preferably from −20 to 300° C., more preferably from −10 to 250° C., and although a high temperature is preferable for the reaction temperature for increasing the reaction rate, since there are cases in which undesirable reactions such as decomposition occur at high temperatures resulting in a decrease in yield, the reaction temperature is even more preferably from 0 to 230° C. Each reaction product is mixed into a single mixture followed by heat treatment to produce the dialkyl tin compound.

<Removal of Unreacted Substances and By-Products>

Reaction products obtained by reacting the composition of deactivated forms of dialkyl tin catalyst and the acid and/or acid anhydride in step (A) may be subjected directly to heat treatment, or unreacted acid and/or acid anhydride and/or organic compounds not containing tin atoms formed by the reaction may be first removed followed by undergoing heat treatment. Known methods such as filtration, distillation separation, membrane separation or solvent extraction can be used to remove unreacted acid and/or acid anhydride and/or organic compounds not containing tin atoms formed by the reaction.

<Dealkylation Reaction>

The following provides an explanation of the dealkylation reaction in the present embodiments.

As a result of extensive studies conducted by the inventors of the present invention, it was surprisingly found that when the composition of deactivated forms of the dialkyl tin catalyst is reacted with the specific acid, dialkyl tin compounds can be easily obtained from trialkyl tin components (organic tin compounds in which three alkyl groups are bound to a tin atom) contained in said deactivated forms. The following provides a detailed explanation of said dealkylation reaction.

A dealkylation reaction in the present embodiments refers to a reaction in which the composition of deactivated forms of the dialkyl tin catalyst is reacted with the acid and/or acid anhydride to form an organic tin compound having an Sn—Y bond in which a Y group originating from the acid and/or acid anhydride is bound to a tin atom by eliminating an alkyl group bound to the tin atom. Although the detailed reaction mechanism of said dealkylation reaction is unclear, for example, the dialkyl tin compound having an Sn—Y bond is presumed to be formed by the reaction between the trialkyl tin compound and the acid HY as shown in the following formula (27):

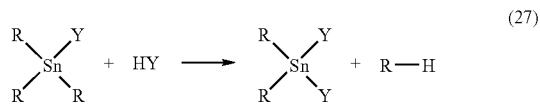

(27)

(wherein R represents a linear or branched alkyl group having 1 to 12 carbon atoms, and Y represents a group other than an alkyl group).

An acid represented by the following formula (25) is preferably used for the acid used in said dealkylation reaction:

HY (25)

(wherein Y is a Y in which the pKa of HY, which is a conjugated acid of Y in which a hydrogen atom has been added to Y, is 0 to 6.8).

An organic acid or inorganic acid may be used for this acid. Examples of inorganic acids include hydrogen halides, hydrohalic acids, sulfuric acid, nitric acid, phosphoric acid and carbonic acid, while hydrogen halides are used preferably and hydrogen chloride is used more preferably. Examples of organic acids include carboxylic acids, sulfonic acids, sulfinic acids, phenols, enols, thiophenols, imides, oxime and aromatic sulfonamides, while carboxylic acids, sulfonic acids, sulfinic acids and phenols are used preferably, and carboxylic acids are used more preferably. Examples of carboxylic acids include saturated or unsaturated aliphatic monocarboxylic acid compounds such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (isomers), octanoic acid (isomers), nonaoic acid (isomers), decanoic acid (isomers), undecanoic acid (isomers), dodecanoic acid (isomers), tetradecanoic acid (isomers), hexadecanoic acid (isomers), acrylic acid, crotic acid, isocrotic acid, vinylacetic acid, methacrylic acid, angelic acid, tiglic acid, allylacetic acid, undecenoic acid (isomers) or the like; saturated or unsaturated aliphatic dicarboxylic acids such as oxalic acid, malonic acid, succinic acid, glutaric acid, adipic acid, heptanedioic acid (isomers), octanedioic acid (isomers), nonanedioic acid (isomers), decanedioic acid (isomers), maleic acid, fumaric acid, methylmaleic acid, methylfumaric acid, pentenedioic acid (including isomers), itaconic acid, allylmalonic acid or the like; saturated or unsaturated aliphatic tricarboxylic acid compounds such as 1,2,3-propanetricarboxylic acid, 1,2,3-propenetricarboxylic acid, 2,3-dimethylbutane-1,2,3-tricarboxylic acid or the like; aromatic carboxylic acid compounds such as benzoic acid, methylbenzoic acid (isomers), ethylbenzoic acid (isomers), propylbenzoic acid (isomers), dimethylbenzoic acid (isomers), trimethylbenzoic acid (isomers) or the like; aromatic dicarboxylic acid compounds such as phthalic acid, isophthalic acid, terephthalic acid, methylisophthalic acid (isomers) or the like; and aromatic tricarboxylic acid compounds such as hemimellitic acid, trimellitic acid, trimesic acid or the like. Among these carboxylic acids, saturated monocarboxylic acids are used preferably, while saturated monocarboxylic acids having a standard boiling point of 300° C. or lower are used more preferably, and saturated monocarboxylic acids having a standard boiling point of 250° C. or lower are used even more preferably. More specifically, acetic acid, propionic acid, n-butyric acid, isobutyric acid, valeric acid, isovaleric acid, 2-methylbutanoic acid, pivalic acid and hexanoic acid are used preferably.

In addition, an acid anhydride represented by the following formula (26) is also preferably used in said dealkylation reaction:

YOY (26)

(wherein Y represents Y in which the pKa of a conjugated acid of Y in the form of HY, in which a hydrogen atom has been added to Y, is 0 to 6.8, and O represents an oxygen atom).

Examples of such acid anhydrides include aliphatic acid anhydrides such as acetic anhydride, propionic anhydride, butyric anhydride, isobutyric anhydride, valeric anhydride, isovaleric anhydride, succinic anhydride, maleic anhydride, propionic anhydride, glutaric anhydride or the like; and aromatic acid anhydrides such as benzoic anhydride, phthalic anhydride, pyromellitic anhydride or the like. Among these, acid anhydrides having a standard boiling point of 300° C. or lower are used preferably, and in order to facilitate removal of excess acid anhydride following the reaction, acid anhydrides having a standard boiling point of 200° C. or lower are used more preferably. Moreover, maleic anhydride and acetic anhydride are preferable from the viewpoints of facilitating the removal of by-products such as carboxylic acid esters and acyl halides outside the system and ease of industrial acquisition.

These acids and acid anhydrides can be used alone or a plurality of types can be used as a mixture.

The amount of acid and/or acid anhydride used is preferably within the range of a stoichiometric ratio of from 0.1 to 50 times based on the tin atom contained in the composition of deactivated forms of the dialkyl tin catalyst in consideration of the reaction rate and final dialkyl tin compound yield in the dealkylation reaction, and more preferably within the range of from 0.5 to 20 times in consideration of the size of the reaction vessel and the reaction rate. In the case of a stoichiometric ratio of less than 0.1, there are cases in which the reaction has difficulty in proceeding, while conversely even in the case of a stoichiometric ratio of 50 times or more, there are many cases in which there are no effects on the reaction rate or final dialkyl tin compound yield in said dealkylation reaction.

Said dealkylation reaction is preferably carried out at a reaction temperature of from −20 to 300° C., more preferably carried out at a reaction temperature of from −10 to 250° C., and although a high reaction temperature is preferable for increasing the reaction rate, since there are also cases in which undesirable reactions such as decomposition occur at high temperatures thereby resulting in a decrease in yield, the reaction is even more preferably carried out at a reaction temperature of from 0 to 230° C. In addition, the dealkylation reaction is preferably carried out in an inert gas atmosphere such as that containing argon, neon or nitrogen.

Although the use of a solvent is not required in said dealkylation reaction, a solvent can be used for the purpose of improving fluidity, facilitating the reaction procedure, or efficiently removing water outside the system in the case water is generated in the reaction. Examples of such solvents include linear, branched or cyclic hydrocarbons having 5 to 16 carbon atoms, ethers composed of linear, branched or cyclic hydrocarbons having 4 to 16 carbon atoms, and linear, branched or cyclic halogenated hydrocarbons having 1 to 16 carbon atoms. Specific examples of solvents that can be used include linear or cyclic hydrocarbons selected from pentane (isomers), hexane (isomers), heptane (isomers), octane (isomers), nonane (isomers), decane (iisomers), hexadecane (isomers), cyclohexane, cycloheptane, cyclooctane, benzene, toluene, xylene (isomers), ethylbenzene or the like; ethers selected from diethyl ether, dipropyl ether (isomers), dibutyl ether (isomers), dihexyl ether (isomers), dioctyl ether (isomers), diphenyl ether or the like; and halogenated hydrocarbons selected from methylene chloride, chloroform, carbon tetrachloride, chlorobenzene, tetrachloroethane, dichlorobenzene (isomers) or the like. These solvents can be used alone or two or more types can be used as a mixture.

The above-mentioned alkyl group redistribution reaction may be carried out simultaneous to said dealkylation reaction. Since said dealkylation reaction is not an equilibrium reaction while the alkyl group redistribution reaction is an equilibrium reaction, both reactions are carried out in combination as necessary.

<Dialkyl Tin Compounds>

Dialkyl tin compounds produced by the alkyl group redistribution reaction and/or dealkylation reaction described above are compounds that include at least one type of compound selected from the group consisting of the dialkyl tin compound represented by the following formula (13) and the tetraalkyl distannoxane compound represented by the following formula (14):

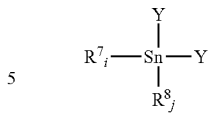

(13)

(wherein $R^7$ and $R^8$ represent groups originating from a dialkyl tin catalyst and each independently represent a linear or branched alkyl group having 1 to 12 carbon atoms, Y represents a group originating from a dialkyl tin catalyst or a group originating from an acid (HY) and/or acid anhydride (YOY), the pKa of a conjugated acid of Y in the form of HY in which a hydrogen atom has been added is 0 to 6.8, and i and j independently represent an integer of 0 to 2, and i+j=2);

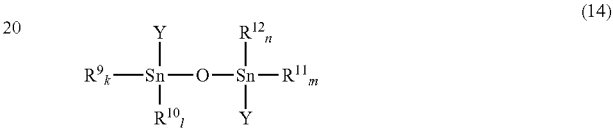

(14)

(wherein $R^9$, $R^{10}$, $R^{11}$ and $R^{12}$ represent groups originating from a dialkyl tin catalyst and independently represent a linear or branched alkyl group having 1 to 12 carbon atoms, Y represents a group originating from a dialkyl tin catalyst or a group originating from an acid (HY) and/or acid anhydride (YOY), the pKa of a conjugated acid of Y in the form of HY in which a hydrogen atom has been added is 0 to 6.8, and k, l, m and n respectively represent an integer of 0 to 2, k+l=2 and m+n=2).

<Production of Dialkyl Tin Catalyst Having Dialkyl Tin Compound as Raw Material>

A dialkyl tin catalyst can be produced according to the method of step (I) using the dialkyl tin compound produced according to the method described above as the raw material.

Step (I): A step in which a substituent Y of the dialkyl tin compound having an Sn—Y bond is converted to at least one type of substituent selected from the group consisting of an alkoxy group, an acyloxyl group and a halogen atom.

Said step (I) is preferably a step comprising the following steps (I-1) to (I-2):

Step (I-1): (Hydrolysis Step) A composition containing a dialkyl tin oxide compound is obtained by hydrolyzing the dialkyl tin compound having the Sn—Y bond by adding an aqueous alkaline solution; and, Step (I-2): A component containing generated water is removed from the reaction liquid by reacting the composition containing dialkyl tin oxide obtained in step (I-1) with at least one type of compound selected from the group consisting of an alcohol, carboxylic acid and hydrogen halide.

The following provides an explanation of said steps (I-1) to (I-2).

Step (I-1) is a step of obtaining a composition containing dialkyl tin oxide compounds by adding an aqueous alkaline solution to the dialkyl tin compound obtained by the alkyl group redistribution reaction and/or dealkylation reaction. Here, an aqueous alkaline solution refers to an aqueous solution in which an alkali has been dissolved in water. An alkali is the generic term for a substance that adopts the form of a hydroxide MOH and dissolves in water as described in Encyclopedia Chimica Volume 1 (Kyoritsu Publishing Co., Ltd., 38th Compact Edition). Although M indicates an alkyl metal or ammonium group, in addition to referring to hydroxides of calcium and barium, hydroxides are also used in the broad sense to include sodium carbonate, ammonium carbonate, sodium phosphate or the like.

There are no particular limitations on the aqueous alkaline solution used in said step (I-1) provided the pH of a solution thereof is greater than 7, and examples include an aqueous lithium hydroxide solution, an aqueous sodium hydroxide solution, an aqueous potassium hydroxide solution, an aqueous cesium hydroxide solution, an aqueous potassium carbonate solution, an aqueous sodium carbonate solution, an aqueous sodium bicarbonate solution, an aqueous ammonium carbonate solution, an aqueous sodium phosphate solution or the like. Among these, the aqueous sodium hydroxide solution, the aqueous potassium hydroxide solution, the aqueous potassium carbonate solution are used preferably. These aqueous alkaline solutions may be used alone or two or more types may be used as a mixture. There are no particular limitations on the amount of the aqueous alkaline solution used provided it is an adequate amount for forming a precipitate, it is preferably used at a weight ratio of from 1 to 10 times the amount of the mixture containing dialkyl tin compounds obtained by the alkyl group redistribution reaction and/or dealkylation reaction.

There are no particular limitations on the temperature at which step (I-1) is carried out, and the temperature is preferably from −10 to 100° C., more preferably from −5 to 50° C., and although a high temperature is preferable for the reaction temperature for increasing the reaction rate, since there are cases in which undesirable reactions such as decomposition occur at high temperatures thereby resulting in a decrease in yield, the temperature is even more preferably from 0 to 30° C.

The composition containing dialkyl tin oxide compounds is obtained by said step (I-1). The composition containing dialkyl tin oxide compounds can be separated in the form of the precipitate. A known method can be used for the separation method, and for example, the composition can be separated by filtration.

Step (I-2) is a step of reacting a composition containing dialkyl tin oxide compounds separated in step (I-1) with at least one type of compound selected from the group consisting of an alcohol, carboxylic acid and hydrogen halide to remove a component containing generated water from the reaction liquid. Examples of alcohols used in said step (I-2) include alcohols in which the number of carbon atoms that compose said alcohol is a number selected from an integer of 1 to 12, such as methanol, ethanol, propanol (isomers), butanol (isomers), pentanol (isomers), hexanol (isomers), heptanol (isomers), octanol (isomers), nonanol (isomers), decanol (isomers) or the like. In addition, examples of carboxylic acids used in said step (I-2) include carboxylic acids in which the number of carbon atoms that compose said carboxylic acid is a number selected from an integer of 1 to 12, such as formic acid, acetic acid, propionic acid, n-butyric acid, isobutyric acid, valeric acid, isovaleric acid, 2-methylbutanoic acid, pivalic acid, hexanoic acid, isocaproic acid, 2-ethylbutanoic acid, 2,2-dimethylbutanoic acid, heptanoic acid (isomers), octanoic acid (isomers), nonanoic acid (isomers), decanoic acid (isomers), undecanoic acid (isomers), dodecanoic acid (isomers) or the like. In addition, examples of hydrogen halides used in said step (I-2) include hydrogen chloride, hydrogen bromide or the like.

The stoichiometric ratio of the amount of reaction agent used in said step (I-2) (the term "reaction agent" is hereinafter used to refers to an alcohol, carboxylic acid or hydrogen halide) based on tin atoms in the composition containing dialkyl tin oxide is from 1 to 1000 times, preferably from 2 to 100 times, and although an excess amount is preferable for increasing the reaction rate, the amount is even more preferably from 3 to 50 times in consideration of the ease of removal after the reaction. The aforementioned range is preferable since removal of reaction agent after the reaction requires a considerable amount of energy in the case of using an overly excessive amount of reaction agent.

Although the use of a solvent is not necessarily required in said step (I-2), an azeotropic solvent with water can be added for the purpose of improving fluidity, facilitating the reaction procedure or rapidly removing generated water outside the system. Solvents that can be used may be any solvent provided it does not react with dialkyl tin oxide or dialkyl tin catalyst formed in said step. Examples of such solvents include branched, linear or cyclic aliphatic hydrocarbons such as hexane (isomers), heptane (isomers), octane (isomers) or the like; aromatic hydrocarbons such as benzene, toluene, xylene (including isomers) or the like; ethers.

Although varying according to the type of reaction agents and solvent used and the composite ratio thereof, the temperature at which said step (I-2) is carried out is preferably within the range of from 80 to 200° C., and although a high temperature is preferable for the reaction temperature for increasing the reaction rate, since there are cases in which undesirable reactions such as decomposition occur at high temperatures, the reaction temperature is more preferably within the range of from 100 to 180° C.

There are no particular limitations on the pressure at which said step (I-2) is carried out, and although it can be carried out under conditions of reduced pressure to increased pressure, in order to efficiently remove water from the reaction system, this step is preferably carried out within the range of from 10 Pa to 1 MPa and more preferably within the range of from 10 kPa to 0.5 MPa.

As has been previously described, although it is necessary to remove water generated by the reaction from the reaction system in said step (I-2), a known dehydration method can be used for the dehydration method, examples of which include distillation separation, reduced pressure distillation, pressurized distillation, thin film distillation, azeotropic distillation or the like. A method such as pervaporation can be used for membrane separation, while a known dehydrating agent such as a molecular sieve can be used as a dehydrating agent.

There are no particular limitations on the reaction vessel used in each reaction of the present embodiments, and a known reaction vessel can be used. Conventional reaction vessels can be suitably combined for use, examples of which include a stirring tank, pressurized stirring tank, depressurized stirring tank, column reactor, distillation column, packed column, thin film distillation still or the like. There are also particular limitations on the material of the reaction vessel, and a known material can be used. For example, a reaction vessel made of glass, stainless steel, carbon steel or Hastelloy, or a reaction vessel made of a base material provided with a glass lining or a Teflon-coated reaction vessel can be used. Since there are cases in which corrosion by acid may be prominent depending on the step and conditions, in such cases a reaction vessel made of glass, that having a glass lining, that provided with a Teflon (™) coating or that made of Hastelloy may be suitably selected.

The dialkyl tin catalyst produced in the previously described steps can be used to produce ester compounds. As was previously described, the optimum process for producing the dialkyl tin compound by the alkyl group redistribution reaction of the present embodiments allows the dialkyl tin compound to be obtained extremely efficiently in the case of converting a substituent of a composition of deactivated forms of the dialkyl tin catalyst, in which the pKa of a conjugated acid of the substituent of the dialkyl tin catalyst is 6.8 to 25, to the above-mentioned Y followed by heat-treating at a high temperature. In such an example, after treating the composition of deactivated forms of the dialkyl tin alkoxide formed from a carbonic acid ester production process that uses a dialkyl tin alkoxide as a dialkyl tin catalyst as described below with an acid and/or acid anhydride, preferably an acid anhydride and more preferably acetic anhydride in accordance with the previously described step (A), the alkyl group redistribution reaction is carried out by heat treatment, and the dialkyl tin compound formed (and preferably dialkyldiacetoxy tin) is converted to dialkyl tin alkoxide followed by recycling as a catalyst for the production of carbonic acid ester. In this case as well, since the alkyl group redistribution reaction of the present embodiments is an equilibrium reaction as previously described, and based on the typical properties of an equilibrium reaction, the alkyl group redistribution reaction of the present embodiments is preferably carried out according to the procedure described above using the composition of deactivated forms in which said deactivated forms have been accumulated and/or concentrated to a high concentration (for example, a composition of deactivated forms in which the content of deactivated forms, in which the number of alkyl groups bound to the tin atom of the alkyl tin compound is a number other than 2 with respect to the total number of moles of tin of the alkyl tin compound contained in the composition of deactivated forms of the dialkyl tin catalyst, when represented as mol %, is 10 mol % or more, preferably 30 mol % or more and more preferably 50 mol % or more).

Namely, one object of the present invention is to produce the dialkyl tin compound from the composition of deactivated forms of the dialkyl tin catalyst formed during a process for producing ester compounds, regenerate said dialkyl tin compound as a dialkyl tin catalyst, and reuse as a catalyst for the production of ester compounds, and particularly carbonic acid esters.

The process for producing carbonic acid esters preferably comprises the following steps (1) to (4):
Step (1): (carbonic acid ester formation step) carbon dioxide and dialkyl tin catalyst are reacted to obtain a reaction liquid containing carbonic acid ester;
Step (2) (carbonic acid ester separation step) the carbonic acid ester is separated from the reaction liquid to obtain a residual liquid;
Step (3) (dialkyl tin catalyst regeneration step) the residual liquid and alcohol are reacted and generated water is removed outside the system to regenerate the dialkyl tin catalyst; and
Step (4) (recycling step) the dialkyl tin catalyst obtained in step (3) is recycled back to step (1).

The following provides a detailed explanation of each step using the example of a process for producing carbonic acid ester using dialkyl tin alkoxide for the dialkyl tin catalyst.
(i) Alkyl Tin Alkoxide Synthesis Step (Step When Starting Up Continuous Operation)

In this step, a previously disclosed process for producing alkyl tin alkoxide (such as WO 2005/111049) can be used preferably. This step is a step of producing an alkyl tin alkoxide from a dialkyl tin oxide and alcohol.

Alcohols in which the number of carbon atoms that compose the alcohol is a number selected from an integer of 1 to 12, such as methanol, ethanol, propanol (isomers), butanol (isomers), pentanol (isomers), hexanol (isomers), heptanol (isomers), octanol (isomers), nonanol (isomers), decanol (isomers) or the like, are preferably used for the alcohol.

A dialkyl tin oxide represented by the following formula (28) is used for the dialkyl tin oxide used in the alkyl tin alkoxide synthesis step:

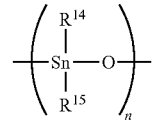

(28)

(wherein $R^{14}$ and $R^{15}$ independently represent a linear or branched alkyl group having 1 to 12 carbon atoms).

Examples of $R^{14}$ and $R^{15}$ include alkyl groups which are aliphatic hydrocarbon groups having 1 to 12 carbon atoms such as a methyl, ethyl, propyl (isomers), butyl (isomers), pentyl (isomers), hexyl (isomers), heptyl (isomers), octyl (isomers), nonyl (isomers), decyl (isomers), undecyl (isomers), dodecyl (isomers) group or the like, preferably linear or branched saturated alkyl groups having 1 to 8 carbon atoms, and more preferably an n-butyl group or n-octyl group.

Said alcohol and said dialkyl tin oxide are subjected to a dehydration reaction and the water generated is removed outside the system while obtaining tetraalkyl dialkoxy distannoxane and/or dialkyl tin dialkoxide. The temperature at which said reaction is carried out is, for example from 80 to 180° C., and in order to remove generated water outside the system, the reaction temperature is preferably from 100 to 180° C. although varying according to the pressure, and although a high temperature is preferable for the reaction temperature for increasing the reaction rate, since there are cases in which undesirable reactions such as decomposition occur at high temperatures, the reaction temperature is more preferably within the range of from 100 to 160° C. The reaction pressure is a pressure that allows generated water to be removed outside the system, and although varying according to the reaction temperature, is within the range of from 20 to $1 \times 10^6$ Pa. There are no particular limitations on the reaction time of the dehydration reaction, and is generally from 0.001 to 50 hours, preferably from 0.01 to 10 hours and more preferably from 0.1 to 2 hours. The reaction is completed once the desired alkyl tin alkoxide composition has been obtained. The progression of the reaction can also be determined by measuring the amount of water extracted outside the system, or by a method using $^{119}$Sn-NMR by sampling the reaction liquid.

In order to produce the mixture of the present embodiments in step (1), the reaction is completed after confirming the obtaining of the composition in which the molar ratio of tetraalkyl dialkoxy distannoxane to dialkyl tin dialkoxide contained in the alkyl tin alkoxide composition obtained in the above-mentioned reaction is within the range of from 0:100 to 80:20 when represented as the combined mol % of both, and more preferably within the range of from 10:90 to 70:30. The alcohol used may be allowed to remain present or may be removed by distillation depending on the case. It is preferable to remove as much of the alcohol as possible since this offers the advantage of being able to reduce the size of the reaction vessels of the other steps. Removal by a known distillation method is preferable for the removal method, and a known distillation apparatus can be used for the distillation apparatus used to distill off the alcohol. A thin film distillation apparatus can be preferably used for the distillation apparatus since it allows alcohol to be removed in a short period of time. There are no particular limitations on the type of reaction vessel of the dehydration reaction, and a known tank-type or column-type reaction vessel can be used. A low boiling point reaction mixture containing water is extracted from the reaction vessel by distillation in the form of a gas, while a high boiling point reaction mixture containing the produced alkyl tin alkoxide or alkyl tin alkoxide mixture is extracted from the bottom of the reaction vessel in the form of a liquid. Various known methods are used for such a reaction vessel, such as methods using reaction vessels including any of, for example, a stirring tank, multistage stirring tank, distillation column, multistage distillation column, multitubular reactor, continuous multistage distillation column, packed column, thin film evaporator, reactor provided with a support inside, forced circulation reactor, falling film evaporator, falling drop evaporator, narrow flow phase reactor or bubble column as well as combinations thereof. Methods using a column-type reaction vessel are preferable in terms of efficiently shifting the equilibrium to the products side, and a structure having a large gas-liquid contact area enabling generated water to promptly move into the gaseous phase is preferable. Although a continuous method using a multitubular reactor, multistage distillation column or packed column packed with a packing material can also be used, since the dialkyl tin oxide used in this step is ordinarily a solid, a method in which this step is first carried out in a tank-type reaction vessel followed by increasing the content of dialkyl tin dialkoxide in a column-type reaction vessel is the most preferable. Although known materials may be used for the reaction vessel and lines provided they do not have detrimental effects, materials such as SUS304, SUS316 or SUS316L are inexpensive and can be used preferably. Known processing equipment including instruments such as flow meters and thermometers, reboilers, pumps and compressors may be added as necessary, a known method such as steam heating or a heater may be used for heating, and a known method such as air cooling, cold water or brine can be used for cooling.

(ii) Dialkyl Tin Catalyst Regeneration Step (Step 3)

Although this step is carried out after obtaining a residual liquid in step (2), since it resembles the dialkyl tin alkoxide synthesis step described above, it will be explained first. This step is a step of subjecting the residual liquid obtained in step (2) and alcohol to a dehydration reaction to regenerate dialkyl tin alkoxide.

Although alcohols in which the number of carbon atoms that compose the alcohol is a number selected from an integer of 1 to 12, such as methanol, ethanol, propanol (isomers), butanol (isomers), pentanol (isomers), hexanol (isomers), heptanol (isomers), octanol (isomers), nonanol (isomers), decanol (isomers) or the like, is preferably used for the alcohol, the same alcohol as that used in the above-mentioned alkyl tin alkoxide synthesis step is used more preferably.

The dehydration reaction is preferably carried out under the same conditions as the conditions of the alkyl tin alkoxide synthesis step. The reaction is completed once the desired alkyl tin alkoxide composition is obtained. The progression of the reaction can also be determined by measuring the amount of water extracted outside the system, or by a method using $^{119}$Sn-NMR by sampling the reaction liquid. In order to produce the mixture of the present embodiments in step 1, the reaction is completed after confirming the obtaining of the composition in which the molar ratio of tetraalkyl dialkoxy distannoxane to dialkyl tin dialkoxide contained in the alkyl tin alkoxide composition obtained in the above-mentioned reaction is within the range of from 0:100 to 80:20 when represented as the combined mol % of both, and more preferably within the range of from 10:90 to 70:30. The alcohol used may be allowed to remain present or may be removed by distillation depending on the case. It is preferable to remove as much of the alcohol as possible since this offers the advantage of being able to reduce the size of the reaction vessels of the other steps. Removal by a known distillation method is preferable for the removal method, and a known distillation apparatus can be used for the distillation apparatus used to distill off the alcohol. A thin film distillation apparatus can be preferably used for the distillation apparatus since it allows alcohol to be removed in a short period of time. Differing from the alkyl tin alkoxide synthesis step, since this step does not use dialkyl tin oxide generally in a solid state, there are few restrictions on the reaction vessel. Namely, there are no particular limitations on the type of reaction vessel of the dehydration reaction, and a known tank-type or column-type reaction vessel can be used. A low boiling point reaction mixture containing water is extracted from the reaction vessel by distillation in the form of a gas, while a high boiling point reaction mixture containing the produced alkyl tin alkoxide or alkyl tin alkoxide mixture is extracted from the bottom of the reaction vessel in the form of a liquid. Various known methods are used for such a reaction vessel, such as methods using reaction vessels including any of, for example, a stirring tank, multistage stirring tank, distillation column, multistage distillation column, multitubular reactor, continuous multistage distillation column, packed column, thin film evaporator, reactor provided with a support inside, forced circulation reactor, falling film evaporator, falling drop evaporator, narrow flow phase reactor or bubble column as well as combinations thereof. Methods using a column-type reaction vessel are preferable in terms of efficiently shifting the equilibrium to the products side, and a structure having a large gas-liquid contact area enabling generated water to promptly move into the gaseous phase is preferable. A continuous method using a multitubular reactor, multistage distillation column or packed column packed with a packing material is particularly preferable. Although known materials may be used for the reaction vessel and lines provided they do not have detrimental effects, materials such as SUS304, SUS316 or SUS316L are inexpensive and can be used preferably. Known processing equipment including instruments such as flow meters and thermometers, reboilers, pumps and compressors may be added as necessary, a known method such as steam heating or a heater may be used for heating, and a known method such as air cooling, cold water or brine can be used for cooling.

(iii) Carbonic Acid Ester Formation Step (Step 1)

Although the present step is a step of reacting a dialkyl tin alkoxide and gaseous carbon dioxide to produce carbonic acid ester, a previously disclosed carbonic acid ester production process (such as WO 03/055840 or WO 04/014840) is preferably used for this step.

The alkyl tin alkoxide composition supplied in this step may be supplied from the alkyl tin alkoxide synthesis step at the time of startup or from the alkyl tin alkoxide production step of step (3) during continuous production. In addition, there are cases in which it is also supplied from a step of regenerating dialkyl tin catalyst to be described later.

In this step, gaseous carbon dioxide are first absorbed to the above-mentioned dialkyl tin alkoxide to cause a chemical reaction and obtain a mixture containing a carbon dioxide bound form of dialkyl tin alkoxide.

During said chemical reaction, said dialkyl tin alkoxide is reacted in the form of a liquid or in the form of a liquid with a solvent and the like. A method for obtaining a liquid by heating is used preferably to put the dialkyl tin oxide into a liquid state. In addition, it may also be put into a liquid state with a solvent or the like. Although varying according to the temperature at which the reaction is carried out, the pressure of the reaction is preferably within the range of normal pressure to 1 MPa and more preferably within the range of normal pressure to 0.6 MPa. Although varying according to the reaction pressure, the reaction temperature is preferably within the range of from −40 to 80° C., and in consideration of fluidity during transfer, is more preferably within the range of from 0 to 80° C. and most preferably within the range of from room temperature, for example 20° C., to 80° C. The reaction time is within the range of from several seconds to 100 hours, and in consideration of productivity or the like, is preferably from several minutes to 10 hours. A known tank-type reaction vessel or column-type reaction vessel can be used for the reaction vessel. In addition, a plurality of reaction vessels may be used in combination. Since the reaction consists of a reaction between carbon dioxide (gas) and an alkyl tin alkoxide composition (liquid), it is preferable to increase the contact area between the gas and liquid by increasing the gas-liquid interface in order to allow the reaction to proceed efficiently. Known findings can be used for the method for reacting by increasing the gas-liquid interface in this manner, and in the case of a tank-type reaction vessel for example, a method that increases the stirring speed or generates air bubbles in the liquid is preferable, while in the case of a column-type reaction vessel, a method that uses a packed column or plate column is preferable. Examples of such column-type reaction vessels that can be used include plate column types using a bubble tray, porous plate tray, valve tray or counter-current tray, and packed column types packed with various types of packing materials such as a raschig ring, lessing ring, pole ring, Berl saddle, Interlock saddle, Dixon packing, McMahon packing, Helipack, Sulzer packing, Mellapack or the like. Although known materials may be used for the reaction vessel and lines provided they do not have detrimental effects, materials such as SUS304, SUS316 or SUS316L are inexpensive and can be used preferably. Known processing equipment including instruments such as flow meters and thermometers, reboilers, pumps and compressors may be added as necessary, a known method such as steam heating or a heater may be used for heating, and a known method such as air cooling, cold water or brine can be used for cooling. Since the reaction is generally exothermic reaction, cooling may be performed, or cooling by heat dissipated from the reaction vessel may be performed. Alternatively, heating may be performed for the purpose of simultaneously causing carbonic acid esterification. A known method using a jacket or internal coils can be used for cooling and heating the reactor. The carbon dioxide gas and alkyl tin alkoxide composition supplied to the reaction vessel may be supplied to the reaction vessel separately, or they may be mixed prior to supplying to the reaction vessel. They may also be supplied from a plurality of locations of reaction vessels. Completion of the reaction can be determined by, for example, $^{119}$Sn-NMR analysis.

Next, a reaction liquid containing carbonic acid ester is obtained from the carbon dioxide bound form of dialkyl tin alkoxide obtained above according to the method described below.

Although the reaction conditions are such that the reaction temperature is within the range of from 110 to 200° C., and a high temperature is preferable for the reaction temperature for increasing the reaction rate, since there are cases in which undesirable reactions such as decomposition also occur at high temperatures causing a decrease in yield, the reaction temperature is preferably within the range of from 120 to 180° C., the reaction time is within the range of from 0.1 to 10 hours, and the reaction pressure is within the range of from 1.5 to 20 MPa and preferably within the range of from 2.0 to 10 MPa. The reaction is completed after the desired carbonic acid ester has been formed in the reaction vessel. Progression of the reaction can be confirmed by a method such as sampling reaction fluid within the reaction vessel and analyzing carbonic acid ester formed by a method such as $^1$H-NMR or gas chromatography. For example, the reaction may be completed once 10% or more has been formed with respect to the number of moles of dialkyl tin alkoxide and/or carbon dioxide bound form of dialkyl tin alkoxide contained in the dialkyl tin alkoxide and/or carbon dioxide bound form of dialkyl tin alkoxide, or in the case of desiring to increase the yield of carbonic acid ester, the reaction may be completed after allowing to continue until said value reaches 90% or more. A known reaction vessel can be used for the reaction vessel, and a column-type reaction vessel or tank-type reaction vessel can be used preferably. Although known materials may be used for the reaction vessel and lines provided they do not have detrimental effects, materials such as SUS304, SUS316 or SUS316L are inexpensive and can be used preferably. Known processing equipment including instruments such as flow meters and thermometers, reboilers, pumps and compressors may be added as necessary, a known method such as steam heating or a heater may be used for heating, and a known method such as air cooling, cold water or brine can be used for cooling.

(iv) Carbonic Acid Ester Separation Step (Step 2)

This step is a step of separating carbonic acid ester from the reaction liquid containing carbonic acid ester obtained in step (1) to obtain a residual liquid. A known method and apparatus can be preferably used for the separation method. A preferable separation method is separation by distillation.

Carbonic acid ester and residual liquid are obtained by batch, semi-batch or continuous distillation of the reaction liquid transferred from step (1). A preferable distillation method comprises: supplying said reaction liquid to a distillation still; separating carbonic acid ester from the top of the distillation still outside the system in the form of a gaseous component; and extracting the residual liquid from the bottom of the distillation still in the form of a liquid component. Although varying according to the boiling point of said carbonic acid ester and pressure, the temperature of this step is within the range of from room temperature, for example 20° C., to 200° C., and since there are cases in which denaturation of tin compounds in the residual liquid occurs at high temperatures as well as cases in which the carbonic acid ester ends up decreasing due to a reverse reaction, the temperature is preferably within the range of from room temperature, for example 20° C., to 150° C. Although varying according to the type of carbonic acid ester and temperature at which this step is carried out, pressure is generally from normal pressure to reduced pressure, and in consideration of productivity, the pressure is preferably within the range of from 100 Pa to 80 KPa and most preferably within the range of from 100 Pa to 50 KPa. This step can be carried out within the range of from 0.01 to 10 hours, and since there are cases in which tin compounds contained in the reaction liquid may be denatured or carbonic acid ester may decrease due to a reverse reaction if this step is carried out at a high temperature for an extended period of time, the reaction time is preferably within the range of from 0.01 to 0.5 hours and most preferably within the range of from 0.01 to 0.3 hours. A known distillation still can be used for the distillation still, a column-type distillation still or tank-type distillation still can be used preferably, or a plurality of types may be used in combination. More preferably, the distillation still is a thin film evaporator or thin film distillation still, while a thin film evaporator equipped with a distillation column or a thin film distillation still is the most preferable. Although known materials may be used for the distillation still and lines provided they do not have detrimental effects, materials such as SUS304, SUS316 or SUS316L are inexpensive and can be used preferably. Known processing equipment including instruments such as flow meters and thermometers, reboilers, pumps and compressors may be added as necessary, a known method such as steam heating or a heater may be used for heating, and a known method such as air cooling, cold water or brine can be used for cooling.

Although the foregoing description has indicated an example of producing carbonic acid ester using a dialkyl tin alkoxide catalyst, deactivated forms of the dialkyl tin alkoxide catalyst are generated during the process of said carbonic acid ester production. Said deactivated forms of the dialkyl tin alkoxide catalyst gradually accumulate in the reaction system as the production of carbonic acid ester is repeated, and may cause a decrease in the reaction rate or a decrease in yield of carbonic acid ester. Thus, it is preferable to partially extract the composition of deactivated forms of the dialkyl tin alkoxide catalyst from the reaction system and regenerate dialkyl tin catalyst from said composition of deactivated forms. Regeneration of said composition of deactivated forms is preferably carried out following the above-mentioned step (2) and/or step (3). There are no particular limitations on the amount of said composition of deactivated forms extracted from the reaction system. In addition, there are also no particular limitations on the amount of deactivated forms of dialkyl tin catalyst contained in said composition of deactivated forms.

Deactivated forms of dialkyl tin catalyst extracted from the reaction system are regenerated as dialkyl tin catalyst according to the method of the present embodiments as described above, and is then used as a catalyst for producing said carbonic acid ester. The regenerated dialkyl tin catalyst is preferably recycled as dialkyl tin catalyst of the above-mentioned step (4) and/or step (1).

FIG. 1 shows a flow chart of a modified process for producing carbonic acid ester that combines a process for producing carbonic acid ester and a process for producing a dialkyl tin compound, according to the present embodiments. As was previously described, all or a portion of the reaction liquid extracted from step (2) and/or step (3) of the process for producing carbonic acid ester is used as the raw material of the present reaction (namely a composition of deactivated forms of dialkyl tin catalyst). Although it was previously stated that a residue liquid is obtained in step (2), said residue liquid is used as a composition of deactivated forms of the present embodiment. At this time, the above-mentioned step (A) is carried out since the dialkyl tin alkoxide used in the carbonic acid ester production step is an alkoxide in which the group other than an alkyl group bound to tin as referred to in the present embodiments is an alkoxide group, and the pKa of a conjugated acid of said alkoxide group (namely an alcohol) is about 17. Although water and carboxylic acid ester are produced as by-products when step (A) is carried out, said by-products are preferably removed in a suitable step when carrying out the above-mentioned step. More preferably, said by-products are discharged outside the system while carrying out step (A). Alternatively, said by-products are removed outside the system in the form of gaseous components while flushing from the system for the purpose of cooling the reaction liquid following the alkyl group redistribution step. As was previously described, in the case of using an acid when carrying out step (A) in the carbonic acid ester production step using dialkyl tin alkoxide as a catalyst, there are cases in which water is formed as a by-product, and since there are also cases in which raw materials and/or products are hydrolyzed during the reaction resulting in the formation of a solid component, carboxylic acid anhydride is preferable for the compound that is reacted (acid and/or acid anhydride). In addition, in the case of reacting an acid anhydride, carboxylic acid ester originating from said acid anhydride and alkoxy group is formed as a by-product. The optimum carboxylic acid anhydride is acetic anhydride for the purpose of easily removing said carboxylic acid ester outside the system. Following completion of step (A), the alkyl group redistribution reaction of the present embodiments is carried out by heat treatment. Next, in order to recycle the resulting dialkyl tin compound as a catalyst of the carbonic acid ester production step in the form of the dialkyl tin alkoxide, a substituent of the dialkyl tin compound is converted to an alkoxy group. This substituent conversion step converts a substituent to an alkoxy group using a known method or synthesis method. For example, after obtaining dialkyl tin oxide by carrying out the above-mentioned step (I-1), an alkoxylation step explained below is carried out on said dialkyl tin oxide to obtain an alkyl tin alkoxide. The resulting alkyl tin alkoxide is then recycled to, for example, step (1) or step (4). A purification step and the like may also be added in addition to that described above.

Alkoxylation Step (One Aspect of Step (I-2))

This step is a step of reacting alcohol with the composition containing dialkyl tin oxide obtained from the previously described steps followed by removal of water generated as a by-product outside the system to obtain dialkyl tin alkoxide. This step is carried out using the same method as the previously described alkyl tin alkoxide synthesis step of obtaining alkyl tin alkoxide from dialkyl tin oxide and alcohol. Namely, this step is carried out using the above-mentioned composition containing dialkyl tin oxide instead of using dialkyl tin oxide for the raw material.

As was previously described, since the alkyl group redistribution reaction of the present embodiments is an equilibrium reaction and based on the typical properties of an equilibrium reaction, the alkyl group redistribution reaction of the present embodiments is preferably carried out according to the procedure described above using the composition of deactivated forms in which said deactivated forms have been accumulated and/or concentrated to a high concentration (for example, a composition of deactivated forms in which the content of deactivated forms, in which the number of alkyl groups bound to the tin atom of the alkyl tin compound is a number other than 2 with respect to the total number of moles of tin atoms of the alkyl tin compound contained in the composition of deactivated forms of the dialkyl tin catalyst, when represented as mol %, is 10 mol % or more, preferably 30 mol % or more and more preferably 50 mol % or more). Namely, after having produced carbonic acid ester in the carbonic acid ester production step under conditions such that the deactivated forms are within the above range, or after having recovered active catalyst from the composition of deactivated forms according to, for example, a method previously disclosed by the inventors of the present invention (see WO 2007/097388), component containing the composition of highly concentrated deactivated forms is used as the composition of deactivated forms of the present embodiments, thereby making it possible to use a dialkyl tin catalyst extremely efficiently by adding the steps of the present embodiments.

Carbonic acid esters obtained in the above-mentioned steps can be preferably used as polycarbonate raw materials, isocyanate raw materials, other chemical raw materials and as electrolyte of lithium ion batteries and the like. According to this process, since dialkyl tin catalyst can be regenerated from deactivated forms of dialkyl tin catalysts that were previously discarded, the problems of cost and waste in the production process of carbonic acid esters can be solved. Thus, the present invention is industrially extremely important.

EXAMPLES

Although the following provides a more detailed explanation of the present embodiments through examples thereof, the present embodiments are not limited to these examples alone.

Furthermore, the analytical methods used in the present embodiments are as indicated below.
<Analytical Methods>
NMR Analysis
Apparatus: JNM-A400 FT-NMR system manufactured by JEOL Ltd.
(1) Preparation of $^1$H-, $^{13}$C- and $^{119}$Sn-NMR Analysis Samples
About 0.3 g of sample solution are weighed out followed by the addition of about 0.7 g of heavy chloroform (Aldrich Corp., 99.8%) and 0.05 g of internal standard in the form of tetramethyl tin (Wako Pure Chemical Industries, Ltd., Wako Grade 1) and using the uniformly mixed solution as an NMR analysis sample.
(2) Quantitative Analysis
Quantitative analysis was carried out on the analysis sample based on a calibration curve prepared by analyzing each standard substance.

Example 1

Step (1-1): Production of Dialkyl Tin Catalyst
627 g (2.7 mol) of dibutyl tin oxide (Sankyo Organic Chemicals Co., Ltd., Japan) and 2000 g (22.7 mol) of 3-methyl-1-butanol (Kuraray Co., Ltd., Japan) were placed in a 5000 mL volumetric pear-shaped flask. The flask was connected to an evaporator (R-144, Shibata Co., Ltd., Japan) to which was connected an oil bath (OBH-24, Masuda Corp., Japan) equipped with a temperature controller, a vacuum pump (G-50A, Ulvac Inc., Japan) and a vacuum controller (VC-10S, Okano Seisakusho Co., Ltd., Japan). The purge valve outlet of this evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to about 145° C., the flask was immersed in the oil bath and rotation of the evaporator was started. After heating for about 40 minutes in the presence of atmospheric pressure nitrogen with the purge valve of the evaporator left open, distillation of 3-methyl-1-butanol containing water began. After maintaining in this state for 7 hours, the purge valve was closed, pressure inside the system was gradually reduced, and excess 3-methyl-1-butanol was distilled with the pressure inside the system at from 74 to 35 kPa. After the fraction no longer appeared, the flask was taken out of the oil bath. After allowing the flask to cool to the vicinity of room temperature (25° C.), the purge valve was opened gradually and the pressure inside the system was returned to atmospheric pressure. 1173 g of reaction liquid were obtained in the flask. Based on the results of $^{119}$Sn—, $^1$H- and $^{13}$C-NMR analyses, 1,1,3,3-tetra-n-butyl-1,3-bis(3-methylbutyloxy) distannoxane was confirmed to have been obtained at a yield of 99% based on dibutyl tin oxide. The same procedure was then repeated 12 times to obtain a total of 10345 g of 1,1,3,3-tetra-n-butyl-1,3-bis(3-methylbutyloxy) distannoxane.

Figure 2:
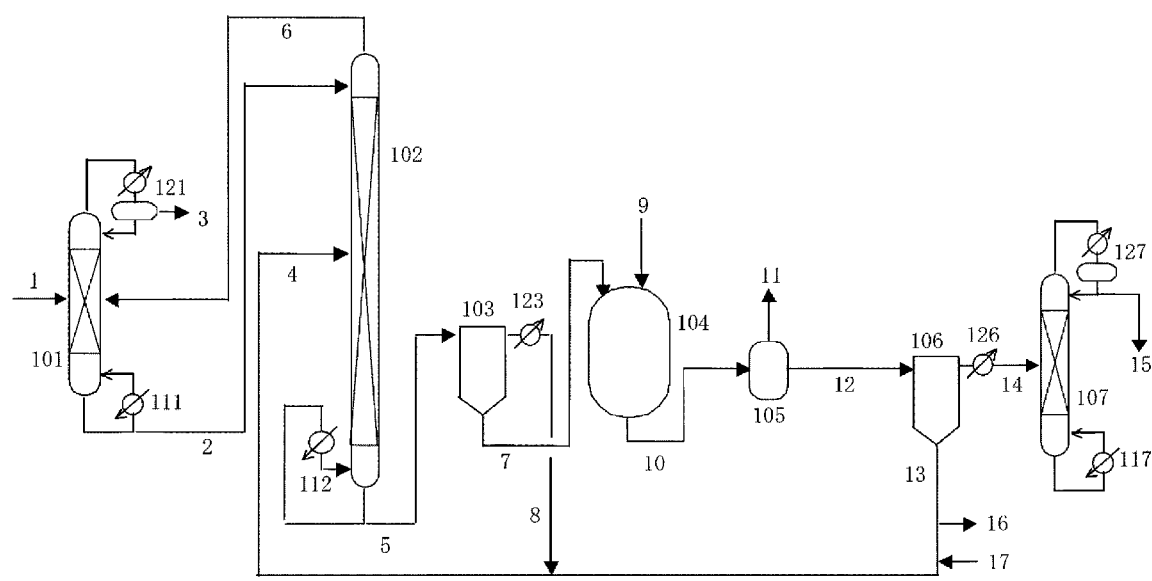
FIG. 2 illustrates a schematic drawing showing an apparatus for continuously producing carbonic acid esters using an alkyl tin catalyst composition in the present embodiment.

Step (1-2): Production of Carbonic Acid Ester and Recovery of Composition of Deactivated Forms of Dialkyl Tin Catalyst Carbonic acid ester was produced in a continuous production apparatus like that shown in FIG. 2. 1,1,3,3-Tetra-n-butyl-1,3-bis(3-methylbutyloxy) distannoxane produced in the manner described above was supplied at the rate of 4388 g/hr from a transfer line 4 into a column-type reaction vessel 102 packed with Metal Gauze CY Packing (Sulzer Chemtech Ltd., Switzerland) and having an inner diameter of 151 mm and effective length of 5040 mm, and 3-methyl-1-butanol purified with a distillation column 101 was supplied at the rate of 14953 g/hr from a transfer line 2. The liquid temperature inside reaction vessel 102 was controlled to 160° C. by a heater and a reboiler 112, and the pressure was adjusted to about 120 kPa-G with a pressure control valve. The residence time in the reaction vessel was about 17 minutes. 3-methyl-1-butanol containing water at the rate of 15037 g/hr from the top of the reaction vessel via a transfer line 6, and 3-methyl-1-butanol at the rate of 825 g/hr via feed line 1, were pumped to distillation column 101 packed with Metal Gauze CY Packing and provided with a reboiler 111 and a condenser 121 to carry out distillative purification. In the top of distillation column 101, a fraction containing a high concentration of water was condensed by condenser 121 and recovered from a recovery line 3. Purified 3-methyl-1-butanol was pumped to column-type reaction vessel 102 via transfer line 2 located in the bottom of distillation column 101. An alkyl tin alkoxide catalyst composition containing di-n-butyl-bis(3-methylbutyloxy) tin and 1,1,3,3-tetra-n-butyl-1,3-bis(3-methylbutyloxy) distannoxane was obtained from the bottom of column-type reaction vessel 102, and supplied to a thin film evaporator 103 (Kobelco Eco-Solutions Co., Ltd., Japan) via a transfer line 5. The 3-methyl-1-butanol was distilled off in thin film evaporator 103 and returned to column-type reaction vessel 102 via a condenser 123, a transfer line 8 and transfer line 4. The alkyl tin alkoxide catalyst composition was pumped from the bottom of thin film evaporator 103 via a transfer line 7 and supplied to an autoclave 104 while adjusting the flow rate of di-n-butyl-bis(3-methylbutyloxy) tin and 1,1,3,3-tetra-n-butyl-1,3-bis(3-methylbutyloxy) distannoxane to about 5130 g/hr. Carbon dioxide was supplied to the autoclave by a transfer line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the alkyl tin alkoxide catalyst composition was carried out to obtain a reaction liquid containing bis(3-methylbutyl) carbonate. This reaction liquid was transferred to a decarbonization tank 105 via a transfer line 10 and a control valve to remove residual carbon dioxide, and the carbon dioxide was recovered from a transfer line 11. Subsequently, the reaction liquid was transferred to a thin film evaporator (Kobelco Eco-Solutions Co., Ltd., Japan) 106 set to about 142° C. and about 0.5 kPa via a transfer line 12 and supplied while adjusting the flow rate of 1,1,3,3-tetra-n-butyl-1,3-bis(3-methylbutyloxy) distannoxane to about 4388 g/hr to obtain a fraction containing bis(3-methylbutyl) carbonate. On the other hand, the evaporation residue was circulated to column-type reaction vessel 102 via transfer line 13 and transfer line 4 while adjusting the flow rate of 1,1,3,3-tetrabutyl-1,3-bis(3-methylbutyloxy) distannoxane to about 4388 g/hr. The fraction containing bis(3-methylbutyl) carbonate was supplied to a distillation column 107 packed with Metal Gauze CY packing and equipped with a reboiler 117 and a condenser 127 via a condenser 126 and a transfer line 14 at the rate of 959 g/hr followed by distillative purification to obtain 99 wt % bis(3-methylbutyl) carbonate from a recovery line 16 at the rate of 944 g/hr. When the alkyl tin alkoxide catalyst composition of a transfer line 13 was analyzed by $^{119}$Sn—, $^1$H- and $^{13}$C-NMR analysis, it was found to contain 1,1,3,3-tetra-n-butyl-1,3-bis(3-methylbutyloxy) distannoxane but not contain di-n-butyl-bis(3-methylbutyloxy) tin. After carrying out the above-mentioned continuous operation for about 240 hours, alkyl tin alkoxide catalyst composition was extracted from an extraction line 16 at the rate of 18 g/hr, 1,1,3,3-tetra-n-butyl-1,3-bis(3-methylbutyloxy) distannoxane produced according to the above process was supplied from a feed line 17 at the rate of 18 g/hr, and about 120 g of a catalyst composition of 1,1,3,3-tetra-n-butyl-1,3-bis(3-methylbutyloxy) distannoxane was extracted from extraction line 16. As a result of analysis by $^{119}$Sn-NMR, in addition to containing about 60 wt % of 1,1,3,3-tetra-n-butyl-1,3-bis(3-methylbutyloxy) distannoxane, tri-n-butyl(3-methylbutyloxy) tin and a plurality of NMR shifts of deactivated components of 1,1,3,3-tetra-n-butyl-1,3-bis(3-methylbutyloxy) distannoxane were observed at from −240 to −605 ppm. This catalyst composition was used as a composition of deactivated forms.

Step (1-3): Separation of Tri-n-butyl(3-methylbutyloxy) Tin 120 g of the composition of deactivated forms obtained in step (1-2) were transferred to a 500 mL pear-shaped flask. A three-way valve, a distillation column packed with Helipack No. 3 and measuring 45 cm in length, a fractionation head equipped with a reflux condenser connected to a distillate collector and a thermometer were attached to the flask, and the inside of the vessel was replaced with nitrogen in a vacuum. The nitrogen inside the vessel was returned to atmospheric pressure and the flask was immersed in an oil bath heated to about 190° C. After about 20 minutes, the pressure inside the vessel was gradually reduced and the distilled components were recovered when the temperature of the composition of deactivated forms reached about 180° C. Finally, distillation was terminated when the pressure inside the vessel reached about 0.01 kPa. The distillate and residue inside the flask were subjected to $^1$H- and $^{119}$Sn-NMR measurement. The distillate was tri-n-butyl(3-methylbutyloxy) tin. The residue inside the flask contained 76.5 wt % of 1,1,3,3-tetra-n-butyl-1,3-bis(3-methylbutyloxy) distannoxane, and according to $^{119}$Sn-NMR, was a mixture of organic tin compounds containing tin atoms demonstrating a plurality of chemical shifts at from −240 to −605 ppm. There were 25.5 g of the resulting distillate and 94.0 g of residue inside the flask.

Step (1-4): Substituent Exchange Reaction of Deactivated Forms of Dialkyl Tin Catalyst 24.7 g of tri-n-butyl(3-methylbutyloxy) tin obtained in step (1-3) were placed in a 300 mL pear-shaped flask under a nitrogen atmosphere followed by the addition of 34.5 g of acetic anhydride (Aldrich Corp., U.S.) and stirring for 1 hour at 25° C. When the solution was sampled and subjected to analysis by gas chromatography, isoamyl acetate was confirmed to have been formed. A fractionation head equipped with a reflux condenser connected to a distillate collector and a thermometer were attached to the flask, and after replacing the inside of the flask with nitrogen in a vacuum, the flask was immersed in an oil bath heated to 50° C. The pressure inside the vessel was gradually reduced, and the isoamyl acetate and excess acetic anhydride were distilled off to obtain 22.8 g of a residue inside the flask. When the residue was subjected to $^1$H- and $^{119}$Sn-NMR measurement, the residue was determined to be tri-n-butyl acetoxy tin.

On the other hand, 93.2 g of the residue containing 76.5 wt % of 1,1,3,3-tetra-n-butyl-1,3-bis(3-methylbutyloxy) distannoxane obtained in step (1-1) were placed in a 500 mL metal pressure vessel (Model TSV-N2, Taiatsu Techno Corp., Japan) followed by adding 150.0 g of acetic anhydride and stirring. The metal pressure vessel was then immersed in an oil bath heated to 200° C. and heated for 3 hours. After allowing the metal pressure vessel to cool to the vicinity of room temperature (about 25° C.), the contents were transferred to a 500 mL pear-shaped flask. A fractionation head equipped with a reflux condenser connected to a distillate collector and a thermometer were attached to the flask and the inside of the flask was replaced with nitrogen in a vacuum followed by immersing the flask in an oil bath heated to 50° C. The pressure inside the vessel was gradually reduced and the excess acetic anhydride and the like were distilled off to obtain 103.3 g of residue in the flask. When the residue was subjected to $^1$H- and $^{119}$Sn-NMR measurement, the residue was determined to be a mixture containing di-n-butyl diacetoxy tin and n-butyl triacetoxy tin, and the content of di-n-butyl acetoxy tin in the residue was 75.4 wt % while the content of n-butyl triacetoxy tin was 24.5 wt %. This mixture was mixed with the previously obtained tri-n-butyl acetoxy tin and used as the raw material of the subsequent step (1-5).

Step (1-5): Alkyl Group Redistribution Reaction 125.3 g of the mixture obtained in step (1-4) were placed in a 200 mL metal pressure vessel (Model TSV-N2, Taiatsu Techno Corp., Japan) under a nitrogen atmosphere. The metal pressure vessel was immersed in an oil bath heated to 250° C. and heated for 30 minutes. After allowing the metal pressure vessel to cool to the vicinity of room temperature, 124.5 g of reaction liquid were recovered. When $^1$H- and $^{119}$Sn-NMR measurement were carried out on the reaction liquid, the reaction liquid was determined to be a mixture containing di-n-butyl diacetoxy tin and n-butyl triacetoxy tin, and the content of di-n-butyl diacetoxy tin in the mixture was 96.3 wt %.

Step (1-6): Alkoxylation of Dialkyl Tin Compounds 122.1 g of the reaction liquid obtained in step (1-5) were placed in a 500 mL volumetric pear-shaped flask and immersed in an oil bath heated to 50° C. A white precipitate formed when 300 mL of 0.1 mol/L aqueous potassium hydroxide solution (Wako Pure Chemical Industries, Ltd.) were added while stirring the contents thereof. The mixture was filtered with filter paper to recover 82.1 g of a white precipitate.

81.1 g of the white precipitate and 238.0 g (2.70 mol) of 3-methyl-1-butanol were placed in a 500 mL volumetric pear-shaped flask. The flask was attached to a rotary evaporator to which was connected an oil bath equipped with a temperature controller, a vacuum pump and a vacuum controller. The purge valve outlet of this evaporator was connected to a line containing nitrogen gas flowing at atmospheric pressure. After replacing the inside of the system with nitrogen, the temperature of the oil bath was set to 146° C., the flask was immersed in the oil bath and rotation of the rotary evaporator was started. After distilling off a low boiling point component for about 7 hours in the presence of nitrogen at atmospheric pressure with the purge valve of the rotary evaporator open, the pressure inside the system was gradually reduced, and the remaining low boiling point component was distilled off at an internal pressure of from 76 to 30 kPa. Once distillation of the low boiling point component was no longer observed, the flask was taken out of the oil bath and allowed to cool. 107.0 g of a residue liquid were obtained in the flask. Based on the results of $^1$H-, $^{13}$C- and $^{119}$Sn-NMR analyses, the content of 1,1,3,3-tetra-n-butyl-1,3-bis(3-methylbutyloxy) distannoxane in the residue liquid in the flask was found to be 96.4 wt %.

Step (1-7): Use of Regenerated Dialkyl Tin Catalyst in Carbonic Acid Ester

Production Step

A solution containing 96.5 wt % of the 1,1,3,3-tetra-n-butyl-1,3-bis-(3-methylbutyloxy) distannoxane obtained in step (1-6) was supplied from feed line 17 at the rate of 18 g/hr while extracting the dialkyl tin catalyst composition from extraction line 16 at the rate of 18 g/hr in the carbonic acid ester production step explained in step (1-2). 99 wt % bis(3-methylbutyl) carbonate was recovered from recovery line 15 at the rate of 944 g/hr, and effects of the use of the dialkyl tin catalyst produced in step (1-6) on the carbonic acid ester production step were not confirmed.

Example 2

Step (2-1): Substituent Exchange Reaction of Deactivated Forms of Dialkyl Tin Catalyst 125 g of a composition of deactivated forms obtained by the same method as step (1-2) of Example 1 were placed in a 500 mL pear-shaped flask under a nitrogen atmosphere followed by adding 145.0 g of acetic anhydride and stirring for 1 hour at 25° C. After attaching a fractionation head equipped with a reflux condenser connected to a distillate collector and a thermometer to the flask and replacing the inside of the flask with nitrogen in a vacuum, the flask was immersed in an oil bath heated to 50° C. The pressure inside the vessel was gradually reduced and excess acetic anhydride was distilled off to obtain 125.9 g of a residue inside the flask. When $^1$H- and $^{119}$Sn-NMR measurement were carried out on the residue, the residue was found to be a mixture of tri-n-butyl acetoxy tin and di-n-butyl diacetoxy tin, and according to $^{119}$Sn-NMR, organic tin compounds containing tin atoms demonstrating a plurality of chemical shifts at from −240 to −605 ppm. The content of tri-n-butyl acetoxy tin in the mixture was 21.1 wt % while the content of di-n-butyl diacetoxy tin was 63.7 wt %.

Step (2-2): Alkyl Group Redistribution Reaction 123.7 g of the mixture obtained in step (2-1) were placed in a 200 mL metal pressure vessel (Model TSV-N2, Taiatsu Techno Corp., Japan) under a nitrogen atmosphere. The metal pressure vessel was immersed in an oil bath heated to 250° C. and heated for 30 minutes. After allowing the metal pressure vessel to cool to the vicinity of room temperature, 122.9 g of reaction liquid were recovered. When $^1$H- and $^{119}$Sn-NMR measurement were carried out on the reaction liquid, the reaction liquid was found to be a mixture of organic tin compounds containing di-n-butyl diacetoxy tin, tri-n-butyl acetoxy tin and 1,1,3,3-tetra-n-butyl-1,3-diacetoxy distannoxane, and the content of di-n-butyl diacetoxy tin was 63.7 wt %, the content of tri-n-butyl acetoxy tin was about 1 wt %, and the content of 1,1,3,3-tetra-n-butyl-1,3-diacetoxy distannoxane was 31.4 wt %.

Step (2-3): Alkoxylation of Dialkyl Tin Compounds 118.6 g of a solution containing 91.0 wt % of 1,1,3,3-tetra-n-butyl-1,3-bis(3-methylbutyloxy) distannoxane were obtained by carrying out the same method as Step (1-6) of Example 1 with the exception of using 121.3 g of the mixture obtained in Step (2-2), 290 mL of 0.1 mol/L aqueous potassium hydroxide solution, and 220.3 g of 3-methyl-1-butanol.

Example 3

Step (3-1): Substituent Exchange Reaction of Deactivated Forms of Dialkyl Tin Catalyst 130 g of a composition of deactivated forms obtained using the same method as step (1-2) of Example 1 and 100 g of toluene (guaranteed reagent, Wako Pure Chemical Industries, Ltd., Japan) were placed in a 500 mL pear-shaped flask. A Dean-Stark tube, Dimroth condenser and three-way valve were attached to the pear-shaped flask. The three-way valve was connected to a line through which nitrogen gas was flowing at normal pressure.

The flask was immersed in oil bath pre-heated to 140° C. followed by refluxing the toluene and allowing hydrogen chloride gas to flow into the flask at about 150 mL/min. Water was recovered in the Dean-Stark tube together with refluxing the toluene, and the reaction was completed after carrying out for 16 hours. After allowing the flask to cool to the vicinity of room temperature, the inside of the flask was purged with nitrogen for 3 hours. Toluene was distilled off from the resulting solution to obtain 120.4 g of solution. When $^1$H- and $^{119}$Sn-NMR measurement were carried out on this solution, the solution was found to be a mixture of tri-n-butylchloro tin and di-n-butyldichloro tin, and the content of tri-n-butylchloro tin was 17.1 wt % while the content of di-n-butyldichloro tin was 64.2 wt %.

Step (3-2): Alkyl Group Redistribution Reaction 118.2 g of the mixture obtained in step (3-1) were placed in a 300 mL Teflon (™) double-walled vessel (Model TAF-SR, Taiatsu Techno Corp., Japan) under a nitrogen atmosphere. The vessel was immersed in an oil bath heated to 250° C. and heated for 15 hours. After allowing the vessel to cool to the vicinity of room temperature, 116.9 g of reaction liquid were recovered. When $^1$H- and $^{119}$Sn-NMR measurement were carried out on the reaction liquid, the reaction liquid was found to be a solution containing 93.1 wt % di-n-butyldichloro tin.

Step (3-3): Alkoxylation of Dialkyl Tin Compounds 119.1 g of a solution containing 98.0 wt % of 1,1,3,3-tetra-n-butyl-1,3-bis(3-methylbutyloxy) distannoxane were obtained by carrying out the same method as step (1-6) of Example 1 with the exception of using 115.9 g of the solution obtained in step (3-2) instead of the solution obtained in step (1-5), and using 330 mL of 0.1 mol/L aqueous potassium hydroxide solution and 292.2 g of 3-methyl-1-butanol.

Example 4

Step (4-1): Dealkylation Reaction 150.0 g of the composition of deactivated forms obtained using the same method as step (1-2) of Example 1 and 120.3 g of 1-decanol (guaranteed reagent, Wako Pure Chemical Industries, Ltd., Japan) were placed in a 500 mL pear-shaped flask. A Dean-Stark tube, a Dimroth condenser and a three-way valve were attached to the pear-shaped flask. The three-way valve was connected to a line through which nitrogen gas was flowing at normal pressure.

The flask was immersed in an oil bath pre-heated to 250° C. followed by refluxing the 1-decanol and allowing hydrogen chloride gas to flow into the flask at about 150 mL/min. Water was recovered in the Dean-Stark tube together with refluxing the 1-decanol, and the reaction was completed after carrying out for 15 hours. After allowing the flask to cool to the vicinity of room temperature, the inside of the flask was purged with nitrogen for 3 hours. 1-decanol was distilled off from the resulting solution to obtain 135.8 g of solution. When $^1$H- and $^{119}$Sn-NMR measurement were carried out on this solution, the solution was found to contain 81.1 wt % of di-n-butyldichloro tin.

Step (4-2): Separation of Dialkyl Tin Compounds 133.2 g of the mixture obtained in step (4-1) were placed in a 200 mL pear-shaped flask, and a fractionation head equipped with a reflux condenser connected to a distillate collector and a thermometer were attached to the flask. After replacing the inside of the vessel with nitrogen in a vacuum, the flask was immersed in an oil bath heated to 100° C. The pressure inside the vessel was gradually reduced to a final pressure of 1.3 kPa to recover 26.3 g of distillate and 106.3 g of residue. When $^1$H- and $^{119}$Sn-NMR measurement were carried out on the residue, the distillate was found to be di-n-butyldichloro tin.

Step (4-3): Alkoxylation of Dialkyl Tin Compounds 106.1 g of 1,1,3,3-tetra-n-butyl-1,3-bis(3-methylbutyloxy) distannoxane were obtained by carrying out the same method as step (1-6) of Example 1 with the exception of using 105.5 g of the di-n-butyldichloro tin obtained in step (4-2) instead of the solution obtained in step (1-3) and using 320 mL of 0.1 mol/L aqueous potassium hydroxide solution and 287.8 g of 3-methyl-1-butanol.

Example 5

Step (5-1): Substituent Exchange Reaction of Deactivated Forms on Dialkyl Tin Catalyst 201.5 g of a mixture of tri-n-butyl acetoxy tin, di-n-butyl diacetoxy tin and, according to $^{119}$Sn-NMR, organic tin compounds containing tin atoms demonstrating a plurality of chemical shifts at from −240 to −605 ppm, was obtained by carrying out the same method as step (2-1) of Example 2 with the exception of 200 g of a composition of deactivated forms obtained using the same method as step (1-2) of Example 1, and using 305.2 g of a mixture of 182.9 g of acetic acid and 124.4 g of acetic anhydride instead of 145.0 g of acetic anhydride. The content of tri-n-butyl acetoxy tin in this mixture was 20.1 wt %, while the content of di-n-butyl diacetoxy tin was 64.1 wt %.

Step (5-2): Alkyl Group Redistribution Reaction 199.3 g of a mixture containing di-n-butyl diacetoxy tin, tri-n-butyl acetoxy tin and 1,1,3,3-tetra-n-butyl-1,3-diacetoxy distannoxane was obtained by carrying out the same method as step (2-2) of Example 2 with the exception of using 200.1 g of the mixture obtained in step (5-1) instead of the mixture obtained in step (2-1). The content of di-n-butyl diacetoxy tin in this mixture was 63.7 wt %, the content of tri-n-butyl acetoxy tin was about 1 wt %, and the content of 1,1,3,3-tetra-n-butyl-1,3-diacetoxy distannoxane was 32.3 wt %.

Step (5-3): Alkoxylation of Dialkyl Tin Compounds 184.7 g of a solution containing 95.6 wt % of 1,1,3,3-tetra-n-butyl-1,3-bis(3-methylbutyloxy) distannoxane were obtained by carrying out the same method as step (1-4) of Example 1 with the exception of using 198.3 g of the mixture obtained in step (5-2), 360 mL of 0.1 mol/L aqueous potassium hydroxide solution and 544.3 g of 3-methyl-1-butanol.

Example 6

Step (6-1): Dealkylation Reaction 180 g of a composition of deactivated forms obtained using the same method as step (1-2) of Example 1 were placed in a 500 mL pear-shaped flask in the presence of a nitrogen atmosphere followed by adding 164.6 g of acetic acid and 280.0 g of acetic anhydride. The flask was immersed in an oil bath heated to 155° C. and then stirred for 5 hours while refluxing the solution. After allowing the flask to cool to room temperature, a fractionation head equipped with a reflux condenser connected to a distillate collector and a thermometer were attached to the flask, and the inside of the flask was replaced with nitrogen in a vacuum. After immersing the flask in an oil bath heated to 50° C., the pressure inside the vessel was gradually reduced and excess acetic acid and acetic anhydride were distilled off to obtain 181.5 g of a residue inside the flask. When $^1$H- and $^{119}$Sn-NMR measurement were carried out on this residue, the residue was found to contain 84.8 wt % of di-n-butyl diacetoxy tin.

Step (6-2): Separation of Dialkyl Tin Compounds 180.0 g of the solution containing 84.8 wt % di-n-butyl diacetoxy tin obtained in step (6-1) were placed in a 300 mL pear-shaped flask, and a fractionation head equipped with a reflux condenser connected to a distillate collector and a thermometer were attached to the flask. After replacing the inside of the flask with nitrogen in a vacuum, the flask was immersed in an oil bath heated to 180° C. The pressure inside the vessel was gradually reduced to a final pressure of 0.01 kPa and 150.3 g of distillate were recovered. When $^1$H- and $^{119}$Sn-NMR measurements were carried out on this distillate, the distillate was found to be di-n-butyl diacetoxy tin.

Step (6-3): Regeneration of Dialkyl Tin Catalyst from Dialkyl Tin Compounds 130.8 g of 1,1,3,3-tetra-n-butyl-1,3-bis(3-methylbutyloxy) distannoxane were obtained by carrying out the same method as step (1-6) of Example 1 with the exception of using 149.1 g of the di-n-butyl diacetoxy tin obtained in step (6-2) instead of the reaction liquid obtained in step (1-5), and using 350 mL of 0.1 mol/L aqueous potassium hydroxide solution and 350.9 g of 3-methyl-1-butanol.

Example 7

Step (7-1): Production of Dialkyl Tin Catalyst 972 g (2.7 mol) of di-n-octyl tin oxide (Sankyo Organic Chemicals Co., Ltd., Japan) and 2100 g (23.9 mol) of 3-methyl-1-butanol were placed in a 5000 mL volumetric pear-shaped flask. The flask was connected to an evaporator to which was connected an oil bath equipped with a temperature controller, a vacuum pump and a vacuum controller. The purge valve outlet of the evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to about 145° C., the flask was immersed in the oil bath and rotation of the evaporator was started. After heating for about 40 minutes in the presence of atmospheric pressure nitrogen with the purge valve of the evaporator left open, distillation of 3-methyl-1-butanol containing water began. After maintaining in this state for 7 hours, the purge valve was closed, pressure inside the system was gradually reduced, and excess 3-methyl-1-butanol was distilled with the pressure inside the system at from 74 to 35 kPa. After the fraction no longer appeared, the flask was taken out of the oil bath. After allowing the flask to cool to the vicinity of room temperature (25° C.), the purge valve was opened gradually and the pressure inside the system was returned to atmospheric pressure. 1176 g of reaction liquid were obtained in the flask. Based on the results of $^{119}$Sn-, $^1$H- and $^{13}$C-NMR analyses, 1,1,3,3-tetra-n-butyl-1, 3-bis(3-methylbutyloxy) distannoxane was confirmed to have been obtained at a yield of 99% based on the di-n-octyl tin oxide. The same procedure was then repeated 12 times to obtain a total of 14120 g of 1,1,3,3-tetra-n-octyl-1,3-bis(3-methylbutyloxy) distannoxane.

Step (7-2): Production of Carbonic Acid Ester and Recovery of Composition of Deactivated Forms of Dialkyl Tin Catalyst Carbonic acid ester was produced in a continuous production apparatus like that shown in FIG. 2. 1,1,3,3-Tetra-n-octyl-1,3-bis(3-methylbutyloxy) distannoxane produced in the manner described above was supplied at the rate of 5887 g/hr from transfer line 4 into column-type reaction vessel 102 packed with Metal Gauze CY Packing (Sulzer Chemtech Ltd., Switzerland) and having an inner diameter of 151 mm and effective length of 5040 mm, and 3-methyl-1-butanol purified with distillation column 101 was supplied at the rate of 14953 g/hr from transfer line 2. The liquid temperature inside reaction vessel 102 was controlled to 160° C. by a heater and reboiler 112, and the pressure was adjusted to about 120 kPa-G with a pressure control valve. The residence time in the reaction vessel was about 17 minutes. 3-methyl-1-butanol containing water at the rate of 15037 g/hr from the top of the reaction vessel via transfer line 6, and 3-methyl-1-butanol at the rate of 824 g/hr via feed line 1, were pumped to distillation column 101 packed with Metal Gauze CY Packing and provided with reboiler 111 and condenser 121 to carry out distillative purification. In the top of distillation column 101, a fraction containing a high concentration of water was condensed by condenser 121 and recovered from recovery line 3. Purified 3-methyl-1-butanol was pumped to column-type reaction vessel 102 via transfer line 2 located in the bottom of distillation column 101. An alkyl tin alkoxide catalyst composition containing di-n-octyl-bis(3-methylbutyloxy) tin and 1,1,3,3-tetra-n-octyl-1,3-bis(3-methylbutyloxy) distannoxane was obtained from the bottom of column-type reaction vessel 102, and supplied to thin film evaporator 103 via transfer line 5. The 3-methyl-1-butanol was distilled off in thin film evaporator 103 and returned to column-type reaction vessel 102 via condenser 123, transfer line 8 and transfer line 4. The alkyl tin alkoxide catalyst composition was pumped from the bottom of thin film evaporator 103 via transfer line 7 and supplied to autoclave 104 while adjusting the flow rate of di-n-octyl-bis(3-methylbutyloxy) tin and 1,1,3,3-tetra-n-octyl-1,3-bis(3-methylbutyloxy) distannoxane to about 6627 g/hr. Carbon dioxide was supplied to the autoclave by transfer line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the alkyl tin alkoxide catalyst composition was carried out to obtain a reaction liquid containing bis(3-methylbutyl) carbonate. The reaction liquid was transferred to decarbonization tank 105 via transfer line 10 and a control valve to remove residual carbon dioxide, and the carbon dioxide was recovered from transfer line 11. Subsequently, the reaction liquid was transferred to thin film evaporator 106 set to about 142° C. and about 0.5 kPa via transfer line 12 and supplied while adjusting the flow rate of 1,1,3,3-tetra-n-octyl-1,3-bis(3-methylbutyloxy) distannoxane to about 5887 g/hr to obtain a fraction containing bis(3-methylbutyl) carbonate. On the other hand, the evaporation residue was circulated to column-type reaction vessel 102 via transfer line 13 and transfer line 4 while adjusting the flow rate of 1,1,3,3-tetra-n-octyl-1,3-bis(3-methylbutyloxy) distannoxane to about 5887 g/hr. The fraction containing bis(3-methylbutyl) carbonate was supplied to distillation column 107 packed with Metal Gauze CY packing and equipped with reboiler 117 and condenser 127 via condenser 126 and transfer line 14 at the rate of 959 g/hr followed by distillative purification to obtain 99 wt % bis(3-methylbutyl) carbonate from recovery line 15 at the rate of 944 g/hr. When the alkyl tin alkoxide catalyst composition of transfer line 13 was analyzed by $^{119}$Sn-, $^{1}$H- and $^{13}$C-NMR analysis, it was found to contain 1,1,3,3-tetra-n-octyl-1,3-bis(3-methylbutyloxy) distannoxane but not contain di-n-octyl-bis(3-methylbutyloxy) tin. After carrying out the above-mentioned continuous operation for about 240 hours, alkyl tin alkoxide catalyst composition was extracted from extraction line 16 at the rate of 18 g/hr, 1,1,3,3-tetra-n-octyl-1,3-bis(3-methylbutyloxy) distannoxane produced according to the above process was supplied from feed line 17 at the rate of 18 g/hr, and 200 g of a composition of deactivated forms of 1,1,3,3-tetra-n-octyl-1,3-bis(3-methylbutyloxy) distannoxane was extracted from extraction line 16. As a result of analysis by $^{119}$Sn-NMR, in addition to containing about 60 wt % of 1,1,3,3-tetra-n-octyl-1,3-bis(3-methylbutyloxy) distannoxane, tri-n-octyl(3-methylbutyloxy) tin and a plurality of NMR shifts of deactivated components of 1,1,3,3-tetra-n-octyl-1,3-bis(3-methylbutyloxy) distannoxane were observed at from −240 to −605 ppm. This catalyst composition was used as a composition of deactivated forms.

Step (7-3): Substituent Exchange Reaction of Deactivated Forms of Dialkyl Tin Catalyst 201.2 g of a mixture of tri-n-octyl acetoxy tin, di-n-octyl diacetoxy tin and, according to $^{119}$Sn-NMR, organic tin compounds containing tin atoms demonstrating a plurality of chemical shifts at from −240 to −605 ppm, were obtained by carrying out the same method as step (2-1) of Example 2 with the exception of using 200 g of the composition of deactivated forms obtained in step (7-2) instead of the composition of deactivated forms obtained in step (1-2) and using 231.0 g of acetic anhydride. The content of tri-n-octyl acetoxy tin in the mixture was 23.4 wt %, while the content of di-n-octyl diacetoxy tin was 62.8 wt %.

Step (7-4): Alkyl Group Redistribution Reaction 197.3 g of a reaction liquid were recovered by carrying out the same method as step (2-1) of Example 2 with the exception of using 199.3 g of the mixture obtained in step (7-3) instead of the mixture obtained in step (2-1). When $^{1}$H- and $^{119}$Sn-NMR measurements were carried out on this reaction liquid, the reaction liquid was found to be a mixture containing di-n-octyl diacetoxy tin, tri-n-octyl acetoxy tin and 1,1,3,3-tetra-n-octyl-1,3-diacetoxy distannoxane, and the content of di-n-octyl diacetoxy tin was 62.5 wt %, the content of tri-n-octyl acetoxy tin was about 3 wt %, and the content of 1,1,3,3-tetra-n-octyl-1,3-diacetoxy distannoxane was 32.0 wt %.

Step (7-5): Alkoxylation of Dialkyl Tin Compounds 181.0 g of a solution containing 95.2 wt % of 1,1,3,3-tetra-n-octyl-1,3-bis(3-methylbutyloxy) distannoxane were obtained by carrying out the same method as step (1-6) of Example 1 with the exception of using 194.4 g of the mixture obtained in step (7-4) instead of the mixture obtained in step (1-5), and using 290 mL of 0.1 mol/L aqueous potassium hydroxide solution and 297.6 g of 3-methyl-1-butanol.

Example 8

Step (8-1): Dealkylation Reaction 225.7 g of a mixture containing 85.8 wt % of di-n-octyl diacetoxy tin were obtained by carrying out the same method as step (6-1) of Example 6 with the exception of using 230 g of a composition of deactivated forms obtained using the same method as step (7-2) of Example 7 instead of the composition of deactivated forms obtained in step (1-2) of Example 1, and using 158.0 g of acetic acid and 283.5 g of acetic anhydride.

Step (8-2): Separation of Dialkyl Forms 191.9 g of a distillate were obtained by carrying out the same method as step (6-2) of Example 6 with the exception of using 224.1 g of the mixture containing 85.8 wt % di-n-octyl diacetoxy tin obtained in step (8-1). When $^1$H- and $^{119}$Sn-NMR measurements were carried out on this distillate, the distillate was found to be di-n-octyl diacetoxy tin.

Step (8-3): Alkoxylation of Dialkyl Tin Compounds 175.4 g of 1,1,3,3-tetra-n-octyl-1,3-bis(3-methylbutyloxy) distannoxane were obtained by carrying out the same method as step (1-6) of Example 1 with the exception of using 190.0 g of the di-n-octyl diacetoxy tin obtained in step (8-2) instead of the mixture obtained in step (1-5) of Example 1, and using 334 mL of 0.1 mol/L aqueous potassium hydroxide solution and 280.6 g of 3-methyl-1-butanol.

Example 9

Step (9-1): Dealkylation Reaction 191.4 g of a mixture containing 86.2 wt % of di-n-octyl diacetoxy tin were obtained by carrying out the same method as step (6-1) of Example 6 with the exception of using 195 g of a composition of deactivated forms obtained using the same method as step (7-2) of Example 7 instead of the composition of deactivated forms obtained in step (1-2) of Example 1 and using 271.1 g of acetic anhydride (but not using acetic acid).

Step (9-2): Separation of Dialkyl Forms 184.6 g of a distillate were obtained by carrying out the same method as step (6-2) of Example 6 with the exception of using 190.2 g of a mixture containing 86.2 wt % of the di-n-octyl diacetoxy tin obtained in step (9-1) and making the temperature 200° C. When $^1$H- and $^{119}$Sn-NMR measurements were carried out on this distillate, the distillate was found to be di-n-octyl diacetoxy tin.

Step (9-3): Alkoxylation of Dialkyl Tin Compounds 166.7 g of 1,1,3,3-tetra-n-octyl-1,3-bis(3-methylbutyloxy) distannoxane were obtained by carrying out the same method as step (1-6) of Example 1 with the exception of using 181.2 g of the di-n-octyl diacetoxy tin obtained in step (9-2), and using 292 mL of 0.1 mol/L aqueous potassium hydroxide solution and 266.7 g of 3-methyl-1-butanol.

Example 10

Step (10-1): Substituent Exchange Reaction of Deactivated Forms of Dialkyl Tin Catalyst 221.3 g of a mixture of tri-n-octyl acetoxy tin, di-n-octyl diacetoxy tin and, according to $^{119}$Sn-NMR, organic tin compounds containing tin atoms demonstrating a plurality of chemical shifts at from −240 to −605 ppm was obtained by carrying out the same method as step (7-3) of Example 7 with the exception of using 220 g of a composition of deactivated forms obtained using the same method as step (7-2) of Example 7, and using 403.2 g of a mixture of 150.1 g of acetic acid and 255.4 g of acetic anhydride instead of acetic anhydride. The content of tri-n-octyl acetoxy tin in the mixture was 22.8 wt % while the content of di-n-octyl diacetoxy tin was 62.2 wt %.

Step (10-2): Alkyl Group Redistribution Reaction 218.8 g of a reaction liquid were obtained by carrying out the same method as step (7-4) of Example 7 with the exception of using 220.1 g of the mixture obtained in step (10-1) instead of the mixture obtained in step (7-3) of Example 7. When $^1$H- and $^{119}$Sn-NMR measurements were carried out on this reaction liquid, the reaction liquid was found to be a mixture containing di-n-octyl diacetoxy tin, tri-n-octyl acetoxy tin and 1,1,3,3-tetra-n-octyl-1,3-diacetoxy distannoxane, and the content of di-n-octyl diacetoxy tin was 62.7 wt %, the content of tri-n-octyl acetoxy tin was about 3 wt %, and the content of 1,1,3,3-tetra-n-octyl-1,3-diacetoxy distannoxane was 31.8 wt %.

Step (10-3): Alkoxylation of Dialkyl Tin Compounds 200.4 g of a solution containing 95.2 wt % of 1,1,3,3-tetra-n-octyl-1,3-bis(3-methylbutyloxy) distannoxane were obtained by carrying out the same method as step (1-6) of Example 1 with the exception of using 215.8 g of the mixture obtained in step (10-2) instead of the mixture obtained in step (1-5) of Example 1, and using 277 mL of 0.1 mol/L aqueous potassium hydroxide solution and 328.5 g of 3-methyl-1-butanol.

Example 11

Step (11-1): Separation of Tri-n-octyl (3-Methylbutyloxy) Tin 130 g of a composition of deactivated forms obtained using the same method as step (7-2) of Example 7 were placed in a 500 mL pear-shaped flask, a three-way valve, a distillation column packed with Helipack No. 3 and measuring 45 cm in length, a fractionation head equipped with a reflux condenser connected to a distillate collector and a thermometer were attached to the flask, and the inside of the vessel was replaced with nitrogen in a vacuum. The nitrogen inside the vessel was returned to atmospheric pressure and the flask was immersed in an oil bath heated to about 230° C. After about 20 minutes, the pressure inside the vessel was gradually reduced and the distilled components were recovered when the temperature of the composition of deactivated forms reached about 210° C. Finally, distillation was terminated when the pressure inside the vessel reached about 0.01 kPa. The distillate and residue inside the flask were subjected to $^1$H- and $^{119}$Sn-NMR measurements. The distillate was tri-n-octyl(3-methylbutyloxy) tin. The residue inside the flask contained 77.2 wt % of 1,1,3,3-tetra-n-octyl-1,3-bis(3-methylbutyloxy) distannoxane, and according to $^{119}$Sn-NMR, was found to be a mixture of organic tin compounds containing tin atoms demonstrating a plurality of chemical shifts at from −240 to −605 ppm. There were 28.9 g of the resulting distillate and 100.1 g of residue inside the flask.

Step (11-2): Substituent Exchange Reaction of Deactivated Forms of Dialkyl Tin Catalyst 27.4 g of the tri-n-octyl(3-methylbutyloxy) tin obtained in step (11-1) were placed in a 300 mL pear-shaped flask followed by the addition of 27.2 g of acetic anhydride and stirring for 1 hour at 25° C. A fractionation head equipped with a reflux condenser connected to a distillate collector and a thermometer were attached to the flask, and after replacing the inside of the flask with nitrogen in a vacuum, the flask was immersed in an oil bath heated to 50° C. The pressure inside the vessel was gradually reduced, and the excess acetic anhydride and so forth were distilled off to obtain 25.9 g of a residue inside the flask. When the residue was subjected to $^1$H- and $^{119}$Sn-NMR measurements, the residue was determined to be tri-n-octylacetoxy tin.

On the other hand, 99.4 g of the residue containing 77.2 wt % of 1,1,3,3-tetra-n-octyl-1,3-bis(3-methylbutyloxy) distannoxane obtained in step (11-1) were placed in a 500 mL metal pressure vessel followed by adding 121.6 g of acetic anhydride and stirring. The metal pressure vessel was then immersed in an oil bath heated to 200° C. and heated for 3 hours. After allowing the metal pressure vessel to cool to the vicinity of room temperature (about 25° C.), the contents were transferred to a 500 mL pear-shaped flask. A fractionation head equipped with a reflux condenser connected to a distillate collector and a thermometer were attached to the flask and the inside of the flask was replaced with nitrogen in a vacuum followed by immersing the flask in an oil bath heated to 50° C. The pressure inside the vessel was gradually reduced and the isoamyl acetate and excess acetic anhydride were distilled off to obtain 107.2 g of residue in the flask. When the residue was subjected to $^1$H- and $^{119}$Sn-NMR measurements, the residue was determined to be a mixture containing di-n-octyl diacetoxy tin and n-octyl triacetoxy tin, and the content of di-n-octyl diacetoxy tin in the residue was 77.8 wt % while the content of n-octyl triacetoxy tin was 22.1 wt %. This mixture was mixed with the previously obtained tri-n-octyl acetoxy tin and used as the raw material of the subsequent step (11-3).

Step (11-3): Alkyl Group Redistribution Reaction 131.0 g of a reaction liquid were recovered by carrying out the same method as step (1-5) of Example 1 in a nitrogen atmosphere with the exception of using 132.1 g of the mixture obtained in step (11-2) instead of the mixture obtained in step (1-4). When $^1$H- and $^{119}$Sn-NMR measurement were carried out on this reaction liquid, the reaction liquid was found to be a mixture of di-n-octyl diacetoxy tin and n-octyl triacetoxy tin, and the content of di-n-octyl diacetoxy tin in the mixture was 95.1 wt %.

Step (11-4): Alkoxylation of Dialkyl Tin Compounds 120.0 g of a solution containing 94.4 wt % of 1,1,3,3-tetra-n-butyl-1,3-bis(3-methylbutyloxy) distannoxane were obtained by carrying out the same method as step (1-6) of Example 1 with the exception of using 130.1 g of the reaction liquid obtained in step (11-3) instead of the reaction liquid obtained in step (1-5) of Example 1, and using 312 mL of 0.1 mol/L aqueous potassium hydroxide solution and 194.3 g of 3-methyl-1-butanol.

Example 12

Step (12-1): Separation of Tri-n-octyl (3-Methylbutyloxy) Tin 33.2 g of a distillate and 109.0 g of a residue in the flask were obtained by carrying out the same method as Step (11-1) of Example 11 with the exception of using 143 g of a composition of deactivated forms obtained using the same method as step (7-2) of Example 7. When $^1$H- and $^{119}$Sn-NMR measurement were carried out, the distillate was found to be tri-n-octyl (3-methylbutyloxy) tin, and the residue in the flask was found to be a mixture containing 78.1 wt % of 1,1,3,3-tetra-n-butyl-1,3-bis(3-methylbutyloxy) distannoxane and, according to $^{119}$Sn-NMR, organic tin compounds containing tin atoms demonstrating a plurality of chemical shifts at from −240 to −605 ppm.

Step (12-2): Substituent Exchange Reaction of Dialkyl Tin Catalyst 32.1 g of the tri-n-octyl (3-methylbutyloxy) tin obtained in step (12-1) were placed in a 300 mL pear-shaped flask followed by the addition of 23.2 g of acetic anhydride and 17.7 g of acetic acid and stirring for 1 hour at 25° C. When the solution was sampled and analyzed by gas chromatography, isoamyl acetate was confirmed to have been formed. A fractionation head equipped with a reflux condenser connected to a distillate collector and a thermometer were attached to the flask and the inside of the vessel was replaced with nitrogen in a vacuum followed by immersing the flask in an oil bath heated to 50° C. The pressure inside the vessel was gradually reduced and the isoamyl acetate and excess acetic anhydride were distilled off to obtain 30.5 g of residue in the flask. When the residue was subjected to $^1$H- and $^{119}$Sn-NMR measurement, the residue was found to be tri-n-octyl acetoxy tin.

On the other hand, 108.8 g of the residue containing 78.1 wt % of the 1,1,3,3-tetra-n-octyl-1,3-bis(3-methylbutyloxy) distannoxane obtained in step (12-1) were placed in a 500 mL metal pressure vessel followed by adding 121.6 g of acetic anhydride and 78.5 g of acetic acid and stirring. The metal pressure vessel was then immersed in an oil bath heated to 200° C. and heated for 3 hours. After allowing the metal pressure vessel to cool to the vicinity of room temperature (about 25° C.), the contents were transferred to a 500 mL pear-shaped flask. A fractionation head equipped with a reflux condenser connected to a distillate collector and a thermometer were attached to the flask and the inside of the flask was replaced with nitrogen in a vacuum followed by immersing the flask in an oil bath heated to 50° C. The pressure inside the vessel was gradually reduced and the isoamyl acetate and excess acetic anhydride were distilled off to obtain 117.2 g of residue in the flask. When the residue was subjected to $^1$H- and $^{119}$Sn-NMR measurements, the residue was determined to be a mixture containing di-n-octyl diacetoxy tin and n-octyl triacetoxy tin, and the content of di-n-octyl diacetoxy tin in the residue was 77.6 wt % while the content of n-octyl triacetoxy tin was 22.3 wt %. This mixture was mixed with the previously obtained tri-n-octyl acetoxy tin and used as the raw material of the subsequent step (12-3).

Step (12-3): Alkyl Group Redistribution Reaction 145.3 g of a reaction liquid were recovered by carrying out the same method as step (1-5) of Example 1 under a nitrogen atmosphere with the exception of using 146.5 g of the mixture obtained in step (12-2) instead of the mixture obtained in step (1-4) of Example 1. When $^1$H- and $^{119}$Sn-NMR measurements were carried out on this reaction liquid, the reaction liquid was found to be a mixture of di-n-octyl diacetoxy tin and n-octyl triacetoxy tin, and the content of di-n-octyl diacetoxy tin in the mixture was 95.5 wt %.

Step (12-4): Regeneration of Dialkyl Tin Catalyst from Dialkyl Tin Compounds 129.1 g of a solution containing 94.7 wt % of 1,1,3,3-tetra-n-butyl-1,3-bis(methylbutyloxy) distannoxane were obtained by carrying out the same method as step (1-6) of Example 1 with the exception of using 144.3 g of the reaction liquid obtained in step (12-3) instead of the reaction liquid obtained in step (1-5) of Example 1, and using 322 mL of 0.1 mol/L aqueous potassium hydroxide solution and 212.8 g of 3-methyl-1-butanol.

Example 13

Step (13-1): Substituent Exchange Reaction of Deactivated Forms of Dialkyl Tin Catalyst 227.2 g of a mixture of tri-n-octyl propionyloxy tin, di-n-octyl dipropionyloxy tin and, according to $^{119}$Sn-NMR, organic tin compounds containing tin atoms demonstrating a plurality of chemical shifts at from −240 to −605 ppm were obtained by carrying out the same method as step (2-1) of Example 2 with the exception of using 215 g of a composition of deactivated form obtained using the same method as step (7-2) of Example 7 instead of the composition of deactivated forms obtained in step (1-2) of Example 1, and using 317.9 g of propionic anhydride instead of acetic anhydride. The content of tri-n-octyl propionyloxy tin in the mixture was 22.8 wt % while the content of di-n-octyl dipropionyloxy tin was 63.4 wt %.

Step (13-2): Alkyl Group Redistribution Reaction 222.5 g of a reaction liquid were recovered by carrying out the same method as step (2-1) of Example 2 with the exception of using 223.2 g of the mixture obtained in step (13-1) instead of the mixture obtained in step (2-1). When $^1$H- and $^{119}$Sn-NMR measurements were carried out on this reaction liquid, the reaction liquid was found to be a mixture containing di-n-octyl dipropionyloxy tin, tri-n-octyl propionyloxy tin and 1,1,3,3-tetra-n-octyl-1,3-dipropionyloxy distannoxane, and the content of di-n-octyl dipropionyloxy tin was 63.0 wt %, the content of tri-n-octyl propionyloxy tin was about 5 wt %, and the content of 1,1,3,3-tetra-n-octyl-1,3-dipropionyloxy distannoxane was 30.0 wt %.

Step (13-3): Alkoxylation of Dialkyl Tin Compounds 192.3 g of a solution containing 92.8 wt % of 1,1,3,3-tetra-n-octyl-1,3-bis(3-methylbutyloxy) distannoxane were obtained by carrying out the same method as step (1-6) of Example 1 with the exception of using 221.8 g of the mixture obtained in step (13-2) instead of the mixture obtained in step (1-6) of Example 1, and using 322 mL of 0.1 mol/L aqueous potassium hydroxide solution and 298.8 g of 3-methyl-1-butanol.

Example 14

Step (14-1): Dealkylation Reaction 238.7 g of a mixture containing 86.0 wt % of di-n-octyl dipropionyloxy tin were obtained by carrying out the same method as step (6-1) of Example 6 with the exception of using 230 g of a composition of deactivated forms obtained using the same method as step (7-2) of Example 7 instead of the composition of deactivated forms obtained in step (1-2) of Example 1, and using 195.2 g of propionic acid instead of acetic acid and using 340.2 g of propionic anhydride instead of acetic anhydride.

Step (14-2): Separation of Dialkyl Forms 191.9 g of a distillate were obtained by carrying out the same method as step (6-2) of Example 6 with the exception of using 237.1 g of the mixture containing 86.0 wt % of di-n-octyl dipropionyloxy tin obtained in step (14-1) and making the temperature 200° C. When $^1$H- and $^{119}$Sn-NMR measurements were carried out on the distillate, the distillate was found to be di-n-octyl diacetoxy tin.

Step (14-3): Alkoxylation of Dialkyl Tin Compounds 211.3 g of a mixture containing 84.5 wt % of 1,1,3,3-tetra-n-octyl-1,3-bis(3-methylbutyloxy) distannoxane were obtained by carrying out the same method as step (1-6) of Example 1 with the exception of using 237.1 g of the mixture containing 86.0 wt % of the di-n-octyl dipropionyloxy tin obtained in step (14-1) instead of the reaction liquid obtained in step (1-5) of Example 1, and using 396 mL of 0.1 mol/L aqueous potassium hydroxide solution and 354.5 g of 3-methyl-1-butanol.

Example 15

Step (15-1): Separation of Tri-n-octyl (3-Methylbutyloxy) Tin 43.1 g of a distillate and 146.1 g of a residue in a flask were obtained by carrying out the same method as step (11-1) of Example 11 with the exception of using 190 g of a composition of deactivated forms obtained using the same method as step (7-2) of Example 7. $^1$H- and $^{119}$Sn-NMR measurements were carried out on the distillate and the residue in the flask. The distillate was found to be tri-n-octyl (3-methylbutyloxy) tin. The residue in the flask was found to be a mixture containing 77.6 wt % of 1,1,3,3-tetra-n-octyl-1,3-bis(3-methylbutyloxy) distannoxane and, according to $^{119}$Sn-NMR, organic tin compounds containing tin atoms demonstrating a plurality of chemical shifts at from −240 to −605 ppm.

Step (15-2): Substituent Exchange Reaction of Deactivated Forms of Dialkyl Tin Catalyst 42.2 g of the tri-n-octyl(3-methylbutyloxy) tin obtained in step (15-1) were placed in a 300 mL pear-shaped flask followed by the addition of 28.7 g of propionic acid and 51.5 g of propionic anhydride and stirring for 1 hour at 25° C. When the solution was sampled and analyzed by gas chromatography, isoamyl propionate was confirmed to have been formed. A fractionation head equipped with a reflux condenser connected to a distillate collector and a thermometer were attached to the flask, and after replacing the inside of the flask with nitrogen in a vacuum, the flask was immersed in an oil bath heated to 80° C. The pressure inside the vessel was gradually reduced, and the isoamyl propionate and excess propionic acid and propionic anhydride were distilled off to obtain 41.1 g of a residue inside the flask. When the residue was subjected to $^1$H- and $^{119}$Sn-NMR measurements, the residue was determined to be tri-n-octyl propionyloxy tin.

On the other hand, 145.1 g of the residue containing 77.6 wt % of the 1,1,3,3-tetra-n-octyl-1,3-bis(3-methylbutyloxy) distannoxane obtained in step (15-1) were placed in a 500 mL metal pressure vessel followed by adding 128.9 g of propionic acid and 226.7 g of propionic anhydride and stirring. The metal pressure vessel was then immersed in an oil bath heated to 200° C. and heated for 4 hours. After allowing the metal pressure vessel to cool to the vicinity of room temperature (about 25° C.), the contents were transferred to a 500 mL pear-shaped flask. A fractionation head equipped with a reflux condenser connected to a distillate collector and a thermometer were attached to the flask and the inside of the flask was replaced with nitrogen in a vacuum followed by immersing the flask in an oil bath heated to 80° C. The pressure inside the vessel was gradually reduced and the excess propionic acid and propionic anhydride were distilled off to obtain 167.7 g of residue in the flask. When the residue was subjected to $^1$H- and $^{119}$Sn-NMR measurement, the residue was determined to be a mixture containing di-n-octyl dipropionyloxy tin and n-octyl tripropionyloxy tin, and the content of di-n-octyl dipropionyloxy tin in the residue was 77.0 wt % while the content of n-octyl tripropionyloxy tin was 22.4 wt %. This mixture was mixed with the previously obtained tri-n-octyl propionyloxy tin and used as the raw material of the subsequent step (15-3).

Step (15-3): Alkyl Group Redistribution Reaction 205.9 g of a reaction liquid were recovered by carrying out the same method as step (1-5) of Example 1 under a nitrogen atmosphere with the exception of using 207.2 g of the mixture obtained in step (15-2) instead of the mixture obtained in step (1-4) of Example 1. When $^1$H- and $^{119}$Sn-NMR measurements were carried out on this reaction liquid, the reaction liquid was found to be a mixture of di-n-octyl dipropionyloxy tin and n-octyl tripropionyloxy tin, and the content of di-n-octyl dipropionyloxy tin in the mixture was 91.0 wt %.

Step (15-4): Alkoxylation of Dialkyl Tin Compounds 171.5 g of a solution containing 90.8 wt % of 1,1,3,3-tetra-n-butyl-1,3-bis(3-methylbutyloxy) distannoxane were obtained by carrying out the same method as step (1-6) of Example 1 with the exception of using 204.6 g of the reaction liquid obtained in step (15-3) instead of the reaction liquid obtained in step (1-5) of Example 1, and using 332 mL of 0.1 mol/L aqueous potassium hydroxide solution and 284.1 g of 3-methyl-1-butanol.

Example 16

Step (16-1): Production of Dialkyl Tin Catalyst 893 g (2.48 mol) of di-n-octyl tin oxide (Sankyo Organic Chemicals Co., Ltd., Japan) and 2403 g (23.6 mol) of 2-ethyl-1-butanol were placed in a 5000 mL volumetric pear-shaped flask. The flask was connected to an evaporator to which was connected an oil bath equipped with a temperature controller, a vacuum pump and a vacuum controller. The purge valve outlet of this evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to about 165° C., the flask was immersed in the oil bath and rotation of the evaporator was started. After heating for about 40 minutes in the presence of atmospheric pressure nitrogen with the purge valve of the evaporator left open, distillation of 2-ethyl-1-butanol containing water began. After maintaining in this state for 7 hours, the purge valve was closed, pressure inside the system was gradually reduced, and excess 2-ethyl-1-butanol was distilled with the pressure inside the system at from 74 to 25 kPa. After the fraction no longer appeared, the flask was taken out of the oil bath. After allowing the flask to cool to the vicinity of room temperature (25° C.), the purge valve was opened gradually and the pressure inside the system was returned to atmospheric pressure. 1114 g of reaction liquid were obtained in the flask. Based on the results of $^{119}$Sn-, $^{1}$H- and $^{13}$C-NMR analyses, 1,1,3,3-tetra-n-octyl-1,3-bis(2-ethylbutyloxy) distannoxane was confirmed to have been obtained at a yield of 99% based on di-n-octyl tin oxide. The same procedure was then repeated 12 times to obtain a total of 13380 g of 1,1,3,3-tetra-n-octyl-1,3-bis(2-ethylbutyloxy) distannoxane.

Step (16-2): Production of Carbonic Acid Ester and Recovery of Composition of Deactivated Forms of Dialkyl Tin Catalyst Carbonic acid ester was produced in a continuous production apparatus like that shown in FIG. 2. 1,1,3,3-tetra-n-octyl-1,3-bis(2-ethylbutyloxy) distannoxane produced in the manner described above was supplied at the rate of 6074 g/hr from transfer line 4 into column-type reaction vessel 102 packed with Metal Gauze CY Packing and having an inner diameter of 151 mm and effective length of 5040 mm, and 2-ethyl-1-butanol purified with distillation column 101 was supplied at the rate of 12260 g/hr from transfer line 2. The liquid temperature inside reaction vessel 102 was controlled to 160° C. by a heater and reboiler 112, and the pressure was adjusted to about 120 kPa-G with a pressure control valve. The residence time in the reaction vessel was about 17 minutes. 2-ethyl-1-butanol containing water at the rate of 12344 g/hr from the top of the reaction vessel via transfer line 6, and 2-ethyl-1-butanol at the rate of 958 g/hr via feed line 1, were pumped to distillation column 101 packed with Metal Gauze CY Packing and provided with reboiler 111 and condenser 121 to carry out distillative purification. In the top of distillation column 101, a fraction containing a high concentration of water was condensed by condenser 121 and recovered from recovery line 3. Purified 2-ethyl-1-butanol was pumped to column-type reaction vessel 102 via transfer line 2 located in the bottom of distillation column 101. An alkyl tin alkoxide catalyst composition containing di-n-octyl-bis(2-ethylbutyloxy) tin and 1,1,3,3-tetra-n-octyl-1,3-bis(2-ethylbutyloxy) distannoxane was obtained from the bottom of column-type reaction vessel 102, and supplied to thin film evaporator 103 via transfer line 5. The 2-ethyl-1-butanol was distilled off in thin film evaporator 103 and returned to column-type reaction vessel 102 via condenser 123, transfer line 8 and transfer line 4. The alkyl tin alkoxide catalyst composition was pumped from the bottom of thin film evaporator 103 via transfer line 7 and supplied to autoclave 104 while adjusting the flow rate of di-n-octyl-bis (2-ethylbutyloxy) tin and 1,1,3,3-tetra-n-octyl-1,3-bis(2-ethylbutyloxy) distannoxane to about 6945 g/hr. Carbon dioxide was supplied to the autoclave by transfer line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the alkyl tin alkoxide catalyst composition was carried out to obtain a reaction liquid containing bis(2-ethylbutyl) carbonate. This reaction liquid was transferred to decarbonization tank 105 via transfer line 10 and a control valve to remove residual carbon dioxide, and the carbon dioxide was recovered from transfer line 11. Subsequently, the reaction liquid was transferred to thin film evaporator 106 set to about 142° C. and about 0.5 kPa via a transfer line 12 and supplied while adjusting the flow rate of 1,1,3,3-tetra-n-octyl-1,3-bis(2-ethylbutyloxy) distannoxane to about 6074 g/hr to obtain a fraction containing bis(2-ethylbutyl) carbonate. On the other hand, the evaporation residue was circulated to column-type reaction vessel 102 via transfer line 13 and transfer line 14 while adjusting the flow rate of 1,1,3,3-tetra-n-octyl-1,3-bis (2-ethylbutyloxy) distannoxane to about 6074 g/hr. The fraction containing bis(2-ethylbutyl) carbonate was supplied to distillation column 107 packed with Metal Gauze CY packing and equipped with reboiler 117 and condenser 127 via condenser 126 and transfer line 14 at the rate of 959 g/hr followed by distillative purification to obtain 99 wt % bis(2-ethylbutyl) carbonate from recovery line 16 at the rate of 1075 g/hr. When the alkyl tin alkoxide catalyst composition of transfer line 13 was analyzed by $^{119}$Sn-, $^{1}$H- and $^{13}$C-NMR analysis, it was found to contain 1,1,3,3-tetra-n-octyl-1,3-bis (2-ethylbutyloxy) distannoxane but not contain di-n-octyl-bis (2-ethylbutyloxy) tin. After carrying out the above-mentioned continuous operation for about 220 hours, alkyl tin alkoxide catalyst composition was extracted from extraction line 16 at the rate of 18 g/hr, 1,1,3,3-tetra-n-octyl-1,3-bis(2-ethylbutyloxy) distannoxane produced according to the above process was supplied from feed line 17 at the rate of 18 g/hr, and 180 g of a catalyst composition of 1,1,3,3-tetra-n-octyl-1,3-bis(2-ethylbutyloxy) distannoxane was extracted from extraction line 16. As a result of analysis by $^{119}$Sn-NMR, in addition to containing about 55 wt % of 1,1,3,3-tetra-n-octyl-1,3-bis(2-ethylbutyloxy) distannoxane, tri-n-octyl(2-ethylbutyloxy) tin and a plurality of NMR shifts of deactivated components of 1,1,3,3-tetra-n-octyl-1,3-bis(2-ethylbutyloxy) distannoxane were observed at from −240 to −605 ppm. This catalyst composition was used as a composition of deactivated forms.

Step (16-3): Substituent Exchange Reaction of Deactivated Forms of Dialkyl Tin Catalyst 174.5 g of a mixture of tri-n-octyl acetoxy tin, di-n-octyl diacetoxy tin and, according to $^{119}$Sn-NMR, organic tin compounds containing tin atoms demonstrating a plurality of chemical shifts at from −240 to −605 ppm were obtained by carrying out the same method as step (2-1) of Example 2 with the exception of using 180 g of the composition of deactivated forms obtained in step (16-2) instead of the composition of deactivated forms obtained in step (1-2) of Example 1 and using 202.1 g of acetic anhydride. The content of tri-n-octyl acetoxy tin in the mixture was 26.4 wt % and the content of di-n-octyl diacetoxy tin was 57.9 wt %.

Step (16-4): Alkyl Group Redistribution Reaction 172.0 g of a reaction liquid were recovered by carrying out the same method as step (2-1) of Example 2 with the exception of using 173.1 g of the mixture obtained in step (16-3) instead of the mixture obtained in step (2-1) of Example 2. When $^1$H- and $^{119}$Sn-NMR measurements were carried out on the reaction liquid, the reaction liquid was determined to be a mixture containing di-n-octyl diacetoxy tin, tri-n-octyl acetoxy tin and 1,1,3,3-tetra-n-octyl-1,3-diacetoxy distannoxane, and the content of di-n-octyl diacetoxy tin was 57.8 wt %, the content of tri-n-octyl acetoxy tin was about 3 wt %, and the content of 1,1,3,3-tetra-n-octyl-1,3-diacetoxy distannoxane was 37.8 wt %.

Step (16-5): Alkoxylation of Dialkyl Tin Compounds 165.2 g of a solution containing 95.6 wt % of 1,1,3,3-tetra-n-octyl-1,3-bis(2-ethylbutyloxy) distannoxane were obtained by carrying out the same method as step (1-6) of Example 1 with the exception of using 171.1 g of the mixture obtained in step (16-4) instead of the reaction liquid obtained in step (1-5) of Example 1, and using 255 mL of 0.1 mol/L aqueous potassium hydroxide solution and 303.7 g of 2-ethyl-1-butanol.

Example 17

Step (17-1): Dealkylation Reaction 202.6 g of a mixture containing 83.8 wt % of di-n-octyl diacetoxy tin were obtained by carrying out the same method as step (6-1) of Example 6 with the exception of using 215 g of a composition of deactivated forms obtained using the same method as step (16-2) of Example 16 instead of the composition of deactivated forms obtained in step (I-2) of Example 1, and using 141.9 g of acetic acid and 241.2 g of acetic anhydride.

Step (17-2): Separation of Dialkyl Forms 195.1 g of a distillate were obtained by carrying out the same method as step (6-2) of Example 6 with the exception of using 200.5 g of the mixture containing 83.8 wt % of di-n-octyl diacetoxy tin obtained in step (17-1) at a temperature of 200° C. When $^1$H- and $^{119}$Sn-NMR measurements were carried out on the distillate, the distillate was found to be di-n-octyl diacetoxy tin.

Step (17-3): Alkoxylation of Dialkyl Tin Compounds 181.0 g of 1,1,3,3-tetra-n-octyl-1,3-bis(2-ethylbutyloxy) distannoxane were obtained by carrying out the same method as step (1-6) of Example 1 with the exception of using 193.6 g of the di-n-octyl diacetoxy tin obtained in step (17-2) instead of the reaction liquid obtained in step (1-5) of Example 1, and using 311 mL of 0.1 mol/L aqueous potassium hydroxide solution and 365.9 g of 2-ethyl-1-butanol.

Example 18

Step (18-1): Separation of Tri-n-octyl (2-Ethylbutyloxy) Tin 36.2 g of distillate and 110.6 g of residue in a flask were obtained by carrying out the same method as step (11-1) of Example 11 with the exception of using 148 g of a composition of deactivated forms obtained using the same method as step (16-2) of Example 16 and setting the oil bath temperature to 250° C. The distillate was found to be tri-n-octyl (2-ethylbutyloxy) tin, and the residue inside the flask was found to be a mixture containing 72.8 wt % of 1,1,3,3-tetra-n-octyl-1,3-bis(2-ethylbutyloxy) distannoxane and, according to $^{119}$Sn-NMR, organic tin compounds containing tin atoms demonstrating a plurality of chemical shifts at from −240 to −605 ppm.

Step (18-2): Substituent Exchange Reaction of Deactivated Forms of Dialkyl Tin Catalyst 35.1 g of the tri-n-octyl(2-ethylbutyloxy) tin obtained in step (18-1) were placed in a 300 mL pear-shaped flask followed by the addition of 23.3 g of propionic acid and 40.9 g of propionic anhydride and stirring for 1 hour at 25° C. When the solution was sampled and analyzed by gas chromatography, isoamyl propionate was confirmed to have been formed. A fractionation head equipped with a reflux condenser connected to a distillate collector and a thermometer were attached to the flask, and after replacing the inside of the flask with nitrogen in a vacuum, the flask was immersed in an oil bath heated to 80° C. The pressure inside the vessel was gradually reduced, and the isoamyl propionate and excess propionic acid and propionic anhydride were distilled off to obtain 33.3 g of a residue inside the flask. When the residue was subjected to $^1$H- and $^{119}$Sn-NMR measurements, the residue was determined to be tri-n-octyl propionyloxy tin.

On the other hand, 110.1 g of the residue containing 72.8 wt % of 1,1,3,3-tetra-n-octyl-1,3-bis(2-ethylbutyloxy) distannoxane obtained in step (18-1) were placed in a 500 mL metal pressure vessel followed by adding 95.2 g of propionic acid and 167.2 g of propionic anhydride and stirring. The metal pressure vessel was then immersed in an oil bath heated to 200° C. and heated for 3.5 hours. After allowing the metal pressure vessel to cool to the vicinity of room temperature (about 25° C.), the contents were transferred to a 500 mL pear-shaped flask. A fractionation head equipped with a reflux condenser connected to a distillate collector and a thermometer were attached to the flask and the inside of the flask was replaced with nitrogen in a vacuum followed by immersing the flask in an oil bath heated to 80° C. The pressure inside the vessel was gradually reduced and the excess propionic anhydride and propionic acid and so forth were distilled off to obtain 123.4 g of residue in the flask. When the residue was subjected to $^1$H- and $^{119}$Sn-NMR measurements, the residue was determined to be a mixture containing di-n-octyl dipropionyloxy tin and n-octyl tripropionyloxy tin, and the content of di-n-octyl dipropionyloxy tin in the residue was 73.6 wt % while the content of n-octyl tripropionyloxy tin was 26.1 wt %. This mixture was mixed with the previously obtained tri-n-octyl propionyloxy tin and used as the raw material of the subsequent step (18-3).

Step (18-3): Alkyl Group Redistribution Reaction 153.8 g of a reaction liquid were recovered by carrying out the same method as step (1-5) of Example 1 in a nitrogen atmosphere with the exception of using 154.5 g of the mixture obtained in step (18-2) instead of the mixture obtained in step (1-4) of Example 1. When $^1$H- and $^{119}$Sn-NMR measurements were carried out on this reaction liquid, the reaction liquid was found to be a mixture of di-n-octyl dipropionyloxy tin and n-octyl tripropionyloxy tin, and the content of di-n-octyl dipropionyloxy tin in the mixture was 90.5 wt %.

Step (18-4): Alkoxylation of Dialkyl Tin Compounds 131.5 g of a solution containing 90.5 wt % of 1,1,3,3-tetra-n-butyl-1,3-bis(2-ethylbutyloxy) distannoxane were obtained by carrying out the same method as step (1-6) of Example 1 with the exception of using 152.2 g of the reaction liquid obtained in step (18-3) instead of the reaction liquid obtained in step (1-5) of Example 1, and using 286 mL of 0.1 mol/L aqueous potassium hydroxide solution and 244.9 g of 2-ethyl-1-butanol.

Example 19

Step (19-1): Dealkylation Reaction 219.4 g of a mixture containing 84.0 wt % of di-n-octyl dipropionyloxy tin were obtained by carrying out the same method as step (6-1) of Example 6 with the exception of using 220 g of a composition of deactivated forms obtained using the same method as step (16-2) of Example 16 instead of the composition of deactivated forms obtained in step (I-2) of Example 1, and using 179.3 g of propionic acid instead of acetic acid and using 315.0 g of propionic anhydride instead of acetic anhydride.

Step (19-2): Separation of Dialkyl Forms 212.4 g of a distillate were obtained by carrying out the same method as step (6-2) of Example 6 with the exception of using 217.4 g of the mixture containing 84.0 wt % of di-n-octyl dipropionyloxy tin obtained in step (19-1) at a temperature of 220° C. When $^1$H- and $^{119}$Sn-NMR measurements were carried out on the distillate, the distillate was found to be di-n-octyl dipropionyloxy tin.

Step (19-3): Alkoxylation of Dialkyl Tin Compounds 194.4 g of a mixture containing 81.7 wt % of 1,1,3,3-tetra-n-octyl-1,3-bis(2-ethylbutyloxy) distannoxane were obtained by carrying out the same method as step (1-6) of Example 1 with the exception of using 211.3 g of the mixture containing 86.0 wt % of di-n-octyl dipropionyloxy tin obtained in step (19-1) instead of the reaction liquid obtained in step (1-5) of Example 1, and using 411 mL of 0.1 mol/L aqueous potassium hydroxide solution and 318.0 g of 2-ethyl-1-butanol.

Example 20

Step (20-1): Separation of Tri-n-octyl (2-Ethylbutyloxy) Tin 48.3 g of distillate and 138.8 g of residue in a flask were obtained by carrying out the same method as step (11-1) of Example 11 with the exception of using 188 g of a composition of deactivated forms obtained using the same method as step (16-2) of Example 16 and setting the oil bath temperature to 250° C. The distillate was found to be tri-n-octyl (2-ethylbutyloxy) tin, and the residue inside the flask was found to be a mixture containing 74.0 wt % of 1,1,3,3-tetra-n-octyl-1,3-bis(2-ethylbutyloxy) distannoxane and, according to $^{119}$Sn-NMR, organic tin compounds containing tin atoms demonstrating a plurality of chemical shifts at from −240 to −605 ppm.

Step (20-2): Substituent Exchange Reaction of Deactivated Forms of Dialkyl Tin Catalyst 47.2 g of the tri-n-octyl(2-ethylbutyloxy) tin obtained in step (20-1) were placed in a 300 mL pear-shaped flask followed by the addition of 80.3 g of hexanoic acid and 92.6 g of hexanoic anhydride and stirring for 1 hour at 25° C. When the solution was sampled and analyzed by gas chromatography, isoamyl propionate was confirmed to have been formed. A fractionation head equipped with a reflux condenser connected to a distillate collector and a thermometer were attached to the flask, and after replacing the inside of the flask with nitrogen in a vacuum, the flask was immersed in an oil bath heated to 80° C. The pressure inside the vessel was gradually reduced, and the (2-ethylbutyloxy) hexanoate and excess hexanoic acid and hexanoic anhydride and the like were distilled off to obtain 48.3 g of a residue inside the flask. When the residue was subjected to $^1$H- and $^{119}$Sn-NMR measurements, the residue was determined to be tri-n-octyl hexanonyloxy tin.

On the other hand, 137.2 g of the residue containing 74.0 wt % of the 1,1,3,3-tetra-n-octyl-1,3-bis(2-ethylbutyloxy) distannoxane obtained in step (20-1) were placed in a 500 mL metal pressure vessel followed by adding 130.8 g of hexanoic acid and 331.0 g of propionic anhydride and stirring. The metal pressure vessel was then immersed in an oil bath heated to 200° C. and heated for 6.2 hours. After allowing the metal pressure vessel to cool to the vicinity of room temperature (about 25° C.), the contents were transferred to a 500 mL pear-shaped flask. A fractionation head equipped with a reflux condenser connected to a distillate collector and a thermometer were attached to the flask and the inside of the flask was replaced with nitrogen in a vacuum followed by immersing the flask in an oil bath heated to 80° C. The pressure inside the vessel was gradually reduced and the excess hexanoic anhydride and hexanoic acid and so forth were distilled off to obtain 185.3 g of residue in the flask. When the residue was subjected to $^1$H- and $^{119}$Sn-NMR measurements, the residue was determined to be a mixture containing di-n-octyl dihexanonyloxy tin and n-octyl trihexanonyloxy tin, and the content of di-n-octyl dihexanonyloxy tin in the residue was 71.5 wt % while the content of n-octyl trihexanonyloxy tin was 28.5 wt %. This mixture was mixed with the previously obtained tri-n-octyl hexanonyloxy tin and used as the raw material of the subsequent step (20-3).

Step (20-3): Alkyl Group Redistribution Reaction 229.6 g of a reaction liquid were recovered by carrying out the same method as step (1-5) of Example 1 in a nitrogen atmosphere with the exception of using 230.5 g of the mixture obtained in step (20-2) instead of the mixture obtained in step (1-4) of Example 1. When $^1$H- and $^{119}$Sn-NMR measurement were carried out on this reaction liquid, the reaction liquid was found to be a mixture containing di-n-octyl dihexanonyloxy tin and n-octyl trihexanonyloxy tin, and the content of di-n-octyl dihexanonyloxy tin in the mixture was 88.3 wt %.

Step (20-4): Alkoxylation of Dialkyl Tin Compounds 193.4 g of a solution containing 88.1 wt % of 1,1,3,3-tetra-n-butyl-1,3-bis(2-ethylbutyloxy) distannoxane were obtained by carrying out the same method as step (1-6) of Example 1 with the exception of using 225.1 g of the reaction liquid obtained in step (20-3) instead of the reaction liquid obtained in step (1-5) of Example 1, and using 280 mL of 0.1 mol/L aqueous potassium hydroxide solution and 327.7 g of 2-ethyl-1-butanol.

Example 21

Step (21-1): Dealkylation Reaction 274.7 g of a mixture containing 77.4 wt % of di-n-octyl dihexanonyloxy tin were obtained by carrying out the same method as step (6-1) of Example 6 with the exception of using 217 g of a composition of deactivated forms obtained using the same method as step (16-2) of Example 16 instead of the composition of deactivated forms obtained in step (1-2) of Example 1, and using 266.2 g of hexanoic acid instead of acetic acid and using 204.6 g of hexanoic anhydride instead of acetic anhydride.

Step (21-2): Separation of Dialkyl Forms 202.1 g of a distillate were obtained by carrying out the same method as step (6-2) of Example 6 with the exception of using 273.9 g of the mixture containing 77.4 wt % of di-n-octyl dihexanonyloxy tin obtained in step (21-1) at a temperature of 220° C. When $^1$H- and $^{119}$Sn-NMR measurements were carried out on the distillate, the distillate was found to be di-n-octyl dihexanonyloxy tin.

Step (21-3): Alkoxylation of Dialkyl Tin Compounds 194.4 g of a mixture containing 81.7 wt % of 1,1,3,3-tetra-n-octyl-1,3-bis(2-ethylbutyloxy) distannoxane were obtained by carrying out the same method as step (1-6) of Example 1 with the exception of using 211.3 g of the mixture of di-n-octyl dihexanonyloxy tin obtained in step (21-2) instead of the reaction liquid obtained in step (1-5) of Example 1, and using 411 mL of 0.1 mol/L aqueous potassium hydroxide solution and 318.0 g of 2-ethyl-1-butanol.

Example 22

Step (22-1): Substituent Exchange Reaction of Deactivated Forms of Dialkyl Tin Catalyst Excess maleic anhydride was distilled off to obtain 232.1 g of a mixture of organic tin compounds containing tin atoms demonstrating a plurality of chemical shifts at from −240 to −605 ppm, the vicinity of −150 ppm and the vicinity of 100 ppm as determined by $^{119}$Sn-NMR by carrying out the same method as step (2-1) of Example 2 with the exception of using 210 g of a composition of deactivated forms obtained using the same method as step (16-2) of Example 16 instead of the composition of deactivated forms obtained in step (1-2) of Example 1, and using 362.2 g of maleic anhydride instead of acetic anhydride.

Step (22-2): Alkyl Group Redistribution Reaction 228.3 g of a reaction liquid were recovered by carrying out the same method as step (2-1) of Example 2 with the exception of using 230.8 g of the mixture obtained in step (22-1) instead of the mixture obtained in step (2-1) of Example 2. When $^1$H- and $^{119}$Sn-NMR measurements were carried out on this reaction liquid, the reaction liquid was found to be a mixture of organic tin compounds containing tin atoms demonstrating a plurality of chemical shifts at from −240 to −605 ppm, the vicinity of from −140 to −200 ppm, and the vicinity of 100 ppm as determined by $^{119}$Sn-NMR. In particular, the ratio of the integral value of the plurality of peaks in the vicinity of 100 ppm and the ratio of the integral value of the peaks at from −240 to −605 ppm to the integral value of all peaks were considerably lower than the ratio of the integral value in the composition obtained in step (22-1).

Step (22-3): Alkoxylation of Dialkyl Tin Compounds 168.1 g of a solution containing 87.4 wt % of 1,1,3,3-tetra-n-octyl-1,3-bis(2-ethylbutyloxy) distannoxane were obtained by carrying out the same method as step (1-6) of Example 1 with the exception of using 220.1 g of the mixture obtained in step (22-2) instead of the reaction liquid obtained in step (1-5) of Example 1, and using 255 mL of 0.1 mol/L aqueous potassium hydroxide solution and 303.6 g of 2-ethyl-1-butanol.

Example 23

Step (23-1): Dealkylation Reaction

The same method as step (6-1) of Example 6 was carried out with the exception of using 197 g of a composition of deactivated forms obtained using the same method as Step (16-2) of Example 16 instead of the composition of deactivated forms obtained in step (1-2) of Example 1, and using 152.7 g of maleic acid and 129.5 g of maleic anhydride instead of acetic acid and acetic anhydride. The excess maleic acid and maleic anhydride and the like were distilled off to obtain 214.8 g of the resulting mixture. This mixture was determined by $^{119}$Sn-NMR to be a mixture of organic tin compounds containing tin atoms demonstrating a plurality of chemical shifts at from −240 to −605 ppm and in the vicinity of from −140 to −200 ppm.

Step (23-2): Alkoxylation of Dialkyl Tin Compounds 164.3 g of a solution containing 81.2 wt % of 1,1,3,3-tetra-n-octyl-1,3-bis(2-ethylbutyloxy) distannoxane were obtained by carrying out the same method as step (1-6) of Example 1 with the exception of using 213.1 g of the di-n-octyl diacetoxy tin obtained in step (23-1) instead of the reaction liquid obtained in step (1-5) of Example 1, and using 443 mL of 0.1 mol/L aqueous potassium hydroxide solution and 296.8 g of 2-ethyl-1-butanol.

Example 24

Step (24-1): Production of Tetraalkyl Dialkoxy Distannoxane 692 g (2.78 mol) of di-n-butyl tin oxide and 2000 g (27 mol) of 1-butanol (Wako Pure Chemical Industries, Ltd., Japan) were placed in a 3000 mL pear-shaped flask. The flask containing the white, slurry-like mixture was connected to an evaporator to which was connected an oil bath equipped with a temperature controller, a vacuum pump and a vacuum controller. The purge valve outlet of this evaporator was connected to a line containing nitrogen gas flowing at normal pressure. After closing the purge valve of the evaporator to reduce pressure inside the system, the purge valve was opened gradually to allow nitrogen to flow into the system and return to normal pressure. The oil bath temperature was set to about 126° C., the flask was immersed in the oil bath and rotation of the evaporator was started. After rotating and heating for about 30 minutes at normal pressure with the purge valve of the evaporator left open, the mixture boiled and distillation of the low boiling point component began. After maintaining in this state for 8 hours, the purge valve was closed, pressure inside the system was gradually reduced, and residual low boiling point component was distilled off with the pressure inside the system at from 76 to 54 kPa. After the low boiling point component no longer appeared, the flask was taken out of the oil bath. The reaction liquid was in the form of a clear liquid. The flask was subsequently taken out of the oil bath, the purge valve was opened gradually and the pressure inside the system was returned to normal pressure. 952 g of reaction liquid were obtained in the flask. Based on the results of $^{119}$Sn-, $^1$H- and $^{13}$C-NMR analyses, the reaction liquid was determined to be 1,1,3,3-tetra-n-butyl-1,3-di(butyloxy) distannoxane, and the yield based on di-n-butyl tin oxide was 99%. The same procedure was then repeated 12 times to obtain a total of 11488 g of 1,1,3,3-tetra-n-butyl-1,3-di(butyloxy) distannoxane.

Step (24-2): Production of Carbonic Acid Ester and Acquisition of Composition of Deactivated Forms of Alkyl Tin Alkoxide Catalyst Containing Deactivated Forms Carbonic acid ester was produced in a continuous production apparatus like that shown in FIG. 2. 1,1,3,3-Tetrabutyl-1,3-bi(butyloxy) distannoxane produced in step 1 was supplied at the rate of 4201 g/hr from transfer line 4 into a column-type reaction vessel packed with Mellapak 750Y packing and having an inner diameter of 151 mm and effective length of 5040 mm, and 1-butanol purified with distillation column 101 was supplied to column-type reaction vessel 102 at the rate of 24717 g/hr from feed line 2. The liquid temperature inside the reaction vessel was controlled to 160° C. by a heater and reboiler 112, and the pressure was adjusted to about 250 kPa-G with a pressure control valve. The residence time in the reaction vessel was about 10 minutes. 1-Butanol containing water at the rate of 24715 g/hr from the top of the reaction vessel via transfer line 6, and 1-butanol at the rate of 824 g/hr via feed line 1, were pumped to distillation column 101 packed with Metal Gauze CY packing and provided with reboiler 111 and condenser 121 to carry out distillative purification. In the top of distillation column 101, a fraction containing a high concentration of water was condensed by condenser 121 and recovered from transfer line 3. Purified 1-butanol was pumped via transfer line 2 located in the bottom of distillation column 101. An alkyl tin alkoxide catalyst composition containing dibutyl tin dibutoxide and 1,1,3,3-tetra-n-butyl-1,3-di(butyloxy) distannoxane was obtained from the bottom of column-type reaction vessel 102, and supplied to thin film evaporator 103 via a transfer line 5. The 1-butanol was distilled off in thin film evaporator 103 and returned to column-type reaction vessel 102 via condenser 123, transfer line 8 and transfer line 4. The alkyl tin alkoxide catalyst composition was pumped from the bottom of thin film evaporator 103 via transfer line 7 and supplied to autoclave 104 while adjusting the flow rate of the active components in the form of dibutyl tin dibutoxide and 1,1,3,3-tetra-n-butyl-1,3-di(butyloxy) distannoxane to about 4812 g/hr. Carbon dioxide was supplied to the autoclave by feed line 9 at the rate of 973 g/hr, and the pressure inside the autoclave was maintained at 4 MPa-G. The temperature inside the autoclave was set to 120° C., the residence time was adjusted to about 4 hours, and a reaction between the carbon dioxide and the alkyl tin alkoxide catalyst composition was carried out to obtain a reaction liquid containing dibutyl carbonate. This reaction liquid was transferred to decarbonization tank 105 via transfer line 10 and a control valve to remove residual carbon dioxide, and the carbon dioxide was recovered from transfer line 11. Subsequently, the reaction liquid was transferred to thin film evaporator 106 set to about 140° C. and about 1.4 kPa via transfer line 12 and supplied while adjusting the flow rate of the 1,1,3,3-tetra-n-butyl-1,3-di(butyloxy) distannoxane to about 4201 g/hr to obtain a fraction containing dibutyl carbonate. On the other hand, the evaporation residue was circulated to column-type reaction vessel 102 via transfer line 13 and transfer line 4 while adjusting the flow rate of 1,1,3,3-tetra-n-butyl-1,3-di(butyloxy) distannoxane to about 4201 g/hr. The fraction containing dibutyl carbonate was supplied to distillation column 107 packed with Metal Gauze CY packing and equipped with reboiler 117 and condenser 127 via condenser 126 and a transfer line 14 at the rate of 830 g/hr followed by distillative purification to obtain 99 wt % bis(3-methylbutyl) carbonate from recovery line 16 at the rate of 814 g/hr. When the alkyl tin alkoxide catalyst composition of transfer line 13 was analyzed by $^{119}$Sn-, $^{1}$H- and $^{13}$C-NMR analysis, it was found to contain 1,1,3,3-tetra-n-butyl-1,3-di(butyloxy) distannoxane but not contain dibutyl tin dibutoxide. After carrying out the above-mentioned continuous operation for about 600 hours, alkyl tin alkoxide catalyst composition was extracted from extraction line 16 at the rate of 16 g/hr, while 1,1,3,3-tetra-n-butyl-1,3-di(butyloxy) distannoxane produced in step 1 was supplied from feed line 17 at the rate of 16 g/hr. About 120 g of liquid were sampled from extraction line 16, and when analyzed by $^{119}$Sn-NMR, was determined to contain about 60 wt % of 1,1,3,3-tetra-n-butyl-1,3-di(butyloxy) distannoxane, and demonstrate a plurality of NMR shifts originating from tributyl tin butoxide and a high boiling point component at from −240 to −605 ppm.

Step (24-3): Acquisition of Dialkyl Tin Dialkoxide from Composition of Deactivated Forms of Alkyl Tin Alkoxide Catalyst Containing Deactivated Forms Starting substances in the form of 120 g of the alkyl tin alkoxide catalyst composition containing heat-denatured forms obtained in step 2 and 332.5 g (1.91 mol) of dibutyl carbonate produced in step 2 were mixed in a 500 mL volumetric pear-shaped flask in a glove box replaced with nitrogen and then stopped. The flask containing the mixture was attached to an evaporator to which was connected an oil bath equipped with a temperature controller, a vacuum pump and a vacuum controller. The purge valve outlet of this evaporator was connected to a line containing nitrogen gas flowing at normal pressure. After closing the purge valve of the evaporator to reduce pressure inside the system, the purge valve was opened gradually to allow nitrogen to flow into the system and return to normal pressure to replace the inside of the reaction apparatus with nitrogen. The oil bath temperature was set to about 150° C., the flask was immersed in the oil bath and rotation of the evaporator was started. After rotating and heating for about 3 hours at normal pressure with the purge valve of the evaporator left open, the purge valve was closed, pressure inside the system was gradually reduced, and residual reactants were distilled with the pressure inside the system at from 20 to 3 kPa. After the distillate no longer appeared, the flask was taken out of the oil bath to obtain 140.5 g of a reaction liquid.

(Distillation Separation of Reaction Liquid)

Next, 135.3 g of the reaction liquid were placed in a volumetric 200 mL three-mouth flask equipped with a three-way valve, a distillation column packed with Helipack No. 3 and measuring 45 cm in length, a fractionation head equipped with a reflux condenser connected to a distillate collector and a thermometer through the three-way valve using a gas-tight syringe (Hamilton Inc.) while allowing nitrogen gas to flow in at the rate of 0.3 L/min. The flask was immersed in an oil bath heated to about 175° C. After carrying out stirring and heating for about 20 minutes, the temperature of the reaction liquid was about 167° C. The pressure inside the apparatus was gradually decreased and distillation was carried out at about 0.2 kPa. Distillate 1 was recovered at the rate of about 0.5 mL/min. After distillate 1 no longer appeared, the pressure inside the apparatus was further reduced to about 0.03 kPa and distillation was continued to recover distillate 2 at the rate of about 0.5 mL/min. The distillate no longer appeared after about 2 hours, the decompression in the apparatus was released and heating was discontinued to terminate distillation. The amounts of the resulting distillate 1, distillate 2 and residue in the flask were 31.8 g, 72.9 g and 30.6 g, respectively. NMR analysis was carried out on distillate 1, distillate 2 and the residue in the flask. 81.2 wt % of Tri-n-butyl butoxy tin and 18.2 wt % of dibutyl carbonate were obtained in distillate 1, while 99.0 wt % of di-n-butyl dibutoxy tin was obtained in distillate 2. The residue in the flask contained about 1 wt % of 1,1,3,3-tetra-n-butyl-1,3-di(butyloxy) distannoxane, and a plurality of NMR shifts originating from a high boiling point component were observed at from −240 to −605 ppm.

Step (24-4): Substituent Exchange Reaction of Deactivated Forms of Dialkyl Tin Catalyst 30.2 g of distillate 1 obtained in step (24-3) were placed in a 300 mL pear-shaped flask followed by the addition of 34.7 g of acetic anhydride and stirring for 1 hour at 25° C. When the solution was sampled and subjected to analysis by gas chromatography, butyl acetate was confirmed to have been formed. A fractionation head equipped with a reflux condenser connected to a distillate collector and a thermometer were attached to the flask, and after replacing the inside of the flask with nitrogen in a vacuum, the flask was immersed in an oil bath heated to 80° C. The pressure inside the vessel was gradually reduced, and the excess acetic anhydride and so forth were distilled off to obtain 29.2 g of a residue inside the flask. When the residue was subjected to $^{1}$H- and $^{119}$Sn-NMR measurements, the residue was determined to be a mixture of tri-n-butyl(butyloxy) tin and dibutyl carbonate.

On the other hand, 29.5 g of the residue inside the flask obtained in step (24-3) were placed in a 500 mL metal pressure vessel followed by adding 57.3 g of acetic anhydride and stirring. The metal pressure vessel was then immersed in an oil bath heated to 200° C. and heated for 5.3 hours. After allowing the metal pressure vessel to cool to the vicinity of room temperature (about 25° C.), the contents were transferred to a 500 mL pear-shaped flask. A fractionation head equipped with a reflux condenser connected to a distillate collector and a thermometer were attached to the flask and the inside of the flask was replaced with nitrogen in a vacuum followed by immersing the flask in an oil bath heated to 80° C. The pressure inside the vessel was gradually reduced and the excess acetic anhydride and the like were distilled off to obtain 39.0 g of residue in the flask. When the residue was subjected to $^1$H- and $^{119}$Sn-NMR measurements, the residue was determined to be a mixture containing di-n-butyl diacetoxy tin and n-butyl triacetoxy tin, and the content of di-n-butyl diacetoxy tin in the mixture was 28.0 wt % while the content of n-butyl triacetoxy tin was 72.0 wt %. This mixture was mixed with the previously obtained tri-n-butyl acetoxy tin and used as the raw material of the subsequent step (24-5).

Step (24-5): Alkyl Group Redistribution Reaction 65.5 g of a reaction liquid were recovered by carrying out the same method as step (1-5) of Example 1 under a nitrogen atmosphere with the exception of using 66.5 g of the mixture obtained in step (24-4) instead of the mixture obtained in step (1-4) of Example 1. When $^1$H- and $^{119}$Sn-NMR measurements were carried out on this reaction liquid, the reaction liquid was found to be a mixture containing di-n-butyl diacetoxy tin and n-butyl triacetoxy tin, and the content of di-n-butyl diacetoxy tin in the mixture was 87.2 wt %.

Step (24-6): Alkoxylation of Dialkyl Tin Compounds 46.7 g of a solution containing 95.1 wt % of 1,1,3,3-tetra-n-butyl-1,3-di(butyloxy) distannoxane were obtained by carrying out the same method as step (1-6) of Example 1 with the exception of using 65.1 g of the reaction liquid obtained in step (24-5) instead of the reaction liquid obtained in step (1-5) of Example 1, and using 72 mL of 0.1 mol/L aqueous potassium hydroxide solution and 107.1 g of 1-butanol.

Example 25

Figure 3:
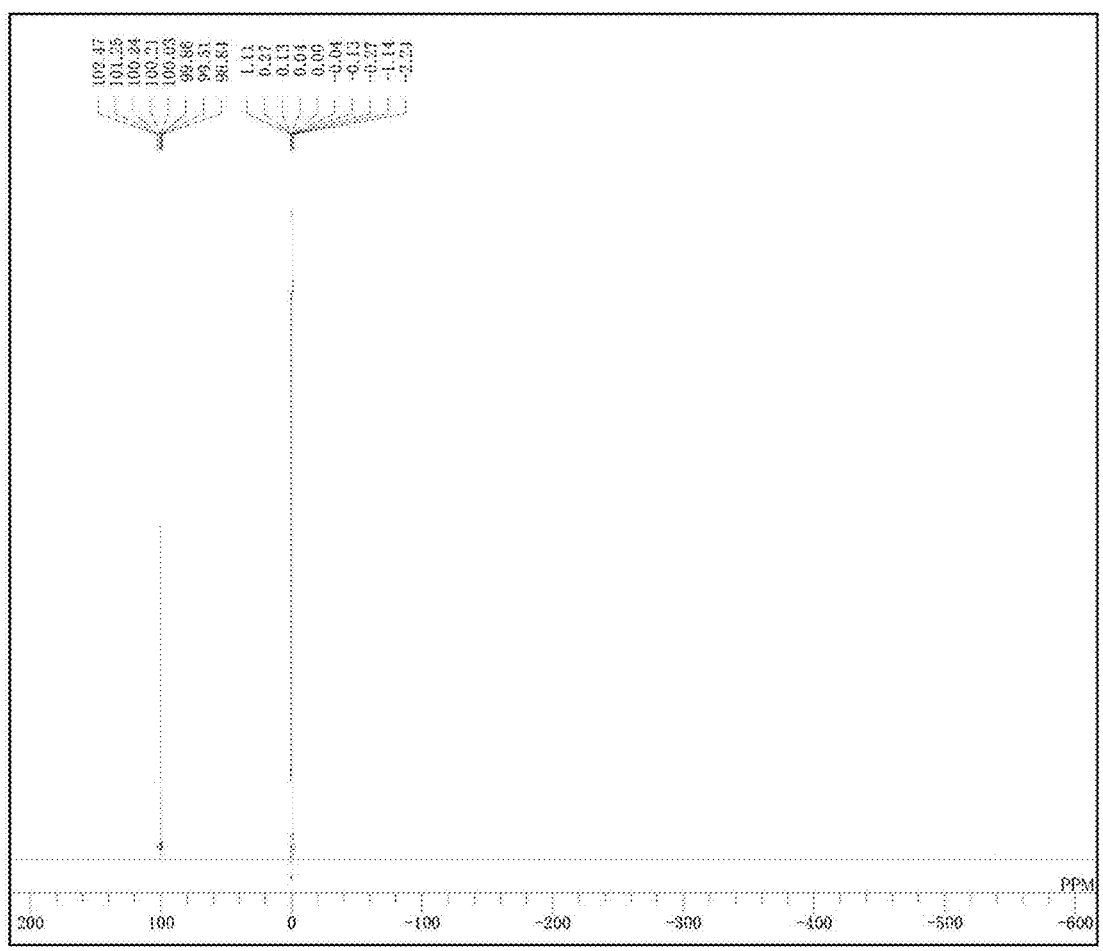
FIG. 3 shows the $^{119}$Sn-NMR spectrum of tri-n-octyl(3-methylbutyloxy)tin separated from step (23-1) of Example 23 in the present invention.
Figure 4:
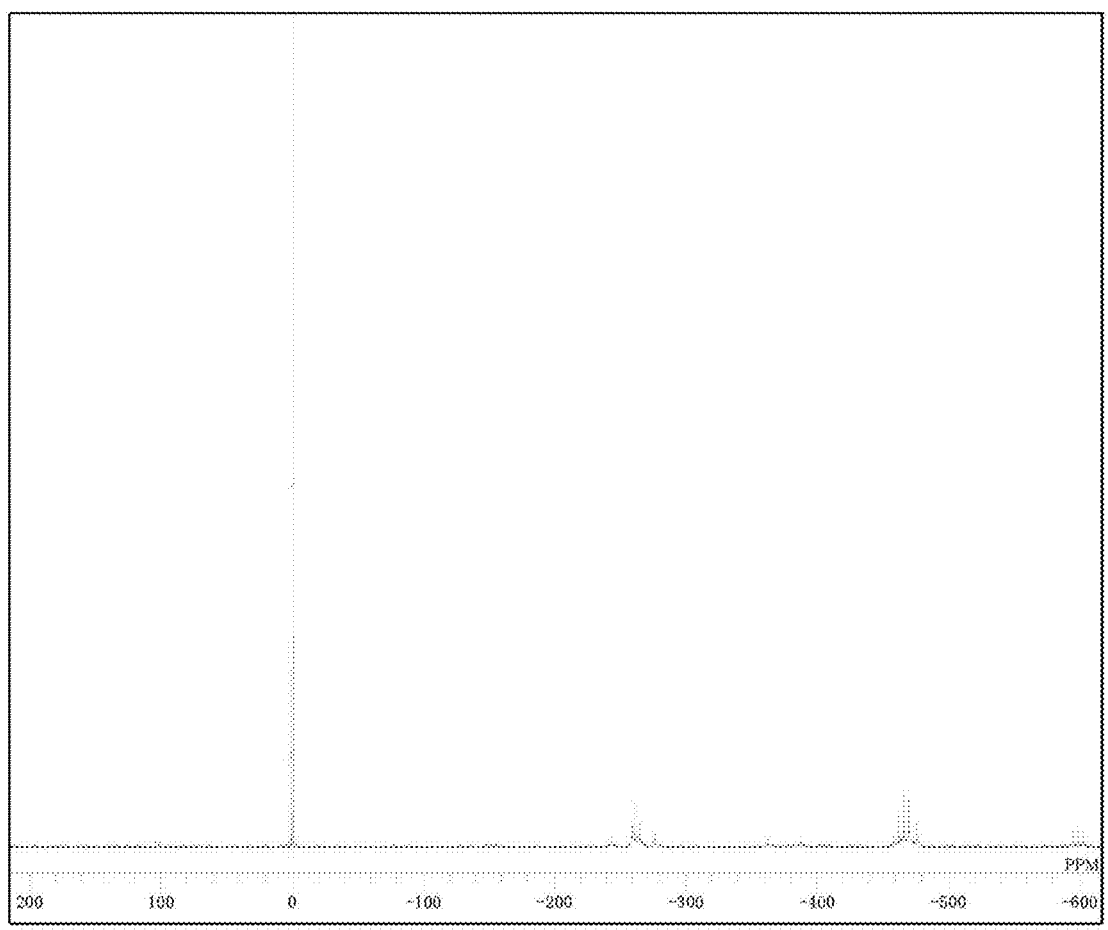
FIG. 4 shows the $^{119}$Sn-NMR spectrum of a high boiling point component at from −240 to −605 ppm separated in step (23-1) of Example 23 in the present invention.

Step (25-1): Acquisition of Dialkyl Tin Dialkoxide from Dialkyl Tin Compound Containing Deactivated Forms 380 g of a composition of deactivated forms obtained by carrying out the same method as step (7-1) of Example 7 were supplied to a molecular distillation apparatus (Model MS-300, Sibata Scientific Technology Ltd., Japan) at the rate of 300 g/hr, and volatile components were distilled off at a temperature of about 230° C. and pressure of about 0.02 kPa. 83.5 g of low boiling point component were recovered. When $^1$H- and $^{119}$Sn-NMR measurements were carried out on the low boiling point component, tri-n-octyl (3-methylbutyloxy) tin was found to be contained at 99 wt % (see FIG. 3). 295.5 g of a high boiling point component were obtained, and when analyzed by $^1$H- and $^{119}$Sn-NMR measurement, in addition to 1,1,3,3-tetra-n-octyl-1,3-bis(3-methylbutyloxy) distannoxane, a plurality of NMR shifts originating from heat-denatured forms were observed at from −240 to −605 ppm. The content of 1,1,3,3-tetra-n-octyl-1,3-bis(3-methylbutyloxy) distannoxane contained in the high boiling point component was 76.9 wt %. 264.3 g of the high boiling point component and 717.5 g (3.55 mol) of bis(3-methylbutyl) carbonate produced in step (7-2) of Example 7 were mixed in a flask under a nitrogen atmosphere, and allowed to react for 2 hours at 140° C. in the presence of nitrogen at atmospheric pressure. Subsequently, the reaction liquid was supplied to a molecular distillation apparatus at the rate of 300 g/hr and the residual carbonic acid ester was separated at a temperature of about 150° C. and pressure of about 0.5 kPa to obtain a high boiling point component in the form of about 656 g of liquid. The high boiling point component was supplied to a molecular distillation apparatus at the rate of 300 g/hr followed by distillative separation at a temperature of about 240° C. and pressure of about 0.02 kPa to obtain 251.5 g of a low boiling point component. The low boiling point component contained di-n-octyl-bis(3-methylbutyloxy) tin at 99.3 wt %. On the other hand, a plurality of NMR shifts were observed in the high boiling point component originating from a high boiling point component at from −240 to −605 ppm (see FIG. 4).

Figure 5:
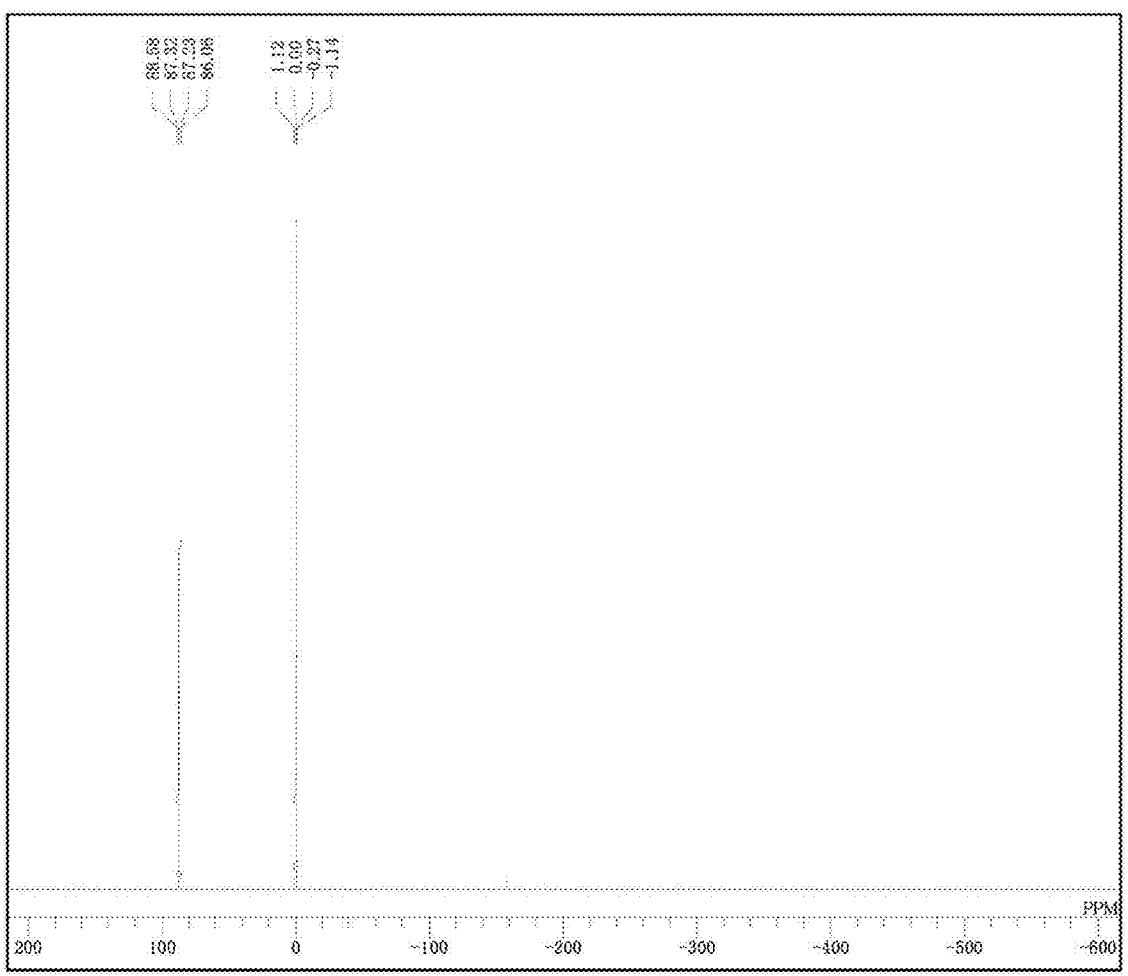
FIG. 5 shows the $^{119}$Sn-NMR spectrum of tri-n-octyl acetoxy tin produced in step (23-2) of Example 23 in the present invention.

Step (25-2): Substituent Exchange Reaction of Deactivated Forms of Dialkyl Tin Catalyst 82.2 g of distillate 1 containing 99 wt % of tri-n-octyl(3-methylbutyloxy) tin obtained in step (25-1) were placed in a 300 mL pear-shaped flask followed by the addition of 92.3 g of acetic anhydride and stirring for 1 hour at 25° C. When the solution was sampled and subjected to analysis by gas chromatography, isoamyl acetate was confirmed to have been formed. A fractionation head equipped with a reflux condenser connected to a distillate collector and a thermometer were attached to the flask, and after replacing the inside of the flask with nitrogen in a vacuum, the flask was immersed in an oil bath heated to 80° C. The pressure inside the vessel was gradually reduced, and the excess acetic anhydride and so forth were distilled off to obtain 78.0 g of a residue inside the flask. When the residue was subjected to $^1$H- and $^{119}$Sn-NMR measurements, the residue was determined to be tri-n-octyl acetoxy tin (see FIG. 5).

Figure 6:
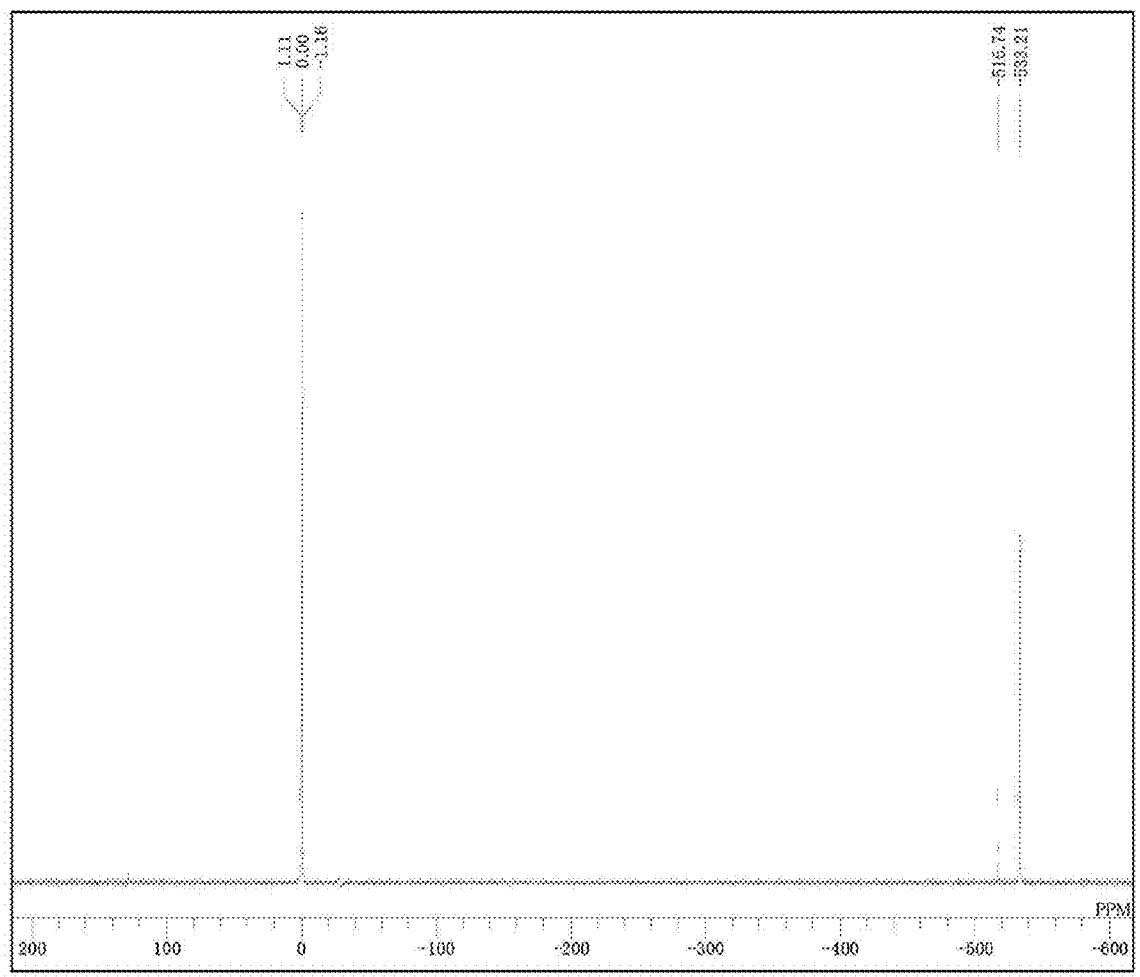
FIG. 6 shows the $^{119}$Sn-NMR spectrum of a mixture containing n-octyl triacetoxy tin produced in step (23-2) of Example 23 in the present invention.

On the other hand, 97.4 g of the high boiling point component obtained in step (25-1) were placed in a 500 mL metal pressure vessel followed by adding 30.1 g of acetic acid and 163.7 g of acetic anhydride and stirring. The metal pressure vessel was then immersed in an oil bath heated to 200° C. and heated for 4 hours. After allowing the metal pressure vessel to cool to the vicinity of room temperature (about 25° C.), the contents were transferred to a 500 mL pear-shaped flask. A fractionation head equipped with a reflux condenser connected to a distillate collector and a thermometer were attached to the flask and the inside of the flask was replaced with nitrogen in a vacuum followed by immersing the flask in an oil bath heated to 80° C. The pressure inside the vessel was gradually reduced and the excess acetic anhydride and the like were distilled off to obtain 90.1 g of residue in the flask. When the residue was subjected to $^1$H- and $^{119}$Sn-NMR measurement, the residue was determined to be a mixture mainly containing n-octyl triacetoxy tin, and the content of n-octyl triacetoxy tin in the mixture was 87.1 wt % (see FIG. 6). This mixture was mixed with the previously obtained tri-n-octyl acetoxy tin and used as the raw material of the subsequent step (25-3).

Step (25-3): Alkyl Group Redistribution Reaction 165.8 g of a reaction liquid were recovered by carrying out the same method as step (1-5) of Example 1 in a nitrogen atmosphere with the exception of using 167.2 g of the mixture obtained in step (25-2) instead of the mixture obtained in step (1-4) of Example 1. When $^1$H- and $^{119}$Sn-NMR measurements were carried out on this reaction liquid, the reaction liquid was found to be a mixture containing di-n-octyl diacetoxy tin and n-octyl triacetoxy tin, and the content of di-n-octyl diacetoxy tin in the mixture was 91.2 wt %.

Figure 7:
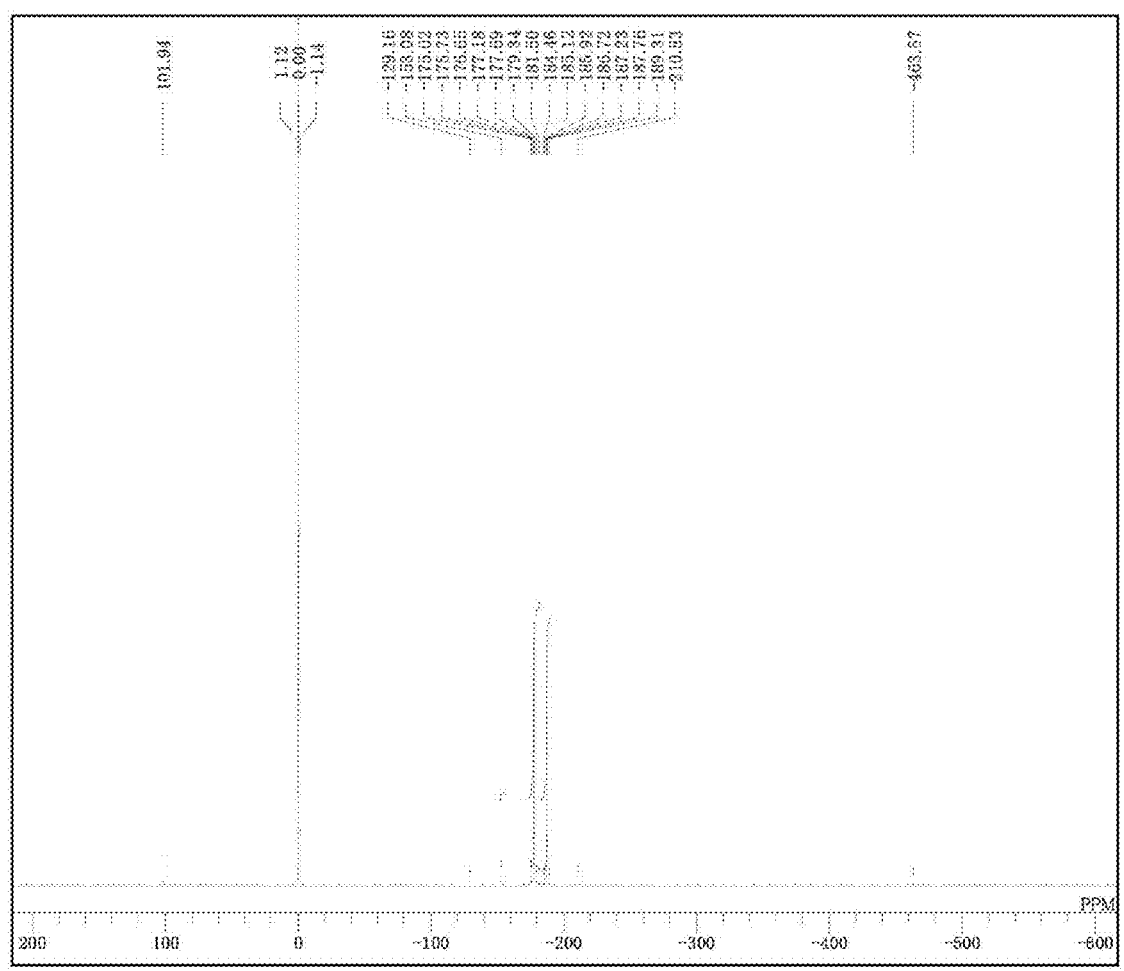
FIG. 7 shows the $^{119}$Sn-NMR spectrum of a solution containing 1,1,3,3-tetra-n-octyl-1,3-bis(3-methylbutyloxy) distannoxane produced in step (23-4) of Example 23 in the present invention.

Step (25-4): Alkoxylation of Dialkyl Tin Compounds 120.2 g of a solution containing 89.9 wt % of 1,1,3,3-tetra-n-octyl-1,3-bis(3-methylbutyloxy) distannoxane were obtained by carrying out the same method as step (1-6) of Example 1 with the exception of using 166.4 g of the reaction liquid obtained in step (25-3) instead of the reaction liquid obtained in step (1-5) of Example 1, and using 430 mL of 0.1 mol/L aqueous potassium hydroxide solution and 215.5 g of 3-methyl-1-butanol (see FIG. 7).

Example 26

Step (26-1): Recovery of Composition of Deactivated Forms Formed Accompanying Production of Dialkyl Tin Catalyst 520 g (2.1 mol) of dibutyl tin oxide, 3213 g (31.5 mol) of 2-ethyl butanol and a stirrer for stirring were placed in a 5 L volumetric four-mouth flask equipped with a vacuum controller, a condenser connected to vacuum pump and a Dean-Stark tube. After replacing the inside of the system with nitrogen, the flask was immersed in an oil bath heated to 146° C. and stirring was started. After continuing to heat for about 20 minutes while removing the distillate, the pressure was gradually reduced, after which a low boiling point component was further distilled off for about 20 minutes with the pressure inside the system at from 76 to 30 kPa. The flask was cooled after new distillate was no longer observed. 722.1 g of a reaction liquid were obtained in the flask and as a result of analyzing by $^1$H- and $^{119}$Sn-NMR, the reaction liquid was found to contain 76.1 wt % of 1,1,3,3-di-n-butyl-tetra(2-ethylbutyloxy) tin and 13.3 wt % of tri-n-butyl(2-ethylbutoxy) tin.

Step (26-2): Separation of Tri-n-butyl (2-Ethylbutyloxy) Tin

A three-way valve, a distillation column packed with Helipack No. 3, a fractionation head equipped with a reflux condenser connected to a distillate collector and a thermometer were attached to the flask containing the reaction liquid, and the inside of the system was replaced with nitrogen. The flask was immersed in an oil bath heated to about 190° C., and distillation was carried out while gradually reducing pressure in the system to 1.3 kPa with a vacuum pump to obtain a distillate 1. Heating was discontinued and distillation was terminated when liquid distillate was no longer observed. 93.1 g of distillate 1 were recovered and as a result of analyzing by $^1$H-, $^{13}$C- and $^{119}$Sn-NMR, the distillate was determined to contain 98 wt % of tri-n-butyl(2-ethylbutyloxy) tin. In addition, 624.7 g of residue were obtained inside the flask, and as a result of analyzing the residue by $^1$H-, $^{13}$C- and $^{119}$Sn-NMR, the residue was found to contain 87.3 wt % of 1,1,3,3-di-n-butyl-tetra(2-ethylbutyloxy) tin.

Step (26-3): Substituent Exchange Reaction of Deactivated Forms of Dialkyl Tin Catalyst 92.0 g of the distillate obtained in step (26-2), 71.4 g of acetic acid and 145.7 g of acetic anhydride were placed in a 500 mL pear-shaped flask, and the flask was placed in a water bath controlled to 30° C. followed by stirring for 2 hours. The flask was attached to a rotary evaporator to which was connected an oil bath equipped with a temperature controller, a vacuum pump and a vacuum controller. The purge valve outlet of this evaporator was connected to a line containing nitrogen gas flowing at normal pressure. After replacing the inside of the system with nitrogen, the temperature of the oil bath was set to 40° C., the flask was immersed in the oil bath and rotation of the rotary evaporator was started. After distilling off the excess acetic acid and acetic anhydride under reduced pressure at 0.1 kPa, 82.3 g of a residue was obtained in the flask. Based on the results of $^1$H-, $^{13}$C- and $^{119}$Sn-NMR analyses, the residue was found to contain 99 wt % of tri-n-butyl acetoxy tin.

On the other hand, 153.2 g in the flask obtained in step (26-2) were placed in a 500 mL metal pressure vessel followed by the addition of 82.1 g of acetic acid and 232.7 g of acetic anhydride. The metal pressure vessel was then immersed in an oil bath heated to 250° C. and heated for 5 hours. After allowing the metal pressure vessel to cool, the contents were transferred to a 500 mL pear-shaped flask. A fractionation head equipped with a reflux condenser connected to a distillate collector and a thermometer were attached to the flask and the inside of the flask was replaced with nitrogen in a vacuum followed by immersing the flask in an oil bath heated to 50° C. The pressure inside the vessel was gradually reduced and the excess acetic anhydride and the like were distilled off to obtain 159.9 g of residue in the flask. The same procedure was carried out on the remaining 470.3 g of residue in the flask to obtain a total of 650.8 g of residue. When the residue was subjected to $^1$H- and $^{119}$Sn-NMR measurements, the residue was determined to be a mixture containing n-butyl triacetoxy tin and di-n-butyl-bis(2-ethylbutyloxy) tin, and the content of n-butyl triacetoxy tin in the mixture was 13.6 wt %, while the content of di-n-butyl-bis(2-ethylbutyloxy) tin was 86.2 wt %.

This mixture was mixed with the previously obtained tri-n-butyl acetoxy tin and used as the raw material of the subsequent step (26-4).

Step (26-4): Alkyl Group Redistribution Reaction 726.5 g of a reaction liquid were recovered by carrying out the same method as step (1-5) of Example 1 under a nitrogen atmosphere with the exception of using 728.2 g of the mixture obtained in step (26-3) instead of the mixture obtained in step (1-4) of Example 1. When the reaction liquid was subjected to $^1$H- and $^{119}$Sn-NMR measurements, the reaction liquid was found to be a mixture containing di-n-butyl diacetoxy tin and n-butyl triacetoxy tin, and the content of di-n-butyl diacetoxy tin in the mixture was 95.2 wt %.

Step (26-5): Alkoxylation of Dialkyl Tin Compounds 742.6 g of a solution containing 97.1 wt % of 1,1,3,3-tetra-n-butyl-1,3-bis(2-ethylbutyloxy) distannoxane were obtained by carrying out the same method as Step (1-6) of Example 1 with the exception of using 724.6 g of the reaction liquid obtained in step (26-4) instead of the reaction liquid obtained in step (1-5) of Example 1, and using 830 mL of 0.1 mol/L aqueous potassium hydroxide solution and 1951 g of 2-ethyl-1-butanol.

Example 27

Step (27-1): Recovery of Composition of Deactivated Forms Formed Accompanying Production of Dialkyl Tin Catalyst 562 g (1.56 mol) of dioctyl tin oxide, 3015 g (23.2 mol) of 2-ethyl-1-hexanol and a stirrer for stirring were placed in a 5 L volumetric four-mouth flask equipped with a vacuum controller, a condenser connected to vacuum pump and a Dean-Stark tube. After replacing the inside of the system with nitrogen, the flask was immersed in an oil bath heated to 180° C. and stirring was started. After continuing to heat for about 5 hours while removing the distillate, the pressure was gradually reduced, after which a low boiling point component was further distilled off for about 5 hours with the pressure inside the system at from 76 to 30 kPa. The flask was cooled after new distillate was no longer observed. 778.3 g of a reaction liquid were obtained in the flask and as a result of analyzing by $^1$H- and $^{119}$Sn-NMR, the reaction liquid was found to contain 40.1 wt % of 1,1,3,3-di-n-octyl-tetra(2-ethylhexyloxy) tin, 16.9 wt % of di-n-octyl-bis(2-ethylhexyloxy) tin and 25.8 wt % of tri-n-octyl(2-ethylhexyloxy) tin.

Step (27-2): Substituent Exchange Reaction of Deactivated Forms of Dialkyl Tin Catalyst 775.8 g of the reaction liquid obtained in step (27-1), 298.1 g of acetic acid and 544.3 g of acetic anhydride were placed in a 2 L pear-shaped flask, and the flask was placed in a water bath controlled to 50° C. followed by stirring for 2 hours. The flask was attached to a rotary evaporator to which was connected an oil bath equipped with a temperature controller, a vacuum pump and a vacuum controller. The purge valve outlet of the rotary evaporator was connected to a line containing nitrogen gas flowing at normal pressure. After replacing the inside of the system with nitrogen, the temperature of the oil bath was set to 50° C., the flask was immersed in the oil bath and rotation of the rotary evaporator was started. After distilling off the excess acetic acid and acetic anhydride under reduced pressure at 0.1 kPa, 685.9 g of a residue was obtained in the flask. Based on the results of $^1$H-, $^{13}$C- and $^{119}$Sn-NMR analyses, the residue was found to be a mixture containing tri-n-octyl acetoxy tin and di-n-octyl diacetoxy tin, and the content of tri-n-octyl acetoxy tin in the mixture was 25.8 wt %, while the content of di-n-octyl diacetoxy tin was 58.9 wt %.

Step (27-3): Alkyl Group Redistribution Reaction 680.8 g of a reaction liquid were recovered by carrying out the same method as step (1-5) of Example 1 in a nitrogen atmosphere with the exception of using 682.2 g of the mixture obtained in step (27-2) instead of the mixture obtained in step (1-4) of Example 1. When the reaction liquid was subjected to $^1$H- and $^{119}$Sn-NMR measurements, the reaction liquid was found to be a mixture containing di-n-octyl diacetoxy tin and tri-n-octyl acetoxy tin, and the content of di-n-octyl diacetoxy tin in the mixture was 58.9 wt %, the content of tri-n-octyl acetoxy tin was 2.1 wt %, and the content of 1,1,3,3-tetra-n-octyl-diacetoxy distannoxane was 37.8 wt %.

Step (27-4): Alkoxylation of Dialkyl Tin Compounds 710.8 g of a solution containing 96.3 wt % of 1,1,3,3-tetra-n-octyl-1,3-bis(2-ethylhexyloxy) distannoxane were obtained by carrying out the same method as Step (1-6) of Example 1 with the exception of using 678.3 g of the reaction liquid obtained in step (27-3) instead of the reaction liquid obtained in step (1-5) of Example 1, and using 833 mL of 0.1 mol/L aqueous potassium hydroxide solution and 1917 g of 2-ethyl-1-hexanol.

Example 28

Step (28-1): Recovery of Composition of Deactivated Forms Formed Accompanying Production of Dialkyl Tin Catalyst 522 g (1.45 mol) of dioctyl tin oxide, 944 g (5.08 mol) of 1-dodecanol and a stirrer for stirring were placed in a 5 L volumetric four-mouth flask equipped with a vacuum controller, a condenser connected to vacuum pump and a Dean-Stark tube. After replacing the inside of the system with nitrogen, the flask was immersed in an oil bath heated to 190° C. and stirring was started. After continuing to heat for about 10 hours while removing the distillate, the pressure was gradually reduced, after which a low boiling point component was further distilled off for about 3 hours with the pressure inside the system at from 76 to 20 kPa. The flask was cooled after new distillate was no longer observed. 823.6 g of a reaction liquid were obtained in the flask and as a result of analyzing by $^1$H- and $^{119}$Sn-NMR, the reaction liquid was found to contain 19.0 wt % of 1,1,3,3-di-n-octyl-tetradodecyl tin, 20.2 wt % of di-n-octyl-didodecyloxy tin and 36.3 wt % of tri-n-octyl-dodecyloxy tin.

Step (28-2): Substituent Exchange Reaction of Deactivated Forms of Dialkyl Tin Catalyst 819.3 g of the reaction liquid obtained in step (28-1) and 887.3 g of acetic anhydride were placed in a 2 L pear-shaped flask, and the flask was placed in a water bath controlled to 50° C. followed by stirring for 2 hours. The flask was attached to a rotary evaporator to which was connected an oil bath equipped with a temperature controller, a vacuum pump and a vacuum controller. The purge valve outlet of the rotary evaporator was connected to a line containing nitrogen gas flowing at normal pressure. After replacing the inside of the system with nitrogen, the temperature of the oil bath was set to 50° C., the flask was immersed in the oil bath and rotation of the rotary evaporator was started. After distilling off the excess acetic anhydride and the like under reduced pressure at 0.1 kPa, 701.2 g of a residue was obtained in the flask. Based on the results of $^1$H-, $^{13}$C- and $^{119}$Sn-NMR analyses, the residue was found to be a mixture containing tri-n-octyl acetoxy tin and di-n-octyl diacetoxy tin, and the content of tri-n-octyl acetoxy tin in the mixture was 37.3 wt %, while the content of di-n-octyl diacetoxy tin was 39.4 wt %.

Step (28-3): Alkyl Group Redistribution Reaction 698.4 g of a reaction liquid were recovered by carrying out the same method as step (1-5) of Example 1 in a nitrogen atmosphere with the exception of using 700.5 g of the mixture obtained in step (28-2) instead of the mixture obtained in step (1-4) of Example 1. When the reaction liquid was subjected to $^1$H- and $^{119}$Sn-NMR measurements, the reaction liquid was found to be a mixture containing di-n-octyl diacetoxy tin and tri-n-octyl acetoxy tin, and the content of di-n-octyl diacetoxy tin in the mixture was 39.4 wt %, the content of tri-n-octyl acetoxy tin was 3.7 wt %, and the content of 1,1,3,3-tetra-n-octyl-diacetoxy distannoxane was 53.6 wt %.

Step (28-4): Alkoxylation of Dialkyl Tin Compounds 711.8 g of a solution containing 92.2 wt % of 1,1,3,3-tetra-n-octyl-1,3-didodecyloxy distannoxane were obtained by carrying out the same method as Step (1-6) of Example 1 with the exception of using 695.9 g of the reaction liquid obtained in step (28-3) instead of the reaction liquid obtained in step (1-5) of Example 1, and using 821 mL of 0.1 mol/L aqueous potassium hydroxide solution and 1925 g of 1-dodecanol.

Example 29

Step (29-1): Recovery of Composition of Deactivated Forms Formed Accompanying Production of Dialkyl Tin Catalyst 662.0 g of a reaction liquid were obtained by carrying out the same method as step (27-1) of Example 27 with the exception of using 479 g (1.33 mol) of dioctyl tin oxide and 2594 g (20.0 mol) of 2-ethyl-1-hexanol. As a result of analyzing by $^1$H- and $^{119}$Sn-NMR, the reaction liquid was found to contain 41.6 wt % of 1,1,3,3-di-n-octyl-tetra(2-ethylhexyloxy) tin, 15.7 wt % of di-n-octyl-bis(2-ethylhexyloxy) tin and 25.9 wt % of tri-n-octyl(2-ethylhexyloxy) tin.

Step (29-2): Dealkylation Reaction 660.1 g of the reaction liquid obtained in step (29-1), 402.0 g of acetic acid and 434.1 g of acetic anhydride were placed in a 2 L pear-shaped flask, and the flask was placed in a water bath controlled to 150° C. followed by heating and stirring for 10 hours. The flask was attached to a rotary evaporator to which was connected an oil bath equipped with a temperature controller, a vacuum pump and a vacuum controller. The purge valve outlet of the rotary evaporator was connected to a line containing nitrogen gas flowing at normal pressure. After replacing the inside of the system with nitrogen, the temperature of the oil bath was set to 50° C., the flask was immersed in the oil bath and rotation of the rotary evaporator was started. After distilling off the excess acetic acid and acetic anhydride under reduced pressure at 0.1 kPa, 568.2 g of a residue were obtained in the flask. Based on the results of $^1$H-, $^{13}$C- and $^{119}$Sn-NMR analyses, the residue was found to be a mixture containing di-n-octyl diacetoxy tin, and the content of di-n-octyl diacetoxy tin in the mixture was 84.2 wt %.

Step (29-3): Alkoxylation of Dialkyl Tin Compounds 577.8 g of a solution containing 81.1 wt % of 1,1,3,3-tetra-n-octyl-1,3-bis(2-ethylhexyloxy) distannoxane were obtained by carrying out the same method as Step (1-6) of Example 1 with the exception of using 565.9 g of the reaction liquid obtained in step (29-2) instead of the reaction liquid obtained in step (1-5) of Example 1, and using 833 mL of 0.1 mol/L aqueous potassium hydroxide solution and 1558 g of 2-ethyl-1-hexanol.

Example 30

Step (30-1): Recovery of Composition of Deactivated Forms Formed Accompanying Production of Dialkyl Tin Catalyst 851.5 g of a reaction liquid were obtained by carrying out the same method as step (28-1) of Example 28 with the exception of using 539 g (1.50 mol) of dioctyl tin oxide and 1670 g (8.98 mol) of 1-dodecanol. The reaction liquid contained 6.6 wt % of 1,1,3,3-di-n-octyl-tetradodecyloxy tin, 21.4 wt % of di-n-octyl-didodecyloxy tin and 43.0 wt % of tri-n-octyldodecyloxy tin.

Step (30-2): Dealkylation Reaction 603.6 g of a residue were obtained in a flask by carrying out the same method as step (29-2) of Example 29 with the exception of using 848.3 g of the reaction liquid obtained in step (30-1), 449.1 g of acetic acid and 488.6 g of acetic anhydride. Based on the results of $^1$H-, $^{13}$C- and $^{119}$Sn-NMR analyses, the residue was found to be a mixture containing di-n-octyl diacetoxy tin, and the content of di-n-octyl diacetoxy tin in the mixture was 71.1 wt %.

Step (30-3): Alkoxylation of Dialkyl Tin Compounds 704.0 g of a solution containing 65.8 wt % of 1,1,3,3-tetra-n-octyl-1,3-didodecyloxy distannoxane were obtained by carrying out the same method as Step (I-6) of Example 1 with the exception of using 600.3 g of the reaction liquid obtained in step (30-2) instead of the reaction liquid obtained in step (1-5) of Example 1, and using 880 mL of 0.1 mol/L aqueous potassium hydroxide solution and 2635 g of 1-dodecanol.

Comparative Example 1

Heating of Composition of Deactivated Forms of Dialkyl Tin Catalyst 175 g of the composition of deactivated forms obtained in step (16-2) of Example 16 were placed in a 500 mL pear-shaped flask under a nitrogen atmosphere at atmospheric pressure. A Dimroth condenser and three-way valve were attached to the flask, and the three-way valve was connected to a line containing nitrogen gas flowing at normal pressure.

The flask was immersed in an oil bath preheated to 220° C. and heated for 90 hours. The flask was then cooled and 174.2 g of a solution were recovered in the flask. When $^1$H- and $^{119}$Sn-NMR measurements were carried out on this solution, the peak corresponding to 1,1,3,3-tetra-n-octyl-1,3-bis(2-ethylbutyloxy) distannoxane was found to have disappeared, and a peak corresponding to tri-n-octyl(2-ethylbutyloxy) tin and a plurality of peaks within a range of from −220 to −600 ppm were observed.

Comparative Example 2

175 g of a composition of deactivated forms obtained using the same method as step (16-2) of Example 16 were placed in a 500 mL pear-shaped flask under a nitrogen atmosphere followed by the addition of 191.0 g of phenol (for nucleic acid extraction, Wako Pure Chemical Industries, Ltd., Japan) and stirring for 1 hour at 40° C. A fractionation head equipped with a reflux condenser connected to a distillate collector and a thermometer were attached to the flask, and after the inside of the vessel was replaced with nitrogen in a vacuum, the flask was immersed in an oil bath heated to 50° C. The pressure inside the vessel was gradually reduced and the excess phenol and the like were distilled off to obtain 189.9 g of a residue in the flask. When $^1$H- and $^{119}$Sn-NMR measurements were carried out on this residue, the residue was found to be a mixture of tri-n-octyl phenoxy tin, di-n-octyl diphenoxy tin, and organic tin compounds containing tin atoms demonstrating a plurality of chemical shifts at from −240 to −605 ppm according to $^{119}$Sn-NMR. The content of tri-n-octyl phenoxy tin in the mixture was 25.2 wt %, and the content of di-n-octyl diphenoxy tin was 59.3 wt %.

188.6 g of the mixture were placed in a 200 mL metal pressure vessel under a nitrogen atmosphere. The metal pressure vessel was immersed in an oil bath heated to 250° C. and heated for 6 hours. After allowing the pressure-resistant reaction vessel to cool to the vicinity of room temperature, 187.5 g of a reaction liquid were recovered. When $^1$H- and $^{119}$Sn-NMR measurement were carried out on this reaction liquid, the content of tri-n-octyl phenoxy tin in the reaction liquid was found to be 36.4 wt % and the content of di-n-octyl diphenoxy tin was 41.1 wt %.

Comparative Example 3

Step (III-1): Separation of Tri-n-octyl (3-Methylbutyloxy) Tin 66.5 g of a distillate in the form of tri-n-octyl (3-methylbutyloxy) tin were obtained by carrying out the same method as step (11-1) of Example 11 using 300 g of a composition of deactivated forms obtained using the same method as step (7-2) of Example 7. The residue in the flask contained 77.1 wt % of 1,1,3,3-tetra-n-octyl-1,3-bis(3-methylbutyloxy) distannoxane, and according to $^{119}$Sn-NMR, 232.5 g of a mixture of organic tin compounds containing tin atoms demonstrating a plurality of chemical shifts at from −240 to −605 ppm.

Step (III-2): Substituent Exchange Reaction of Tri-n-octyl (3-Methylbutyloxy) Tin 65.3 g of the tri-n-octyl (3-methylbutyloxy) tin obtained in step (111-1) were placed in a 300 mL pear-shaped flask followed by the addition of 61.1 g of acetic anhydride and stirring for 1 hour at 25° C. A fractionation head equipped with a reflux condenser connected to a distillate collector and a thermometer were attached to the flask, and after the inside of the vessel was replaced with nitrogen in a vacuum, the flask was immersed in an oil bath heated to 50° C. The pressure inside the vessel was gradually reduced and the isoamyl acetate and excess acetic anhydride were distilled off to obtain 65.3 g of a residue in the flask. When $^1$H- and $^{119}$Sn-NMR measurement were carried out on the residue, the residue was found to be tri-n-octyl acetoxy tin, and the content of tri-n-octyl acetoxy tin was 99 wt %.

Step (III-3): Heat Treatment of Tri-n-octyl Acetoxy Tin 62.4 g of a reaction product were recovered by carrying out the same method as step (1-5) of Example 1 with the exception of using 63.3 g of the tri-n-octyl acetoxy tin obtained in step (III-2) instead of the mixture obtained in step (1-4) of Example 1. When $^1$H- and $^{119}$Sn-NMR measurements were carried out on the reaction liquid, the reaction product was found to contain 98 wt % of tri-n-octyl acetoxy tin.

Comparative Example 4

Step (IV-1): Substituent Exchange Reaction of Deactivated Forms of Dialkyl Tin Catalyst 232.1 g of the residue in the flask obtained in step (111-1) of Comparative Example 3 were placed in a 500 mL metal pressure vessel followed by the addition of 187.6 g of acetic anhydride and stirring. The metal pressure vessel was immersed in an oil bath heated to 200° C. and heated for 3 hours. After allowing the metal pressure vessel to cool to the vicinity of room temperature (about 25° C.), the contents were transferred to a 500 mL pear-shaped flask. A fractionation head equipped with a reflux condenser connected to a distillate collector and a thermometer were attached to the flask, and after the inside of the vessel was replaced with nitrogen in a vacuum, the flask was immersed in an oil bath heated to 50° C. The pressure inside the vessel was gradually reduced and the excess acetic anhydride and the like were distilled off to obtain 248.2 g of a residue in the flask. When $^1$H- and $^{119}$Sn-NMR measurement were carried out on the residue, the residue was found to be a mixture containing di-n-octyl diacetoxy tin and n-octyl triacetoxy tin, and the content of di-n-octyl diacetoxy tin in the mixture was 77.8 wt % while the content of n-octyl triacetoxy tin was 22.1 wt %.

Step (IV-2): Heat Treatment of Deactivated Forms of Substituent-Exchanged Dialkyl Tin Catalyst 244.8 g of a reaction product were recovered by carrying out the same method as step (1-5) of Example 1 with the exception of using 245.4 g of the mixture obtained in step (IV-1) instead of the mixture obtained in step (1-4) of Example 1. When $^1$H- and $^{119}$Sn-NMR measurements were carried out on the reaction liquid, the reaction liquid was found to be a mixture containing di-n-octyl diacetoxy tin and n-octyl triacetoxy tin, and the content of di-n-octyl diacetoxy tin in the mixture was 77.7 wt % while the content of n-octyl triacetoxy tin was 22.1 wt %.

INDUSTRIAL APPLICABILITY

Since the dialkyl tin compound production process of the present invention can be used in such fields as the production of carbonic acid esters and ester exchange reactions, and enables the production and reuse of dialkyl tin compounds and dialkyl tin catalysts useful as catalysts from compositions of deactivated forms of dialkyl tin catalysts for which there was no choice but to be discarded in the past, the production process as claimed in the present invention is extremely industrially useful and has high commercial value.

We claim:
1. A process for producing a dialkyl tin compound, comprising:
    subjecting a composition of a deactivated form of a dialkyl tin catalyst, which is formed when producing an ester compound using the dialkyl tin catalyst, to an alkyl group redistribution reaction and/or dealkylation reaction.
2. The process according to claim 1, wherein the dialkyl tin catalyst is at least one type of compound selected from the group consisting of a dialkyl tin compound represented by formula (1) and a tetraalkyl distannoxane compound represented by formula (2):

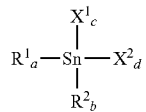

(wherein each of $R^1$ and $R^2$ independently represents a linear or branched alkyl group having 1 to 12 carbon atoms,
    each of $X^1$ and $X^2$ independently represents at least one type of substituent selected from the group consisting of an alkoxy group, an acyloxyl group and a halogen atom,
    a and b independently represent an integer of 0 to 2 and a+b=2, and
    c and d independently represent an integer of 0 to 2 and c+d=2;

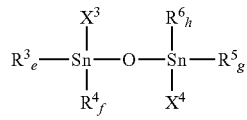

(wherein each of $R^3$, $R^4$, $R^5$ and $R^6$ independently represents a linear or branched alkyl group having 1 to 12 carbon atoms,
    each of $X^3$ and $X^4$ independently represents at least one type of substituent selected from the group consisting of an alkoxy group, an acyloxyl group and a halogen atom, and
    e, f, g and h independently represent an integer of 0 to 2, e+f=2 and g+h=2).
3. The process according to claim 2, wherein in formulas (1) and (2), the number of carbon atoms constituting $X^1$, $X^2$, $X^3$ and $X^4$ is a number selected from an integer of 0 to 12.
4. The process according to claim 1, wherein the ester compound is at least one type of compound selected from the group consisting of carboxylic acid ester, carbaminic acid ester and isocyanate.
5. The process according to claim 4, wherein the carboxylic acid ester is a carbonic acid ester.
6. The process according to claim 5, wherein the composition of the deactivated form of the dialkyl tin catalyst is a composition containing a deactivated form of the dialkyl tin catalyst generated during a step of producing a carbonic acid ester from carbon dioxide and the dialkyl tin catalyst.
7. The process according to claim 1, wherein the deactivated form of the dialkyl tin catalyst is a heat-deactivated form of the dialkyl tin catalyst.
8. The process according to claim 1, wherein the deactivated form of the dialkyl tin catalyst is a deactivated form of the dialkyl tin catalyst originating from the dialkyl tin catalyst in which the number of alkyl group bound to a single tin atom differs from the number of alkyl group bound to a single tin atom of the dialkyl tin catalyst.
9. The process according to claim 1, wherein at least one type of the deactivated form of the dialkyl tin catalyst is a trialkyl tin compound.
10. The process according to claim 1, wherein the deactivated form of the dialkyl tin catalyst is a trialkyl tin compound and an organic tin compound containing a tin atom demonstrating a chemical shift at from −220 to −610 ppm based on a tetramethyl tin when analyzed by $^{119}$Sn-NMR in a heavy chloroform solution.

11. The process according to claim 10, further comprising separating the composition of the deactivated form of the dialkyl tin catalyst into a composition containing the trialkyl tin compound and a composition containing the compound containing a tin atom demonstrating a chemical shift at from −220 to −610 ppm based on a tetramethyl tin when analyzed by $^{119}$Sn-NMR in a heavy chloroform solution.

12. The process according to claim 11, wherein the separation step is carried out by at least one method selected from the group consisting of distillation separation, extraction separation and membrane separation.

13. The process according to claim 1, wherein in a case that pKa of a conjugated acid with respect to at least one substituent among groups bound to tin atoms of the deactivated form of the dialkyl tin catalyst other than alkyl groups originating from the dialkyl tin catalyst is 0 to 6.8,
the alkyl group redistribution reaction is an alkyl group redistribution reaction in which an organic tin compound having an Sn—Y bond (wherein Y represents Y in which pKa of a conjugated acid of Y in a form of HY, in which a hydrogen atom has been added to Y, is 0 to 6.8) is heat-treated.

14. The process according to claim 1, wherein in a case that pKa of a conjugated acid with respect to at least one substituent among groups bound to tin atoms of the deactivated form of the dialkyl tin catalyst other than alkyl groups originating from the dialkyl tin catalyst is 6.8 to 25,
the alkyl group redistribution reaction comprises the steps of:
(A) obtaining an organic tin compound having an Sn—Y bond by substituting all or a portion of the ligands of the deactivated form (excluding an alkyl group originating from the dialkyl tin catalyst and bound to tin) with a substituent Y; and
(B) heat-treating the organic compound having an Sn—Y bond and obtained in step (A) (wherein Y represents Y in which pKa of a conjugated acid of Y in a form of HY, in which a hydrogen atom has been added to Y, is 0 to 6.8).

15. The process according to claim 14, wherein the step (A) comprises producing an organic tin compound having an Sn—Y bond in which three alkyl groups and a single Y group originating from an acid and/or acid anhydride are bound to a single tin atom, and an organic tin compound having an Sn—Y bond in which a single alkyl group and a number of Y groups originating from an acid and/or acid anhydride, the number of Y groups being selected from an integer of 1 to 3, are bound to a single tin atom, by reacting the composition of deactivated form of the dialkyl tin catalyst with the acid represented by the following formula (3) and/or the acid anhydride represented by the following formula (4):

(wherein Y represents Y in which pKa of a conjugated acid of Y in a form of HY, in which a hydrogen atom has been added to Y, is 0 to 6.8);

(wherein Y represents Y in which pKa of a conjugated acid of Y in a form of HY, in which a hydrogen atom has been added to Y, is 0 to 6.8, and 0 represents an oxygen atom).

16. The process according to claim 15, wherein the step (A) is carried out while removing water generated during a use of acid in the step (A) by at least one method selected from the group consisting of removal with a dehydrating agent, distillation separation and membrane separation.

17. The process according to claim 1, wherein the dealkylation reaction comprises forming an Sn—Y bond by eliminating an alkyl group from the deactivated form of the dialkyl tin catalyst (wherein Y represents Y in which pKa of a conjugated acid of Y in a form of HY, in which a hydrogen atom has been added to Y, is 0 to 6.8).

18. The process according to claim 9, wherein the dealkylation reaction forms a single Sn—Y bond by eliminating a single alkyl group from the trialkyl tin compound contained in the composition of the deactivated form of the dialkyl tin catalyst to obtain a dialkyl tin compound having an Sn—Y bond (wherein Y represents Y in which pKa of a conjugated acid of Y in a form of HY, in which a hydrogen atom has been added to Y, is 0 to 6.8).

19. The process according to claim 18, wherein the forming step of the Sn—Y bond comprises reacting the trialkyl tin compound contained in the composition of the deactivated form of the dialkyl tin catalyst with an acid represented by formula (5) and/or an acid anhydride represented by formula (6):

(wherein Y represents Y in which pKa of a conjugated acid of Y in a form of HY, in which a hydrogen atom has been added to Y, is 0 to 6.8);

(wherein Y represents Y in which pKa of a conjugated acid of Y in a form of HY, in which a hydrogen atom has been added to Y, is 0 to 6.8, and 0 represents an oxygen atom).

20. The process according to claim 15 or 19, wherein the acid and/or the acid anhydride is a liquid or gas at 60° C.

21. The process according to claim 20, wherein the acid is a hydrohalogenic acid.

22. The process according to claim 20, wherein the acid is a hydrogen halide.

23. The process according to claim 20, wherein the acid is an organic acid.

24. The process according to claim 23, wherein the organic acid is a carboxylic acid.

25. The process according to claim 20, wherein a standard boiling point of the acid anhydride is 300° C. or lower.

26. The process according to claim 25, wherein the acid anhydride is acetic anhydride or maleic anhydride.

27. The process according to claim 1, wherein the dialkyl tin compound has two alkyl groups originating from a dialkyl tin catalyst and bound to a single tin atom while simultaneously having at least one Sn—Y bond (wherein Y represents Y in which pKa of a conjugated acid of Y in a form of HY, in which a hydrogen atom has been added to Y, is 0 to 6.8).

28. The process according to claim 27, wherein the dialkyl tin compound is at least one type of compound selected from the group consisting of a dialkyl tin compound represented by formula (7) and a tetraalkyl distannoxane compound represented by formula (8):

(wherein $R^7$ and $R^8$ represent a group originating from the dialkyl tin catalyst, and independeltly represent a linear or branched alkyl group having 1 to 12 carbon atoms,
Y represents a group originating from the dialkyl tin catalyst or a group originating from the acid (HY) and/or acid anhydride (YOY), pKa of a conjugated acid of Y in a form of HY in which a hydrogen atom has been added to Y is 0 to 6.8, and i and j independently represent an integer of 0 to 2, and i+j=2);

(8)

(wherein $R^9$, $R_{10}$, $R_{11}$ and $R^{12}$ represents a group originating from the dialkyl tin catalyst, and independently represent a linear or branched alkyl group having 1 to 12 carbon atoms, Y represents a group originating from the dialkyl tin catalyst or a group originating from the acid (HY) and/or acid anhydride (YOY), pKa of a conjugated acid of Y in a form of HY in which a hydrogen atom has been added to Y is 0 to 6.8, and k, l, m and n respectively represent an integer of 0 to 2, k+l=2 and m+n=2).

29. The process according to claim 12, further comprising, following the step (B), a step (I) of substituting substituent Y of the dialkyl tin compound having an Sn—Y bond with at least one type of substituent selected from the group consisting of an alkoxy group, and acyloxyl group and halogen atom.

30. The process according to claim 29, wherein the step (I) comprises:

a step (I-1) of obtaining a composition containing a dialkyl tin oxide by hydrolyzing the dialkyl tin compound having an Sn—Y bond by adding an aqueous alkaline solution; and a step (I-2) of reacting the composition containing the dialkyl tin oxide, obtained in the step (I-1) with at least one type of compound selected from the group consisting of alcohol, carboxylic acid and hydrogen halide, followed by removing a component containing a generated water from a reaction liquid.

31. The process according to claim 30, wherein the aqueous alkaline solution is at least one type of aqueous alkaline solution selected from the group consisting of an aqueous sodium hydroxide solution, an aqueous potassium hydroxide solution, an aqueous potassium carbonate solution and an aqueous sodium carbonate solution.

32. The process according to claim 30 or 31, wherein the step (I-2) is a step in which the compound reacted with the composition containing the dialkyl tin oxide is alcohol, and a dialkyl tin alkoxide compound is obtained.

33. The process according to claim 6, wherein the step for producing a carbonic acid ester comprises:

a step (1) of obtaining a reaction liquid containing the carbonic acid ester by reacting carbon dioxide and the dialkyl tin catalyst;

a step (2) of obtaining a residual liquid by separating the carbonic acid ester from the reaction liquid;

a step (3) of regenerating the dialkyl tin catalyst by reacting the residual liquid and alcohol, and removing a generated water outside the system; and a step (4) of recycling the dialkyl tin catalyst obtained in step (3) to step (1).

34. The process according to claim 33, wherein the step of regenerating the dialkyl tin catalyst from the composition of the deactivated form of the dialkyl tin catalyst generated during the step for producing the carbonic acid ester by the alkyl group redistribution reaction and/or the dealkylation reaction is carried out after the step (2) and/or the step (3), and the regenerated dialkyl tin catalyst is recycled and reused as the dialkyl tin catalyst of the step (4) and/or the step (1).

35. The process according to claim 34, wherein the step of regenerating the dialkyl tin catalyst is a step which uses the steps according to any one of claims 29 to 32 and in which substituent Y represents an acyloxyl group.

36. The process according to claim 1, wherein the dialkyl tin catalyst is a dialkyl tin alkoxide compound.

37. The process according to claim 33, wherein the dialkyl tin catalyst is a dialkyl tin alkoxide compound, and $X^1$, $X^2$, $X^3$ and $X^4$ of a compound represented by formula (1) and/or formula (2) represent alkoxy groups:

(1)

(wherein each of $R^1$ and $R^2$ independently represents a linear or branched alkyl group having 1 to 12 carbon atoms, each of $X^1$ and $X^2$ independently represents at least one type of substituent selected from the group consisting of an alkoxy group, an acyloxyl group and a halogen atom, a and b independently represent an integer of 0 to 2 and a+b=2, and c and d independently represent an integer of 0 to 2 and c+d=2);

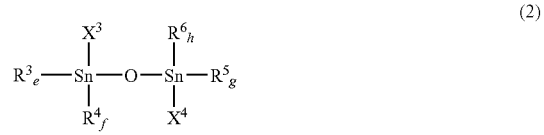

(2)

(wherein each of $R^3$, $R^4$, $R^5$ and $R^6$ independently represents a linear or branched alkyl group having 1 to 12 carbon atoms, each of $X^3$ and $X^4$ independently represents at least one type of substituent selected from the group consisting of an alkoxy group, an acyloxyl group and a halogen atom, e, f, g and h respectively represent an integer of 0 to 2, e+f=2 and g+h=2).

38. The process according to claim 37, wherein the dialkyl tin catalyst is a dialkyl tin alkoxide, and $R^1$, $R^2$, $R^3$, $R^4$, $R^5$ and $R^6$ of the compound represented by the formula (1) and/or the formula (2) simultaneously represents a n-butyl group or a n-octyl group.

39. The process according to claim 33, wherein the alcohol is an alcohol represented by the following formula (9):

$R^{13}OH$ (9)

(wherein $R^{13}$ represents a linear or branched alkyl group having 4 to 8 carbon atoms).

* * * * *